US007993831B2

(12) United States Patent
Latham et al.

(10) Patent No.: US 7,993,831 B2
(45) Date of Patent: Aug. 9, 2011

(54) METHODS OF NORMALIZATION IN MICRORNA DETECTION ASSAYS

(75) Inventors: Gary J. Latham, Austin, TX (US); Heidi J. Peltier, Austin, TX (US)

(73) Assignee: Asuragen, Inc., Austin, TX (US)

( * ) Notice: Subject to any disclaimer, the term of this patent is extended or adjusted under 35 U.S.C. 154(b) by 0 days.

(21) Appl. No.: 11/855,792

(22) Filed: Sep. 14, 2007

(65) Prior Publication Data

US 2009/0075258 A1 Mar. 19, 2009

(51) Int. Cl.
*C12Q 1/68* (2006.01)
*C12P 19/34* (2006.01)
*C07H 21/02* (2006.01)
*C07H 21/04* (2006.01)
(52) U.S. Cl. .......... 435/6; 435/91.1; 536/23.1; 536/24.3
(58) Field of Classification Search ............. 435/6, 91.1, 435/91.31; 536/23.1, 24.5, 24.3
See application file for complete search history.

(56) References Cited

U.S. PATENT DOCUMENTS

| | | | |
|---|---|---|---|
| 5,736,333 | A | 4/1998 | Livak et al. |
| 2005/0266418 | A1 | 12/2005 | Chen et al. |
| 2006/0078894 | A1 | 4/2006 | Winkler et al. |
| 2008/0306018 | A1* | 12/2008 | Croce et al. .................. 514/44 |

OTHER PUBLICATIONS

Ota, A. et al., Cancer Research, vol. 64, pp. 3087-3095 (2004).*
Lim et al., Genes & Dev., vol. 17, pp. 991-1008 (2003).*
Abruzzo et al., "Validation of oligonucleotide microarray data using microfluidic low-density arrays: a new statistical method to normalize real-time RT-PCR data," *BioTechniques* 38:785-792 (2005).
Andersen et al., "Normalization of Real-Time Quantitative Reverse Transcription-PCR Data: A Model-Based Variance Estimation Approach to Identify Genes Suited for Normalization, Applied to Bladder and Colon Cancer Data Sets," *Cancer Research* 64:5245-5250 (2004).
Applied Biosystems User Bulletin #2, "ABI Prism 7700 Sequence Detection System," P/N 4303859B (2001).
Bandres et al., "Identification by Real-time PCR of 13 mature microRNAs differentially expressed in colorectal cancer in non-tumoral tissues," *Molecular Cancer* 5:29 (2006).
Bijwaard et al., "Detection of *SYT-SSX* Fusion Transcripts in Archival Synovial Sarcomas by Real-Time Reverse Transcriptase-Polymerase Chain Reaction," *Journal of Molecular Diagnostics* 4(1):59-64 (2002).
Calin et al., "MicroRNA-Cancer Connection: The Beginning of a New Tale," *Cancer Res* 66(15):7390-7394 (2006).
Chen et al., "Real-time quantification of microRNAs by stem-loop RT-PCR," *Nucleic Acids Research* 33(20):e179 (2005).
Chen et al., "Differential Patterns of MicroRNA Expression in Neuroblastoma Are Correlated with Prognosis, Differentiation, and Apoptosis," *Cancer Research* 67(3):976-983 (Feb. 2007).
Cummins et al., "The colorectal microRNAome," *Proc. Natl. Acad. Sci.* 103(10):3687-3692 (2006).
Davoren et al., "Comparison of endogenous control genes for normalisation of relative quantitative real-time PCR data in a study characterising microRNA expression in human breast cancer tissues," qPCR 2007 Symposium, Freising-Weihenstephan, Germany, Mar. 26, 2007. http://qpcr2007.gene-quantification.info/.
de Kok et al., "Normalization of gene expression measurements in tumor tissues: comparison of 13 endogenous control genes," *Laboratory Investigation* 85:154-159 (2005).
Erickson et al., "Assessment of normalization strategies for quantitative RT-PCR using microdissected tissue samples," *Lab Invest* 87(9):951-62 (Sep. 2007).
Garzon et al., "MicroRNA fingerprints during human megakaryocytopoiesis," *PNAS* 103(13):5078-5083 (2006).
Huber et al., "Variance stabilization applied to microarray data calibration and to the quantification of differential expression," *Bioinformatics* 18:S96-S104 (2002).
Inamura et al., "let-7 microRNA expression is reduced in bronchioloaveolar carcinoma, a non-invasive carcinoma, and is not correlated with prognosis," *Lung Cancer* 58:392-396 (2007).
Iorio et al., "MicroRNA Gene Expression Deregulation in Human Breast Cancer," *Cancer Research* 65(16):7065-7070 (2005).
Jansen et al., "Efficient and easy detection of MLL-AF4, MLL-AF9 and MLL-ENL fusion gene transcripts by multiplex real-time quantitative RT-PCR in TaqMan and LightCycler," *Leukemia* 19(11):2016-2018 (2005).
Kemppainen et al., "microRNAs as biomarkers in blood and other biofluids," poster presented at Keystone meeting "MicroRNAs and siRNAs: Biological Functions and Mechanisms (J5)," Keystone, CO. Jan. 28-Feb. 2, 2007. http://asuragen.com/pdfs/posters/biomarkers.pdf.
Lee et al., "Expression profiling identifies microRNA signature in pancreatic cancer," *Int. Journal Cancer* 120(5):1046-1054 (2007).
Li et al., "Antiprimer Quenching-Based Real-Time PCR and Its Application to the Analysis of Clinical Cancer Samples," *Clin. Chem.* 52(4):624-633 (2006).
Mattie et al., "Optimized high-throughput microRNA expression profiling provides novel biomarker assessment of clinical prostate and breast cancer biopsies," *Molecular Cancer* 5:24 (2006).
Michael et al., "Reduced Accumulation of Specific MicroRNAs in Colorectal Neoplasia," *Molecular Cancer Research* 1:882-891 (2003).
Molenkamp et al., "Simultaneous detection of five different DNA targets by real-time Taqman PCR using the Roche LightCycler480: Application in viral molecular diagnostics," *J. Virol Methods* 141(2):205-11 (2007).
Payungporn et al. "Single step multiplex real-time RT-PCR for H5N1 influenza A virus detection," *J. Virol Methods* 131(2):143-147 (2006).
Pfaffl, "Relative mRNA quantification using real-time qRT-PCR: Recent advances and new perspectives," BioTechnica 2005, Oct. 19, 2005, Hannover.
Pfaffl, "Determination of stable housekeeping genes, differentially regulated target genes and sample integrity: BestKeeper—Excel-based tool using pair-wise correlations," *Biotechnol Lett.* 26(6):509-15 (2004).
Schouten et al., "Relative quantification of 40 nucleic acid sequences by multiplex ligation-dependent probe amplification," *Nucleic Acids Research* 30(12):e57 (2002).

(Continued)

*Primary Examiner* — Jane Zara
(74) *Attorney, Agent, or Firm* — Finnegan, Henderson, Farabow, Garrett & Dunner, LLP

(57) ABSTRACT

This application describes methods of quantifying a target miRNA in a biological sample by measuring the amounts of a target miRNA and at least one reference oncomir in a reaction volume, and normalizing the amount of target miRNA to the amount of one or more reference oncomirs.

24 Claims, 11 Drawing Sheets

OTHER PUBLICATIONS

Shingara et al., "An optimized isolation and labeling platform for accurate microRNA expression profiling," *RNA* 11:1461-1470 (2005).

Shulzhenko et al., "Selection of control genes for quantitative RT-PCR based on microarray data," *Biochemical and Biophysical Research Communication* 337:306-312 (2005).

Spinsanti et al., "Selection of reference genes for quantitative RT-PCR studies in striped dolphin (*Stenella coeruleoalba*) skin biopsies," *BMC Molecular Biology* 7:32 (2006).

Szabo et al., "Statistical modeling for selecting housekeeper genes," *Genome Biol.* 5(8):R59 (2004).

Szafranzka et al., "MicroRNA expression alterations are linked to tumorigenesis and non-neoplastic processes in pancreatic ductal adenocarcinoma," *Oncogene* 26:1-11 (2007).

Vandesompele et al., "Accurate normalization of real-time quantitative RT-PCR data by geometric averaging of multiple internal control genes," *Genome Biol.* 3(7):research0034.1-0034.11 (2002).

Vandesompele, "Gene expression profiling: accurate normalisation and automated data-analysis," qPCR Satellite Symposium, Mar. 11, 2005, Leipzig, Germany.

Vandesompele, "geNorm user manual," Sep. 6, 2004. http://medgen.ugent.be/~jvdesomp/genorm/.

Wiemer, "The role of microRNAs in cancer: No small matter," *European Journal of Cancer* 43:1529-1544 (2007).

Wong et al., "Real-time PCR for mRNA quantitation," *BioTechniques* 39(1): 1-11 (2005).

Zhang et al., "microRNAs exhibit high frequency genomic alterations in human cancer," *Proc. Natl. Acad. Sci.* 103(24):9136-9141 (2005).

* cited by examiner

Figure 1A

| Seq ID | Name | Sequence | Seq ID | Name | Sequence |
|---|---|---|---|---|---|
| 1 | let-7a | ugagguaguagguugauaguu | 50 | miR-192 | cugaccaugaauugacagcc |
| 2 | let-7b | ugagguaguagguugugugguu | 51 | miR-195 | uagcagcacagaaauauuggc |
| 3 | let-7c | ugagguaguagguuguaugguu | 52 | miR-197 | uucaccaccuucuccacccagc |
| 4 | let-7d | agagguaguagguugcauaguu | 53 | miR-199a-5p | cccaguguucagacuaccuguuc |
| 5 | let-7e | ugagguaggagguuguauaguu | 54 | miR-199a-3p | acaguagucugcacauugguua |
| 6 | let-7f | ugagguaguagauuguauaguu | 55 | miR-19a | ugugcaaaucuaugcaaaacuga |
| 7 | let-7g | ugagguaguaguuuguacaguu | 56 | miR-19b | ugugcaaauccaugcaaaacuga |
| 8 | let-7i | ugagguaguaguuugugcuguu | 57 | miR-200a | uaacacugucugguaacgaugu |
| 9 | miR-100 | aacccguagauccgaacuugug | 58 | miR-200a* | caucuuaccggacagugcggaa |
| 10 | miR-103 | agcagcauuguacagggcuauga | 59 | miR-200b | uaauacugccugguaaugauga |
| 11 | miR-106a | aaaagugcuuacagugcagguag | 60 | miR-200c | uaauacugccggguaaugauga |
| 12 | miR-107 | agcagcauuguacagggcuauca | 61 | miR-202 | agagguauaggggcaugggaa |
| 13 | miR-10a | uacccuguagauccgaauuugug | 62 | miR-203 | gugaaauguuuaggaccacuag |
| 14 | miR-10b | uacccuguagaaccgaauuugug | 63 | miR-205 | uccuucauuccaccggagucug |
| 15 | miR-122 | uggagugugacaaugguguuug | 64 | miR-20a | uaaagugcuuauagugcagguag |
| 16 | miR-125a-5p | ucccugagacccuuuaaccuguga | 65 | miR-21 | uagcuuaucagacugauguuga |
| 17 | miR-125b | ucccugagacccuaacuuguga | 66 | miR-210 | cugugcgugugacagcggcuga |
| 18 | miR-126 | ucguaccgugaguaauaaugcg | 67 | miR-216 | uaaucucagcuggcaacuguga |
| 19 | miR-126* | cauuauuacuuuuggacgcg | 68 | miR-218 | uugugcuugaucuaaccaugu |
| 20 | miR-127-3p | ucggauccgucugagcuuggcu | 69 | miR-22 | aagcugccaguugaagaacugu |
| 21 | miR-128a | ucacagugaaccggucucuuu | 70 | miR-221 | agcuacauugucugcuggguuuc |
| 22 | miR-129-5p | cuuuuugcggucugggcuugc | 71 | miR-222 | agcuacaucugguacugggu |
| 23 | miR-133b | uuuggucccuucaaccagcua | 72 | miR-223 | ugucaguuugucaaaauccccca |
| 24 | miR-135b | uauggcuuuucauuccuauguga | 73 | miR-224 | caagucacuaguugguuccguu |
| 25 | miR-137 | uuauugcuuaagaauacgcguag | 74 | miR-23a | aucacauugccagggauuucc |
| 26 | miR-141 | uaacacugucugguaaagaugg | 75 | miR-23b | aucacauugccagggauuacc |
| 27 | miR-143 | ugagaugaagcacuguagcuc | 76 | miR-24 | uggcucaguucagcaggaacag |
| 28 | miR-145 | guccaguuucccaggaaucccu | 77 | miR-25 | cauugcacuugucucggucuga |
| 29 | miR-146a | ugagaacugaauuccaugggu | 78 | miR-26a | uucaaguaauccaggauaggcu |
| 30 | miR-146b-5p | ugagaacugaauuccauaggcu | 79 | miR-26b | uucaaguaauucaggauaggu |
| 31 | miR-148a | ucagugcacuacagaacuuugu | 80 | miR-27a | uucacaguggcuaaguuccgc |
| 32 | miR-149 | ucuggcuccgugucuucacuccc | 81 | miR-27b | uucacaguggcuaaguucugc |
| 33 | miR-150 | ucucccaacccuuguaccagug | 82 | miR-29a | uagcaccaucugaaaucgguua |
| 34 | miR-155 | uuaaugcuaaucgugauaggggu | 83 | miR-29b | uagcaccauuugaaaucaguguu |
| 35 | miR-15a | uagcagcacauaauggauuugug | 84 | miR-296-5p | agggccccccccucaauccugu |
| 36 | miR-16 | uagcagcacguaaauauuggcg | 85 | miR-301 | cagugcaauaguauugucaaagc |
| 37 | miR-17* | acugcagugaaggcacuuguag | 86 | miR-302a | uaagugcuuccauguuuugguga |
| 38 | miR-17 | caaagugcuuacagugcagguag | 87 | miR-302a* | acuuaaacgugggaugauacuugcu |
| 39 | miR-181a | aacauucaacgcugucggugagu | 88 | miR-30a | uguaaacauccucgacuggaag |
| 40 | miR-181b | aacauucauugcugucgguggu | 89 | miR-30b | uguaaacauccuacacucagcu |
| 41 | miR-181c | aacauucaaccugucggugagu | 90 | miR-30c | uguaaacauccuacacucucagc |
| 42 | miR-183 | uauggcacugguagaauucacu | 91 | miR-30d | uguaaacauccccgacuggaag |
| 43 | miR-184 | uggacggagaacugauaaggu | 92 | miR-30e* | cuuucagucggauguuuacagc |
| 44 | miR-186 | caaagaauucuccuuuugggcu | 93 | miR-30e-5p | uguaaacauccuugacuggaag |
| 45 | miR-187 | ucgugucuuguguucagccgg | 94 | miR-31 | aggcaagaugcuggcauagcu |
| 46 | miR-24-1* | ugccuacugagcugauaucagu | 95 | miR-320 | aaaagcugggguugagagggcga |
| 47 | miR-18a | uaaggugcaucuagugcagauag | 96 | miR-323-3p | cacauuacacggucgaccucu |
| 48 | miR-190 | ugauauguuugauauauuaggu | 97 | miR-324-5p | cgcauccccuagggcauuggugu |
| 49 | miR-191 | caacggaaucccaaaagcagcug | 98 | miR-326 | ccucugggcccuuccuccag |

Figure 1B

| | | | | | |
|---|---|---|---|---|---|
| 99 | miR-330-3p | gcaaagcacacggccugcagaga | 107 | miR-373* | acucaaaauggggggcgcuuucc |
| 100 | miR-331-3p | gccccugggccuauccuagaa | 108 | miR-497 | cagcagcacacugugguuugu |
| 101 | miR-335 | ucaagagcaauaacgaaaaaugu | 109 | miR-498 | uuucaagccagggggcguuuuc |
| 102 | miR-346 | ugucugcccgcaugccugccucu | 110 | miR-503 | uagcagcgggaacaguucugcag |
| 103 | miR-34a | uggcagugucuuagcugguugu | 111 | miR-92 | uauugcacuugucccggccugu |
| 104 | miR-370 | gccugcuggggguggaaccuggu | 112 | miR-93 | caaagugcuguucgugcagguag |
| 105 | miR-372 | aaagugcugcgacauuugagcgu | 113 | miR-96 | uuuggcacuagcacauuuuugcu |
| 106 | miR-373 | gaagugcuucgauuuuggggugu | 114 | miR-99a | aacccguagauccgaucuugug |
| 115 | let-7a-1 | UGGGAUGAGGUAGUAGGUUGUAUAGUUUUAGGGUCACACCCACCACUGGGAGAUAACUAUACAAUCUACUGUCUUUCCUA |
| 116 | let-7a-2 | AGGUUGAGGUAGUAGGUUGUAUAGUUUAGAAUUACAUCAAGGGAGAUAACUGUACAGCCUCCUAGCUUUCCU |
| 117 | let-7a-3 | GGGUGAGGUAGUAGGUUGUAUAGUUUGGGGCUCUGCCCUGCUAUGGGAUAACUAUACAAUCUACUGUCUUUCCU |
| 118 | let-7b | CGGGGUGAGGUAGUAGGUUGUGUGGUUUCAGGGCAGUGAUGUUGCCCCUCGGAAGAUAACUAUACAACCUACUGCCUUCCCUG |
| 119 | let-7c | GCAUCCGGGUUGAGGUAGUAGGUUGUAUGGUUUAGAGUUACACCCUGGGAGUUAACUGUACAACCUUCUAGCUUUCCUUGGAGC |
| 120 | let-7d | CCUAGGAAGAGGUAGUAGGUUGCAUAGUUUUAGGGCAGGGAUUUUGCCCACAAGGAGGUAACUAUACGACCUGCUGCCUUUCUUAGG |
| 121 | let-7e | CCCGGGCUGAGGUAGGAGGUUGUAUAGUUGAGGAGGACACCCAAGGAGAUCACUAUACGGCCUCCUAGCUUUCCCCAGG |
| 122 | let-7f-1 | UCAGAGUGAGGUAGUAGAUUGUAUAGUUGUGGGGUAGUGAUUUUACCCUGUUCAGGAGAUAACUAUACAAUCUAUUGCCUUCCCUGA |
| 123 | let-7f-2 | UGUGGGAUGAGGUAGUAGAUUGUAUAGUUUUAGGGUCAUACCCCAUCUUGGAGAUAACUAUACAGUCUACUGUCUUUCCCACG |
| 124 | let-7g | AGGCUGAGGUAGUAGUUUGUACAGUUUGAGGGUCUAUGAUACCACCCGGUACAGGAGAUAACUGUACAGGCCACUGCCUUGCCA |
| 125 | let-7i | CUGGCUGAGGUAGUAGUUUGUGCUGUUGGUCGGGUUGUGACAUUGCCCGCUGUGGAGAUAACUGCGCAAGCUACUGCCUUGCUA |
| 126 | miR-100 | CCUGUUGCCACAAACCCGUAGAUCCGAACUUGUGGUAUUAGUCCGCACAAGCUUGUAUCUAUAGGUAUGUGUCUGUUAGG |
| 127 | miR-103-1 | UACUGCCCUCGGCUUCUUUACAGUGCUGCCUUGUUGCAUAUGGAUCAAGCAGCAUUGUACAGGGCUAUGAAGGCAUUG |
| 128 | miR-103-2 | UUGUGCUUUCAGCUUCUUUACAGUGCUGCCUUGUAGCAUUCAGGUCAAGCAGCAUUGUACAGGGCUAUGAAAGAACCA |
| 129 | miR-106a | CCUUGGCCAUGUAAAAGUGCUUACAGUGCAGGUAGCUUUUUGAGAUCUACUGCAAUGUAAGCACUUCUUACAUUACCAUGG |
| 130 | miR-107 | CUCUCUGCUUUCAGCUUCUUUACAGUGUUGCCUUGUGGCAUGGAGUUCAAGCAGCAUUGUACAGGGCUAUCAAAGCACAGA |
| 131 | miR-10a | GAUCUGUCUGUCUUCUGUAUAUACCCUGUAGAUCCGAAUUUGUGUAAGGAAUUUUGUGGUCACAAAUUCGUAUCUAGGGGAAUAUGUAGUUGCAUAAAACAUCCGCUCU |
| 132 | miR-10b | CCAGAGGUUGUAACGUUGUCUAUAUAUACCCUGUAGAACCGAAUUUGUGUGGUAUCCGUAUAGUCACAGAUUCGAUUCUAGGGGAAUAUAUGGUCGAUGCAAAAACUUCA |
| 133 | miR-122 | CCUUAGCAGAGCUGUGGAGUGUGACAAUGGUGUUUGUGUCUAAACUAUCAAACGCCAUUAUCACACUAAAUAGCUACUGCUAGGC |
| 134 | miR-125a | UGCCAGUCUCUAGGUCCCUGAGACCCUUUAACCUGUGAGGACAUCCAGGGUCACAGGUGAGGUUCUUGGGAGCCUGGCGUCUGGCC |
| 135 | miR-125b-1 | UGCGCUCCUCUCAGUCCCUGAGACCCUAACUUGUGAUGUUUACCGUUUAAAUCCACGGGUUAGGCUCUUGGGAGCUGCGAGUCGUGCU |
| 136 | miR-125b-2 | ACCAGACUUUUCCUAGUCCCUGAGACCCUAACUUGUGAGGUAUUUUAGUAACAUCACAAGUCAGGCUCUUGGGACCUAGGCGGAGGGGA |
| 137 | miR-126 | CGCUGGCGACGGGACAUUAUUACUUUUGGUACGCGCUGUGACACUUCAAACUCGUACCGUGAGUAAUAAUGCGCCGUCCACGGCA |
| 138 | miR-127 | UGUGAUCACUGUCUCCAGCCUGCUGAAGCUCAGAGGGCUCUGAUUCAGAAAGAUCAUCGGAUCCGUCUGAGCUUGGCUGGUCGGAAGUCUCAUCAUC |

Figure 1C

| | | |
|---|---|---|
| 139 | miR-128a | UGAGCUGUUGGAUUCGGGGCCGUAGCACUGUCUGAGAGGUUUACAUUUCUCACAGUGAACCGGUCUCUUUUUCAGCUGCUUC |
| 140 | miR-129-1 | GGAUCUUUUUGCGGUCUGGGCUUGCUGUUCCUCUCAACAGUAGUCAGGAAGCCCUUACCCCAAAAAGUAUCU |
| 141 | miR-129-2 | UGCCCUUCGCGAAUCUUUUUGCGGUCUGGGCUUGCUGUACAUAACUCAAUAGCCGGAAGCCCUUACCCCAAAAAGCAUUUGCGGAGGGCG |
| 142 | miR-133b | CCUCAGAAGAAAGAUGCCCCCUGCUCUGGCUGGUCAAACGGAACCAAGUCCGUCUUCCUGAGAGGUUUGGUCCCCUUCAACCAGCUACAGCAGGGCUGGCAAUGCCCAGUCCUUGGAGA |
| 143 | miR-135b | CACUCUGCUGUGGCCUAUGGCUUUUCAUUCCUAUGUGAUUGCUGUCCCAAACUCAUGUAGGGCUAAAAGCCAUGGGCUACAGUGAGGGGCGAGCUCC |
| 144 | miR-137 | GGUCCUCUGACUCUCUUCGGUGACGGGUAUUCUUGGGUGGAUAAUACGGAUUACGUUGUUAUUGCUUAAGAAUACGCGUAGUCGAGGAGAGUACCAGCGGCA |
| 145 | miR-141 | CGGCCGGCCCUGGGUCCAUCUUCCAGUACAGUGUUGGAUGGUCUAAUUGUGAAGCUCCUAACACUGUCUGGUAAAGAUGGCUCCCGGGUGGGUUC |
| 146 | miR-143 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAAGUUGUUCUGCAGC |
| 147 | miR-145 | CACCUUGUCCUCACGGUCCAGUUUUCCCAGGAAUCCCUUAGAUGCUAAGAUGGGGAUUCCUGGAAAUACUGUUCUUGAGGUCAUGGUU |
| 148 | miR-146a | CCGAUGUGUAUCCUCAGCUUUGAGAACUGAAUUCCAUGGGUUGUGUCAGUGUCAGACCUCUGAAAUUCAGUUCUUCAGCUGGGAUAUCUCUGUCAUCGU |
| 149 | miR-146b | CCUGGCACUGAGAACUGAAUUCCAUAGGCUGUGAGCUCUAGCAAUGCCCUGUGGACUCAGUUCUGGUGCCCGG |
| 150 | miR-148a | GAGGCAAAGUUCUGAGACACUCCGACUCUGAGUAUGAUAGAAGUCAGUGCACUACAGAACUUUGUCUC |
| 151 | miR-149 | GCCGGCGCCCGAGCUCUGGCUCCGUGUCUUCACUCCCGUGCUUGUCCGAGGAGGGAGGGAGGACGGGGGCUGUGCUGGGGCAGCUGGA |
| 152 | miR-150 | CUCCCCAUGGCCCUGUCUCCCAACCCUUGUACCAGUGCUGGGCUCAGACCCUGGUACAGGCCUGGGGGACAGGGACCUGGGGAC |
| 153 | miR-155 | CUGUUAAUGCUAAUCGUGAUAGGGGUUUUUGCCUCCAACUGACUCCUACAUAUUAGCAUUAACAG |
| 154 | miR-15a | CCUUGGAGUAAAGUAGCAGCACAUAAUGGUUUGUGGAUUUUGAAAAGGUGCAGGCCAUAUUGUGCUGCCUCAAAAAUACAAGG |
| 155 | miR-16-1 | GUCAGCAGUGCCUUAGCAGCACGUAAAUAUUGGCGUUAAGAUUCUAAAAUUAUCUCCAGUAUUAACUGUGCUGCUGAAGUAAGGUUGAC |
| 156 | miR-16-2 | GUUCCACUCUAGCAGCACGUAAAUAUUGGCGUAGUGAAAUAUAUUAAACACCAAUAUUACUGUGCUGCUUUAGUGUGAC |
| 157 | miR-17 | GUCAGAAUAAUGUCAAAGUGCUUACAGUGCAGGUAGUGAUAUGUGCAUCUACUGCAGUGAAGGCACUUUGUAGCAUUAUGGUGAC |
| 158 | miR-181a-1 | UGAGUUUUGAGGUUGCUUCAGUGAACAUUCAACGCUGUCGGUGAGUUUGGAAUUAAAAUCAAAACCAUCGACCGUUGAUUGUACCCUAUGGCUAACCAUCAUCUACUCCA |
| 159 | miR-181a-2 | AGAAGGGCUAUCAGGCCAGCCUUCAGAGGACUCCAAGGAACAUUCAACGCUGUCGGUGAGUUUGGGAUUUGAAAAAACCACUGACCGUUGACUGUACCUUGGGGUCCUUA |
| 160 | miR-181b-1 | CCUGUGCAGAGAUUAUUUUUUAAAAGGUCACAAUCAACAUUCAUUGCUGUCGGUGGGUUAACUGUGUGGACAAGCUCACUGAACAAUGAAUGCAACUGUGGCCCCGCUU |
| 161 | miR-181b-2 | CUGAUGGCUGCACUCAACAUUCAUUGCUGUCGGUGGGUUUGAGCUCUGAAUCAACUCACUGAUCAAUGAAUGCAAACUGCGGACCAAACA |
| 162 | miR-181c | CGGAAAAUUUGCCAAGGGUUUGGGGGAACAUUCAACCUGUCGGUGAGUUUGGGCAGCUCAGGCAAACCAUCGACCGUUGAGUGGACCCUGAGGCCUGGAAUUGCCAUCCU |
| 163 | miR-183 | CCGCAGAGUGAUGCACUCCUGUUCUGUGUAUGGCACUGGUAGAAUUCACUGUGAACAGUCUCAGUCAGUGAAUUACCGAAGGGCCAUAAACAGAGCAGAGACAGAUCCACGA |
| 164 | miR-184 | CCAGUCACGUCCCCUUAUCACUUUUCCAGCCCAGCUUUGUGACUGUAAGUGUUGGACGGAGAACUGAUAAGGGUAGGUGAUUGA |
| 165 | miR-186 | UGCUUGUAACUUUCCAAAGAAUUCUCCUUUUGGGCUUUCUGGUUUUAUUUUAAGCCCAAAGGUGAAUUUUUUGGGAAGUUUGAGCU |
| 166 | miR-187 | GGUCGGGCUCACCAUGACACAGUGUGAGACCUCGGGCUACAACACAGGACCCGGGCGCUGCUCUGACCCCUCGUGUCUUGUGUUGCAGCCGGAGGGACGCAGGUCCGCA |
| 167 | miR-18a | UGUUCUAAGGUGCAUCUAGUGCAGAUAGUGAAGUAGAUUAGCAUCUACUGCCCUAAGUGCUCCUUCUGGCA |

Figure 1D

| 168 | miR-190 | UGCAGGCCUCUGUGUGAUAUGUUUGAUAUAUUAGGUUGUUAUUUAAUCCAACUAUAUAUCAAACAUAUUCCUACAGUGUCUUGCC |
|---|---|---|
| 169 | miR-191 | CGGCUGGACAGCGGGCAACGGAAUCCCAAAAGCAGCUGUUGUCUCCAGAGCAUUCCAGCUGCGCUUGGAUUUCGUCCCCUGCUCUCCUGCCU |
| 170 | miR-192 | GCCGAGACCGAGUGCACAGGGCUCUGACCUAUGAAUUGACAGCCAGUGCUCUCGUCUCCCCUCUGGCUGCCAAUUCCAUAGGUCACAGGUAUGUUCGCCUCAAUGCCAGC |
| 171 | miR-195 | AGCUUCCCUGGCUCUAGCAGCACAGAAAUAUUGGCACAGGGAAGCGAGUCUGCCAAUAUUGGCUGUGCUGCUCCAGGCAGGGUGGUG |
| 172 | miR-197 | GGCUGUGCCGGGUAGAGAGGGCAGUGGGAGGUAAGAGCUCUUCACCCUUCACCACCUUCUCCACCCAGCAUGGCC |
| 173 | miR-199a-1 | GCCAACCCAGUGUUCAGACUACCUGUUCAGGAGGCUCUCAAUGUGUACAGUAGUCUGCACAUUGGUUAGGC |
| 174 | miR-199a-2 | AGGAAGCUUCUGGAGAUCCUGCUCCGUCGCCCCAGUGUUCAGACUACCUGUUCAGGACAAUGCCGUUGUACAGUAGUCUGCACAUUGGUUAGACUGGGCAAGGGAGAGCA |
| 175 | miR-19a | GCAGUCCUCUGUUAGUUUUGCAUAGUUGCACUACAAGAAGAAUGUAGUUGUGCAAAUCUAUGCAAAACUGAUGGUGGCCUGC |
| 176 | miR-19b-1 | CACUGUUCUAUGGUUAGUUUUGCAGGUUUGCAUCCAGCUGUGUGAUAUUCUGCUGUGCAAAUCCAUGCAAAAACUGACUGUGGUAGUG |
| 177 | miR-19b-2 | ACAUUGCUACUUACAAUUAGUUUUGCAGGUUUGCAUUUCAGCGUAUAUAUGUAUAUGUGGCUGUGCAAAUCCAUGCAAAACUGAUUGUGAUAAUGU |
| 178 | miR-200a | CCGGGCCCCUGUGAGCAUCUUACCGGACAGUGCUGGAUUUCCCAGCUUGACUCUAACACUGUCUGGUAACGAUGUUCAAAGGUGACCCGC |
| 179 | miR-200b | CCAGCUCGGGCAGCCGUGGCCAUCUUACUGGGCAGCAUUGGAUGGAGUCAGGUCUCUAAUACUGCCUGGUAAUGAUGACGGCGGAGCCCUGCACG |
| 180 | miR-200c | CCCUCGUCUUACCCAGCAGUGUUUGGGUGCGGUUGGGAGUCUCUAAUACUGCCGGGUAAUGAUGGAGG |
| 181 | miR-202 | CGCCUCAGAGCCGCCCGCCGUUCCUUUUUCCUAUGCAUAUACUUCUUUGAGGAUCUGGCCUAAAGAGGUAUAGGGCAUGGGAAAACGGGGCGGUCGGGUCCUCCCCAGCG |
| 182 | miR-203 | GUGUUGGGACUCGCGCGCUGGGUCCAGUGGUUCUUAACAGUUCAACAGUUCUGUAGCGCAAUUGUGAAAUGUUAGGACCACUAGACCCGGCGGGCGCGGCGACAGCGA |
| 183 | miR-205 | AAAGAUCCUCAGACAAUCCAUGUGCUUCUCUUGUCCUUCAUUCCACCGGAGUCUGUCUCAUACCCAACCAGAUUUCAGUGGAGUGAAGUUCAGGAGGCAUGGAGCUGACA |
| 184 | miR-20a | GUAGCACUAAAGUGCUUAUAGUGCAGGUAGUGUUUAGUUAUCUACUGCAUUAUGAGCACUUAAAGUACUGC |
| 185 | miR-21 | UGUCGGGUAGCUUAUCAGACUGAUGUUGACUGUUGAAUCUCAUGGCAACACCAGUCGAUGGGCUGUCUGACA |
| 186 | miR-210 | ACCCGGCAGUGCCUCCAGGCGCAGGGCAGCCCCUGCCCACCGCACACUGCGCUGCCCCAGACCCACUGUGCGUGUGACAGCGGCUGAUCUGUGCCUGGGCAGCGCGACCC |
| 187 | miR-216a | GAUGGCUGUGAGUUGGCUUAAUCUCAGCUGGCAACUGUGAGAUGUUCAUACAAUCCCUCACAGUGGUCUCUGGGAUUAUGCUAAACAGAGCAAUUUCCUAGCCCUCACGA |
| 188 | miR-218-1 | GUGAUAAUGUAGCGAGAUUUUCUGUUGUGCUUGAUCUAACCAUGUGGUUGCGAGGUAUGAGUAAAACAUGGUUCCGUCAAGCACCAUGGAACGUCACGCAGCUUUCUACA |
| 189 | miR-218-2 | GACCAGUCGCUGCGGGGCUUUCCUUUGUGCUUGAUCUAACCAUGUGGUGGAACGAUGGAAACGGAACAUGGUUCUGUCAAGCACCGCGGAAAGCACCGUGCUCUCCUGCA |
| 190 | miR-22 | GGCUAGCCGCAGUAGUUCUUCAGUGGCAAGCUUUAUGUCCUGACCCAGCUAAAAGCUGCCAGUUGAAGAACUGUUGCCCUCUGCC |
| 191 | miR-221 | UGAACAUCCAGGUCUGGGGCAUGAACCUGGCAUACAAUGUAGAUUUCUGUGUUCGUUAGGCAACAGCUACAUUGUCUGCUGGGUUUCAGGCUACCUGGAAACAUGUUCUC |
| 192 | miR-222 | GCUGCUGGAAGGUGUAGGUACCCUCAAUGGCUCAGUAGCCAGUGUAGAUCCUGUCUUUCGUAAUCAGCAGCUACAUCUGGCUACUGGGUCUCUGAUGGCAUCUUCUAGCU |

Figure 1E

| 193 | miR-223 | CCUGGCCUCCUGCAGUGCCACGCUCCGUGUAUUUGACAAGCUGAGUUGGACACUCCAUGUGGUAGAGUGUCAGUUUGUCAAAUACCCCAAGUGCGGCACAUGCUUACCAG |
| --- | --- | --- |
| 194 | miR-224 | GGGCUUUCAAGUCACUAGUGGUUCCGUUUAGUAGAUGAUUGUGCAUUGUUUCAAAAUGGUGCCCUAGUGACUACAAAGCCC |
| 195 | miR-23a | GGCCGGCUGGGGUUCCUGGGGAUGGGAUUUGCUUCCUGUCACAAAUCACAUUGCCAGGGAUUUCCAACCGACC |
| 196 | miR-23b | CUCAGGUGCUCUGGCUGCUUGGGUUCCUGGCAUGCUGAUUUGUGACUUAAGAUUAAAAUCACAUUGCCAGGGAUUACCACGCAACCACGACCUUGGC |
| 197 | miR-24-1 | CUCCGGUGCCUACUGAGCUGAUAUCAGUUCUCAUUUUACACACUGGCUCAGUUCAGCAGGAACAGGAG |
| 198 | miR-24-2 | CUCUGCCUCCCGUGCCUACUGAGCUGAAACACAGUUGGUUUGUGUACACUGGCUCAGUUCAGCAGGAACAGGG |
| 199 | miR-25 | GGCCAGUGUUGAGAGGCGGAGACUUGGGCAAUUGCUGGACGCUGCCCUGGGCAUUGCACUUGUCUCGGUCUGACAGUGCCGGCC |
| 200 | miR-26a-1 | GUGGCCUCGUUCAAGUAAUCCAGGAUAGGCUGUGCAGGUCCCAAUGGGCCUAUUCUUGGUUACUUGCACGGGGACGC |
| 201 | miR-26a-2 | GGCUGUGGCUGGAUUCAAGUAAUCCAGGAUAGGCUGUUUCCAUCUGUGAGGCCUAUUCUUGAUUACUUGUUUCUGGAGGCAGCU |
| 202 | miR-26b | CCGGGACCCAGUUCAAGUAAUUCAGGAUAGGUUGUGUGCUGUCCAGCCUGUUCUCCAUUACUUGGCUCGGGGACCGG |
| 203 | miR-27a | CUGAGGAGCAGGGCUUAGCUGCUUGUGAGCAGGGUCCACACCAAGUCGUGUUCACAGUGGCUAAGUUCCGCCCCCCAG |
| 204 | miR-27b | ACCUCUCUAACAAGGUGCAGAGCUUAGCUGAUUGGUGAACAGUGAUUGGUUUCCGCUUUGUUCACAGUGGCUAAGUUCUGCACCUGAAGAGAAGGUG |
| 205 | miR-29a | AUGACUGAUUUCUUUUGGUGUUCAGAGUCAAUAUAAUUUUCUAGCACCAUCUGAAAUCGGUUAU |
| 206 | miR-29b-2 | CUUCUGGAAGCUGGUUUCACAUGGUGGCUUAGAUUUUUCCAUCUUUGUAUCUAGCACCAUUUGAAAUCAGUGUUUUAGGAG |
| 207 | miR-296 | AGGACCCUUCCAGAGGGCCCCCCCUCAAUCCUGUUGUGCCUAAUUCAGAGGGUUGGGUGGAGGCUCUCCUGAAGGGCUCU |
| 208 | miR-301a | ACUGCUAACGAAUGCUCUGACUUUAUUGCACUACUGUACUUUACAGCUAGCAGUGCAAUAGUAUUGUCAAAGCAUCUGAAAGCAGG |
| 209 | miR-302a | CCACCACUUAAACGUGGAUGUACUUGCUUUGAAACUAAAGAAGUAAGUGCUUCCAUGUUUUGGUGAUGG |
| 210 | miR-30a | GCGACUGUAAACAUCCUCGACUGGAAGCUGUGAAGCCACAGAUGGGCUUUCAGUCGGAUGUUUGCAGCUGC |
| 211 | miR-30b | ACCAAGUUUCAGUUCAUGUAAACAUCCUACACUCAGCUGUAAUACAUGGAUUGGCUGGGAGGUGGAUGUUUACUUCAGCUGACUUGGA |
| 212 | miR-30c-1 | ACCAUGCUGUAGUGUGUGUAAACAUCCUACACUCUCAGCUGUGAGCUCAAGGUGGCUGGGAGAGGGUUGUUUACUCCUUCUGCCAUGGA |
| 213 | miR-30c-2 | AGAUACUGUAAACAUCCUACACUCUCAGCUGUGGAAAGUAAGAAAGCUGGGAGAAGGCUGUUUACUCUUUCU |
| 214 | miR-30d | GUUGUUGUAAACAUCCCCGACUGGAAGCUGUAAGACACAGCUAAGCUUUCAGUCAGAUGUUUGCUGCUAC |
| 215 | miR-30e | GGGCAGUCUUUGCUACUGUAAACAUCCUUGACUGGAAGCUGUAAGGUGUUCAGAGGAGCUUUCAGUCGGAUGUUUACAGCGGCAGGCUGCCA |
| 216 | miR-31 | GGAGAGGAGGCAAGAUGCUGGCAUAGCUGUUGAACUGGGAACCUGCUAUGCCAACAUAUUGCCAUCUUUCC |

Figure 1F

| | | |
|---|---|---|
| 217 | miR-320 | GCUUCGCUCCCCUCCGCCUUCUCUUCCCGGUUCUUCCCGGAGUCGGGAAAAGCUGGGUUGAGAGGGCGAAAAAGGAUGAGGU |
| 218 | miR-323 | UUGGUACUUGGAGAGAGGUGGUCCGUGGCGCGUUCGCUUUAUUUAUGGCGCACAUUACACGGUCGACCUCUUUGCAGUAUCUAAUC |
| 219 | miR-324 | CUGACUAUGCCUCCCCGCAUCCCCUAGGGCAUUGGUGUAAAGCUGGAGACCCACUGCCCCAGGUGCUGCUGGGGGUUGUAGUC |
| 220 | miR-326 | CUCAUCUGUCUGUUGGGCUGGAGGCAGGGCCUUUGUGAAGGCGGGUGGUGCUCAGAUCGCCUCUGGGCCCUUCCUCCAGCCCCGAGGCGGAUUCA |
| 221 | miR-330 | CUUUGGCGAUCACUGCCUCUCUGGGCCUGUGUCUUAGGCUCUGCAAGAUCAACCGAGCAAAGCACACGGCCUGCAGAGAGGCAGCGCUCUGCCC |
| 222 | miR-331 | GAGUUUGGUUUUGUUUGGGUUUGUUCUAGGUAUGGUCCCAGGGAUCCCAGAUCAAACCAGGCCCCUGGGCCUAUCCUAGAACCAACCUAAGCUC |
| 223 | miR-335 | UGUUUUGAGCGGGGGUCAAGAGCAAUAACGAAAAAUGUUUGUCAUAAACCGUUUUUCAUUAUUGCUCCUGACCUCCUCUCAUUUGCUAUAUUCA |
| 224 | miR-346 | GGUCUCUGUGUUGGGCGUCUGUCUGCCCGCAUGCCUGCCUCUCUGUUGCUCUGAAGGAGGCAGGGGCUGGGCCUGCAGCUGCCUGGGCAGAGCGG |
| 225 | miR-34a | GGCCAGCUGUGAGUGUUUCUUUGGCAGUGUCUUAGCUGGUUGUUGUGAGCAAUAGUAAGGAAGCAAUCAGCAAGUAUACUGCCCUAGAAGUGCUGCACGUUGUGGGGCCC |
| 226 | miR-370 | AGACAGAGAAGCCAGGUCACGUCUCUGCAGUUACACAGCUCACGAGUGCCUGCUGGGGUGGAACCUGGUCUGUCU |
| 227 | miR-372 | GUGGGCCUCAAAUGUGGAGCACUAUUCUGAUGUCCAAGUGGAAAGUGCUGCGACAUUUGAGCGUCAC |
| 228 | miR-373 | GGGAUACUCAAAAUGGGGGCGCUUUCCUUUUUGUCUGUACUGGGAAGUGCUUCGAUUUUGGGGUGUCCC |
| 229 | miR-497 | CCACCCCGGUCCUGCUCCCGCCCCAGCAGCACACUGUGGUUUGUACGGCACUGUGGCCACGUCCAAACCACACUGUGGUGUUAGAGCGAGGGUGGGGGAGGCACCGCCGAGG |
| 230 | miR-498 | AACCCUCCUUGGGAAGUGAAGCUCAGGCUGUGAUUUCAAGCCAGGGGGCGUUUUUCUAUAACUGGAUGAAAAGCACCUCCAGAGCUUGAAGCUCACAGUUUGAGAGCAAUCGUCUAAGGAAGUU |
| 231 | miR-503 | UGCCCUAGCAGCGGGAACAGUUCUGCAGUGAGCGAUCGGUGCUCUGGGGUAUUGUUUCCGCUGCCAGGGUA |
| 232 | miR-92-1 | CUUUCUACACAGGUUGGGAUCGGUUGCAAUGCUGUGUUUCUGUAUGGUAUUGCACUUGUCCCGGCCUGUUGAGUUUGG |
| 233 | miR-92-2 | UCAUCCCUGGGUGGGGAUUUGUUGCAUUACUUGUGUUCUAUAUAAAGUAUUGCACUUGUCCCGGCCUGUGGAAGA |
| 234 | miR-93 | CUGGGGGCUCCAAAGUGCUGUUCGUGCAGGUAGUGUGAUUACCCAACCUACUGCUGAGCUAGCACUUCCCGAGCCCCGG |
| 235 | miR-96 | UGGCCGAUUUUGGCACUAGCACAUUUUUGCUUGUGUCUCUCCGCUCUGAGCAAUCAUGUGCAGUGCCAAUAUGGGAAA |
| 236 | miR-99a | CCCAUUGGCAUAAACCCGUAGAUCCGAUCUUGUGGUGAAGUGGACCGCACAAGCUCGCUUCUAUGGGUCUGUGUCAGUGUG |

METHODS OF NORMALIZATION IN MICRORNA DETECTION ASSAYS

MicroRNAs (miRNAs) are small, regulatory RNA molecules that influence gene expression by binding to mRNAs. Found in both plants and animals, these approximately 18 to 25-mer RNAs originate as transcripts with hairpin loops, and sometimes appear in clustered loci in the genome. In the nucleus, the ribonuclease Drosha cleaves the primary transcript clusters to form pre-miRNAs, which are exported to the cytoplasm and further processed by the RNase Dicer. One strand of the resulting double-stranded miRNA is the mature miRNA, and can regulate mRNA target transcription by interacting with the RNA-induced silencing complex (RISC). Target mRNAs may contain multiple miRNA binding sites, which allows very fine tuning of gene expression at the mRNA level.

Over the last several years, evidence has emerged regarding the regulatory role of miRNAs in many biological processes including development, viral infection, and cancer (Weimer E., *European Journal of Cancer* 43:1529-1544 (2007)). In particular, many tumor cells have distinct miRNA expression patterns compared to normal tissues. Some miRNAs appear to act as oncogenes or tumor repressors. When these miRNAs are deleted or inappropriately expressed, cells lose one mechanism to control tumor development. Because miRNA expression changes can have profound effects on normal and disease processes, these molecules have potential use in clinical diagnostic applications. In particular, there is a need for a rapid and sensitive test for quantifying miRNAs in biological samples. In cases where the over- or under-expression of specific miRNAs are known to correlate with disease state, such a test may enable an efficient and accurate diagnosis in a clinical setting.

Several nucleic acid assay technologies have been used to identify and characterize miRNAs, such as microarray and quantitative real-time reverse transcriptase polymerase chain reaction (qRT-PCR) assays. These methods are often used in attempts to identify changes in expression profile between tissue types, or to quantify known targets in various samples (Szafranzka et al., *Oncogene* 26:4442-4452 (2007); Mattie et al., *Molecular Cancer* 5:24 (2006); Bandres et al., Molecular Cancer 5:29 (2006); Cummins et al., *Proc. Natl. Acad. Sci.* 103:3687-3692 (2006); Zhang et al., *Proc. Natl. Acad. Sci.* 103:9136-9141 (2006)). For a clinical diagnostic test, the ability to rapidly quantify one or several known targets with minimal user intervention can be important. q-PCR is an especially powerful tool, given its extraordinary sensitivity, high specificity, and ability to detect nucleic acids over a wide dynamic range. This technique is known to provide definitive quantitation of miRNA expression in a single reaction container.

Since miRNA levels can vary because of sample variability, results from quantification assays should be normalized against an endogenous control. Although accurate normalization is an important aspect of nearly every gene expression assay, it may be of critical importance in the case of miRNA, as even slight changes in miRNA levels may exert significant biological effects (Calin et al., *Cancer Res.* 66:7390-7394 (2006)). Quantifying these differences with accuracy will be important for clinical diagnostics using miRNA analytes.

A single-tube multiplex miRNA detection assay is useful to rapidly measure the amount of a miRNA, for example in a diagnostic assay. However, accurate quantification of an miRNA in a multiplex assay presents unique challenges. Precise normalization allows correction for inter-sample variability and accurate quantification. Samples are commonly normalized by comparison to a panel of control miRNAs in microarray assays that quantify miRNAs, as a microarray can detect up to hundreds or thousands of discrete sequences. In contrast, a single-tube multiplex qRT-PCR reaction, for example, detects only a few nucleic acid sequences. There is not sufficient optical bandwidth in such a single-tube multiplex assay to increase normalization accuracy by measuring a large number of internal control sequences. Thus, in a single-tube multiplex miRNA detection assay, accurate quantification may require accurate normalization based on detection of only one or a few normalizer sequences.

We herein describe multiplex methods for rapidly and accurately quantifying miRNAs using endogenous miRNA normalizers.

The disclosures in this application relate to methods for normalizing miRNA quantification data in a biological sample. In one embodiment, steps for quantifying the amount of a target miRNA in a biological sample include (a) measuring the amount of the target miRNA in the sample in a reaction volume, (b) measuring the amount of at least one reference oncomir in the reaction volume, and (c) normalizing the target miRNA measurement based on the amount of at least one oncomir. In another embodiment, the method includes measuring the amount of a first and a second reference oncomir in the biological sample and normalizing the target miRNA levels to the first and second oncomirs. Further embodiments include amplifying the target miRNA and at least one reference oncomir in the reaction volume. In certain embodiments the amplification includes real-time polymerase chain reaction (q-PCR) amplification.

In some embodiments, the reference oncomir is chosen from hsa-miR-191, hsa-miR-93, hsa-miR-106a, hsa-miR-25, hsa-miR-17-5p, hsa-miR-103, hsa-miR-24, hsa-miR-99a, hsa-miR-320, hsa-miR-23a, hsa-miR-125a, hsa-miR-27a, hsa-miR-146a, and hsa-miR-195. Particular embodiments of the described quantification methods include measuring the amount of miR-191.

In some methods, the step of measuring the amount of at least one reference oncomir consists of measuring a first and a second reference oncomir. In certain embodiments the first and second oncomir are each chosen from hsa-miR-191, hsa-miR-93, hsa-miR-106a, hsa-miR-25, hsa-miR-17-5p, hsa-miR-16, hsa-let-7a, hsa-miR-103, hsa-miR-24, hsa-miR-99a, hsa-miR-320, hsa-miR-23a, hsa-miR-125a, hsa-miR-27a, hsa-miR-146a, and hsa-miR-195. In other methods, the first and second reference oncomirs are a pair chosen from hsa-miR-191 and hsa-miR-93; hsa-miR-25 and hsa-miR-191; hsa-let-7a and hsa-miR-103; and hsa-miR-17-5p and hsa-miR-24. In other aspects, the step of measuring the amount of at least one reference oncomir consists of measuring a reference oncomir chosen from hsa-miR-191, hsa-miR-93, hsa-miR-106a, hsa-miR-25, hsa-miR-17-5p, hsa-miR-103, hsa-miR-24, hsa-miR-99a, hsa-miR-320, hsa-miR-23a, hsa-miR-125a, hsa-miR-27a, hsa-miR-146a, and hsa-miR-195.

In some embodiments, steps for quantifying the amount of a target miRNA comprise: (a) measuring the amount of the target miRNA in the sample; (b) measuring the amount of at least one reference oncomir chosen from let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a in the sample; and (c) normalizing the target miRNA measurement based on the amount of at least one reference oncomir.

Some aspects of the described methods include normalizing the amount of a target miRNA in a biological sample by measuring the amount of the target miRNA and the amount of a first reference oncomir in the sample in a single reaction volume and normalizing the target miRNA measurement based on the amount of the reference oncomir in the sample. Further aspects include measuring the amount of a second reference oncomir in the biological sample and normalizing the target miRNA level to the first and second oncomirs. Some embodiments further include amplifying the target miRNA and the first reference oncomir in the reaction volume. In certain embodiments, the first and second reference oncomirs are chosen from hsa-miR-191, hsa-miR-93, hsa-miR-106a, hsa-miR-25, hsa-miR-17-5p, hsa-miR-16, hsa-let-7a, hsa-miR-103, hsa-miR-24, hsa-miR-99a, hsa-miR-320, hsa-miR-23a, hsa-miR-125a, hsa-miR-27a, hsa-miR-146a, and hsa-miR-195.

Some embodiments include methods for quantifying the relative expression of a target miRNA in biological samples, comprising (a) measuring the amount of the target miRNA sequence and a first reference oncomir sequence in a first biological sample in a first reaction volume, (b) measuring the amount of the target miRNA sequence and the first reference oncomir sequence in a second biological sample in a second reaction volume, and (c) normalizing the target miRNA level to the reference oncomir level for the first and second samples, thereby quantifying the relative expression of the target miRNA. Some methods for quantifying the relative expression of a target miRNA in biological samples further include amplifying the target miRNA and the first reference oncomir in the first reaction volume and amplifying the target miRNA and the second reference oncomir in the second reaction volume.

Other embodiments of the invention are discussed throughout this application. Other objects, features, and advantages of the present invention will become apparent from the following detailed description. Any embodiment discussed with respect to one aspect of the invention applies to other aspects of the invention as well and vice versa. The embodiments in the Example section are understood to be embodiments of the invention that are applicable to all aspects of the invention.

It should be understood, however, that the detailed description and the specific examples, while indicating specific embodiments of the invention, are given by way of illustration only, since various changes and modifications within the spirit and scope of the invention will become apparent to those skilled in the art from this detailed description.

Additional aspects of the invention will be set forth in the description that follows.

BRIEF DESCRIPTION OF THE DRAWINGS

FIG. 1, parts A through F, lists human miRNA sequences which are differentially expressed in cancer. SEQ ID NOs: 1-114 are mature miRNAs, and SEQ ID NOs: 115-236 are precursor sequences.

EXEMPLARY EMBODIMENTS

Figure 2:
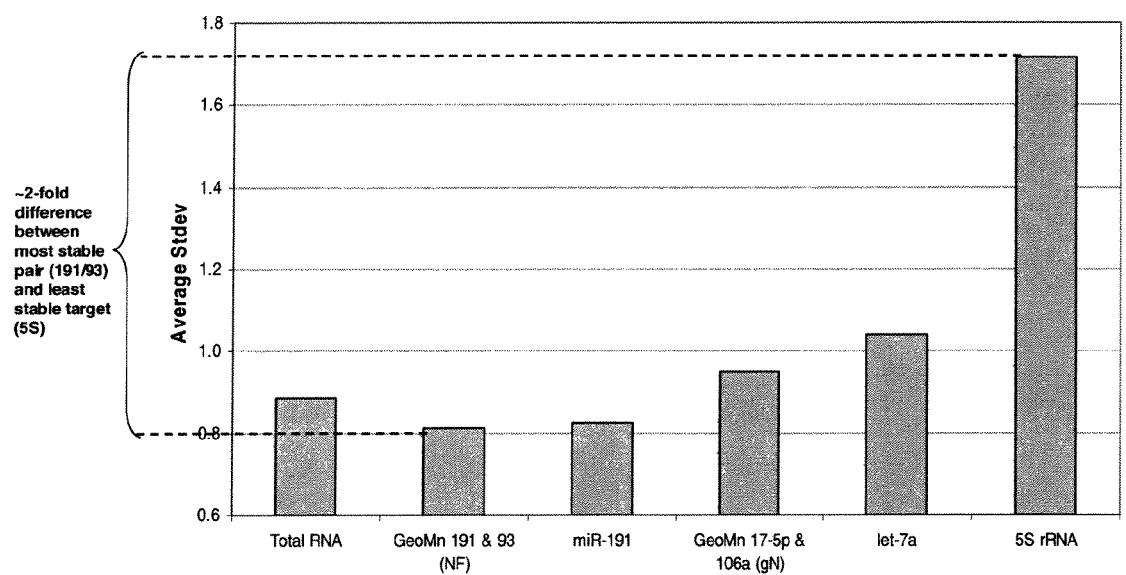
FIG. 2 is a graph representing the average standard deviation of normalized qRT-PCR results of miRNAs listed in Table 1. The x-axis indicates the normalizer(s) used, and the y-axis shows the resulting average standard deviation across the various tissue samples of Example 1. Where more than one miRNA normalizer is used, the data is normalized to the geometric mean (GeoMn) of the miRNA normalizers. The miRNA pair hsa-miR-191 and hsa-miR-93 represents the most stable pair as determined by NormFinder (NF), and the pair hsa-miR-17-5p and hsa-miR-106a represents the most stable pair identified by geNorm (gN).

In certain aspects, the methods of the invention provide multiplex detection assays for quantifying the amount of a target miRNA in a biological sample by normalizing the amount of the target miRNA to the amount a stably expressed miRNA called a reference oncomir. The inventors have surprisingly discovered that a subset of miRNAs that are differentially expressed in cancer are more accurate as normalizers in miRNA quantification assays than currently used internal control normalizers. In clinical diagnostic applications, the ability to reliably detect small changes in miRNA expression can have a significant impact. Furthermore, in order to develop miRNA therapeutics, monitoring in vivo effects will require accurate methods of measuring miRNA levels. The methods described herein will allow for more accurate quantification of miRNAs, thus facilitating the development of miRNA diagnostics and therapeutics.

To assist in understanding the present invention, certain terms are first defined. Additional definitions are provided throughout the application.

As used herein, the term "microRNA" (miRNA) includes human miRNAs, mature single stranded miRNAs, precursor miRNAs, and variants thereof, which may be naturally occurring or synthetic. Synthetic or naturally occurring miRNAs may be modified to include chemical groups other than hydroxy or phosphate at their 5' termini, sugar, and/or base modifications. In some instances the term "miRNA" also includes primary miRNA transcripts and duplex miRNAs. The term includes target miRNAs, oncomirs, and reference oncomirs (see below). The term "mature," when modifying miRNA or a specific miRNA such as miR-103, refers to the mature sequence(s) processed from the corresponding pre-miRNA sequence that are present in a biological sample. The sequences for particular miRNAs, including human mature and precursor sequences, are reported in the miRBase::Sequences Database (http:/microrna.sanger.ac.uk; Griffiths-Jones et al., *Nucleic Acids Research,* 2006, 34, Database Issue, D140-D144; Griffiths-Jones, *Nucleic Acids Research,* 2004, 32, Database Issue, D109-D111). The skilled artisan will appreciate that scientific consensus regarding the precise nucleic acid sequence for a given miRNA, in particular for mature forms of the miRNAs, may change with time. MiRNAs detected by assays of this application include naturally occurring sequences for the miRNAs.

The term "target miRNA" refers to any miRNA of interest.

An "oncomir" is a microRNA that is differentially expressed in at least one cancer or tumor-derived cell type. "Oncomir" includes, but is not limited to miRNA such as: let-7a, let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-16, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a, and may be up- or down-regulated in cancer cells. Reference to specific nucleic acid sequences for the reference oncomirs is made in FIG. 1 and the sequence listing of this application.

The term "reference oncomir" means a microRNA that is differentially expressed in at least one cancer, but shows a small variation in expression levels across a representative number of control and pathological samples, in that the reference oncomir is more stably expressed than 5S ribosomal RNA. As used herein, a reference oncomir is chosen from let-7a, let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-16, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a. In a preferred embodiment, a reference oncomir is chosen from let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a.

The use of the word "a", "an" or "the" when used in conjunction with the term "comprising" in the claims and/or the specification may mean "one," but it is also consistent with the meaning of "one or more," "at least one," and "one or more than one."

I. Methods to Determine the Amount of a miRNA

Many methods of quantifying miRNAs are contemplated. Any reliable, sensitive, and specific method can be used. In some embodiments provided, a target miRNA or reference oncomir is amplified prior to or during quantification. In other embodiments, the miRNA is not amplified as part of the quantification process.

A. Amplification Reactions

Many methods exist for amplifying miRNA nucleic acid sequences such as mature miRNAs, precursor miRNAs, and primary miRNAs. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method is used, such as reverse transcription followed by real time PCR (Chen et al., *Nucleic Acids Research,* 33(20):e179 (2005)).

A typical PCR reaction includes multiple amplification steps, or cycles that selectively amplify target nucleic acid species. A typical PCR reaction includes three steps: a denaturing step in which a target nucleic acid is denatured; an annealing step in which a set of PCR primers (forward and reverse primers) anneal to complementary DNA strands; and an elongation step in which a thermostable DNA polymerase elongates the primers. By repeating these steps multiple times, a DNA fragment is amplified to produce an amplicon, corresponding to the target DNA sequence. Typical PCR reactions include 20 or more cycles of denaturation, annealing, and elongation. In many cases, the annealing and elongation steps can be performed concurrently, in which case the cycle contains only two steps. Since mature miRNAs are single-stranded, a reverse transcription reaction (which produces a complementary cDNA sequence) is performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30, or 35 nucleotides in length. In additional embodiments, a primer is at least 35 nucleotides in length.

In a further aspect, a forward primer can comprise at least one sequence that anneals to a target miRNA and alternatively can comprise an additional 5' non-complementary region. In another aspect, a reverse primer can be designed to anneal to the complement of a reverse transcribed miRNA. The reverse primer may be independent of the target miRNA or reference oncomir sequence, and multiple target miRNAs or reference oncomirs may be amplified using the same reverse primer. Alternatively, a reverse primer may be specific for a target miRNA.

In some embodiments, two or more miRNAs are amplified in a single reaction volume (one or more target miRNAs and one, two, three, or more reference oncomirs, for example). Normalization may alternatively be performed in separate reaction volumes. One aspect includes multiplex q-PCR, such as qRT-PCR, which enables simultaneous amplification and quantification of at least one miRNA of interest and at least one reference oncomir in one reaction volume by using more than one pair of primers and/or more than one probe. The primer pairs comprise at least one amplification primer that uniquely binds each miRNA, and the probes are labeled such that they are distinguishable from one another, thus allowing simultaneous quantification of multiple miRNAs. Multiplex qRT-PCR has research and diagnostic uses, including but not limited to detection of miRNAs for diagnostic, prognostic, and therapeutic applications.

A single combined reaction for q-PCR, is desirable for several reasons: (1) decreased risk of experimenter error, (2) reduction in assay-to-assay variability, (3) decreased risk of target or product contamination, and (4) increased assay speed. The qRT-PCR reaction may further be combined with the reverse transcription reaction by including both a reverse transcriptase and a DNA-based thermostable DNA polymerase. When two polymerases are used, a "hot start" approach may be used to maximize assay performance (U.S. Pat. Nos. 5,411,876 and 5,985,619). For example, the components for a reverse transcriptase reaction and a PCR reaction may be sequestered using one or more thermoactivation methods or chemical alteration to improve polymerization efficiency (U.S. Pat. Nos. 5,550,044, 5,413,924, and 6,403,341).

B. Detection of miRNAs

In certain embodiments, labels, dyes, or labeled probes and/or primers are used to detect amplified or unamplified miRNAs. Depending on the sensitivity of the detection method and the abundance of the target, for example, amplification may or may not be required prior to detection. One skilled in the art will recognize the detection methods where miRNA amplification is preferred.

A probe or primer may include Watson-Crick bases or modified bases. Modified bases include, but are not limited to, the AEGIS bases (from Eragen Biosciences), which have been described, e.g., in U.S. Pat. Nos. 5,432,272, 5,965,364, and 6,001,983. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in a multiplex amplification are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan™) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,485,901 and 6,649,349), peptide nucleic acid (PNA) Molecular Beacons (see, e.g., U.S. Pat. Nos. 6,355,421 and 6,593,091), linear PNA beacons (see, e.g. U.S. Pat. No. 6,329,144), non-FRET probes (see, e.g., U.S. Pat. No. 6,150,097), Sunrise™/AmplifluorB™probes (see, e.g., U.S. Pat. No. 6,548,250), stem-loop and duplex Scorpion™ probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse™ probe (Epoch Biosciences), hairpin probes (see, e.g., U.S. Pat. No. 6,596,490), PNA light-up probes, antiprimer quench probes (Li et al., *Clin. Chem.* 53:624-633 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

MiRNAs can be detected by direct or indirect methods. In a direct detection method, one or more miRNAs are detected by a detectable label that is linked to a nucleic acid molecule. In such methods, the miRNAs may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miRNAs, are detected using FlexMAP Microspheres (Luminex) conjugated with probes to capture the desired nucleic acids. Some methods may involve detection with polynucleotide probes modified with fluorescent labels or branched DNA (bDNA) detection, for example.

In other embodiments, nucleic acids are detected by indirect detection methods. In such an embodiment, a biotinylated probe is combined with a stretavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises Phycolink® Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal (see, e.g., Kricka, L., Nonisotopic DNA Probe Techniquies, Academic Press, San Diego (1992) and Garman A., Non-Radioactive Labeling, Academic Press (1997).). Fluorescent reporter dyes useful as labels include, but are not limited to, fluoresceins (see, e.g., U.S. Pat. Nos. 5,188,934, 6,008,379, and 6,020,481), rhodamines (see, e.g., U.S. Pat. Nos. 5,366,860, 5,847,162, 5,936,087, 6,051,719, and 6,191,278), benzophenoxazines (see, e.g., U.S. Pat. No. 6,140,500), energy-transfer fluorescent dyes, comprising pairs of donors and acceptors (see, e.g., U.S. Pat. Nos. 5,863,727; 5,800,996; and 5,945,526), and cyanines (see, e.g., WO 9745539), lissamine, phycoerythrin, Cy2, Cy3, Cy3.5, Cy5, Cy5.5, Cy7, FluorX (Amersham), Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, Tetramethylrhodamine, and/or Texas Red, as well as any other fluorescent moiety capable of generating a detectable signal. Examples of fluorescein dyes include, but are not limited to, 6-carboxyfluorescein; 2',4',1,4,-tetrachlorofluorescein; and 2',4',5',7',1, 4-hexachlorofluorescein. In certain aspects, the fluorescent label is selected from SYBR-Green, 6-carboxyfluorescein ("FAM"), TET, ROX, VIC™, and JOE. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In still a further aspect, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in *Nucleic Acids in Chemistry and Biology* (1996)).

In further aspects, methods relying on hybridization and/or ligation to quantify miRNAs may be used, including oligonucleotide ligation (OLA) methods and methods that allow a distinguishable probe that hybridizes to the target nucleic acid sequence to be separated from an unbound probe. As an example, HARP-like probes, as disclosed in U.S. Publication No. 2006/0078894 (incorporated herein by reference) may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding the unhybridized HARP probe. The agent is able to inactivate or modify unhybridized HARP probe such that it cannot be amplified.

In an additional embodiment of the method, a probe ligation reaction may be used to quantify miRNAs. In a Multiplex Ligation-dependent Probe Amplification (MLPA) technique (Schouten et al., *Nucleic Acids Research* 30:e57 (2002)) pairs of probes which hybridize immediately adjacent to each other on the target nucleic acid are ligated to each other only in the presence of the target nucleic acid. In some aspects, MLPA probes have flanking PCR primer binding sites. MLPA probes can only be amplified if they have been ligated, thus allowing for detection and quantification of target miRNA or reference oncomir.

II. Normalization

To use a miRNA quantification assay as a clinically relevant diagnostic tool, normalization to the appropriate control is important. Methods of normalization and kits for normalizing miRNA detection assays are provided herein. The methods correct for sample-to-sample variability by comparing a target measurement in a sample to one or more internal controls. Normalization of miRNA quantification assays reduces systematic (non-biological) and non-systematic differences between samples, and is critical for accurate measurement of differential miRNA expression, for example.

The accurate measurement of biologically hardwired differential expression between two groups of samples is the goal of many miRNA qRT-PCR assays. Yet, miRNA levels in qRT-PCR reactions can vary from one sample to the next for reasons that may be technical or biological. Technical reasons may include variabilities in tissue procurement or storage, inconsistencies in RNA extraction or quantification, or differences in the efficiency of the reverse transcription and/or PCR steps. Biological reasons may include sample-to-sample heterogeneity in cellular populations, differences in bulk transcriptional activity, or alterations in specific miRNA expression that is linked to an aberrant biological program (e.g., a disease state). Given the multiplicity of sources that can contribute to differences in miRNA quantification, results from qRT-PCR assays should be normalized against a relevant endogenous target or targets to minimize controllable variation, and permit definitive interpretations of nominal differences in miRNA expression.

Certain embodiments comprise multiplex methods for quantifying and normalizing the amount of target miRNA in a biological sample. In accordance with one aspect of the invention, the amount of one or more target miRNAs is measured in a reaction volume, and the amount of at least one reference oncomir is measured in the reaction volume. The amount of target miRNA is normalized based on the amount of at least one oncomir. In some embodiments of the invention, the target miRNA measurement(s) are normalized to the measurement of one reference oncomir. One, two, or three reference oncomirs are measured in some embodiments. In other embodiments, the one or more target miRNA measurements are normalized to the measurement of two, three, four, five, six, seven, eight, nine, ten, or more reference oncomirs. For example, Luminex technology allows for detection of as many as 100 unique analytes in one sample. As such, a much larger number of normalizers can potentially be exploited in Luminex miRNA assays. Indeed, the FlexMir assay includes 4 snoRNAs as controls for signal normalization. In additional embodiments, the relative expression of a target miRNA in two or more biological samples can be quantified and normalized to the amount of a reference oncomir.

For experiments using one reference oncomir, the data is normalized to the measured quantity of the oncomir. When two or more reference oncomirs are used as normalizers, a mean of the normalizers (e.g. arithmetic mean or geometric mean) is optionally used, depending on the nature of the quantification data. For example, the threshold cycle ($C_t$) values obtained from q-PCR experiments may be normalized to the geometric mean of two or more normalizers. Data represented on a linear scale (absolute expression data) may be normalized to an arithmetic mean of normalizers. Additional methods of combining normalizers are also contemplated, such as weighted averages.

In some embodiments, expression levels may be normalized using a comparative $C_t$ method for relative quantification between samples or sample types. The general methods for conducting such assays are described, e.g., in Real-Time PCR Systems: Applied Biosystems 7900HT Fast Real-Time PCR System, and 7300/7500 Real-Time PCR Systems, *Chemistry Guide*, Applied Biosystems, 2005, Part No. 4348358.

Many additional methods of normalization are well known to those skilled in the art, and all normalization methods are contemplated. Those skilled in the art will recognize the appropriate normalization methods for each quantification and detection method described herein.

III. Reference Oncomirs

Some embodiments of the invention include measuring the amount of at least one reference oncomir, and normalizing the amount of a target miRNA to the amount of at least one oncomir(s). Normalizers suitable for use in the claimed methods are differentially expressed in at least one cancer, but show a small variation in expression levels across a representative number of control and/or pathological samples. A reference oncomir is more stably expressed than 5S rRNA between the representative samples. For a clinical diagnostic assay, reference oncomirs are selected based on the source of the biological samples and the particular disease, condition, or potential condition of interest. For example, in a diagnostic assay for lung cancer, suitable reference oncomirs are those which are relatively stably expressed across normal and tumor lung tissue samples, and include hsa-miR-191, hsa-miR-125, hsa-miR-103, and the pairs of oncomirs hsa-let-7a and hsa-miR-103, and hsa-miR-17-5p and miR-24.

In some embodiments, normalizers are identified using the NormFinder (Andersen et al., *Cancer Res.* 64 (15):5245-5250 (2004)) or geNorm (Vandesompele et. al., *Genome Biol.* 3(7): research 0034.1-0034.11 (2002)) algorithms based on various qRT-PCR data from human cell and tissue collections. Additional statistical methods are known in the art for identifying stably expressed members of a group, and are also contemplated for use to identify miRNA normalizers. In certain aspects, normalizers are identified by using the NormFinder or geNorm algorithms to analyze data from normal and tumor tissue samples. There are many suitable reference samples that can be used to identify reference oncomirs.

Certain embodiments include measuring the amount of a target miRNA and a reference oncomir, and normalizing the target miRNA level to the oncomirs. Additional embodiments include measuring the amount of a first and a second reference oncomir, and normalizing the target miRNA level to the first and second oncomirs. Further embodiments include quantifying the relative expression of target miRNAs between biological samples by (a) measuring the amount of a target miRNA and a first reference oncomir in a first biological sample, (b) measuring the amount of a target miRNA sequence and the first reference oncomir in a second biological sample, and (c) normalizing the target miRNA level to the reference oncomir level for the first and second sample.

In some methods described herein, the one or more reference oncomir(s) is/are chosen from let-7a, let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-16, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, miR-99a. In certain methods, the one or more reference oncomir(s) is/are chosen from hsa-miR-191, hsa-miR-93, hsa-miR-106a, hsa-miR-25, hsa-miR-17-5p, hsa-miR-16, hsa-let-7a, hsa-miR-103, hsa-miR-24, hsa-miR-99a, hsa-miR-320, hsa-miR-23a, hsa-miR-125a, hsa-miR-27a, hsa-miR-146a, and hsa-miR-195. In further embodiments, the one or more reference oncomir(s) is/are chosen from hsa-miR-191, hsa-miR-93, hsa-miR-106a, hsa-miR-25, hsa-miR-17-5p, hsa-miR-103, hsa-miR-24, hsa-miR-99a, hsa-miR-320, hsa-miR-23a, hsa-miR-125a, hsa-miR-27a, hsa-miR-146a, and hsa-miR-195. In additional embodiments, the reference oncomir is hsa-miR-191 or hsa-miR-103. In other methods, two or three reference oncomirs may be used as normalizers. Suitable pairs of reference oncomirs may be identified using the NormFinder or geNorm algorithms, or using methods described in Szabo et al., *Genome Biol.*, 5(8): R59 (2004); Pfaffl M W, et al., Biotechnol. Lett., 26(6):509-15 (2004); Abruzzo L V et al., *Biotechniques,* 38(5):785-92 (2005); or Erickson H S et al., *Lab Invest.* 87(9):951-62 (2007). In some embodiments, two reference oncomirs are chosen from the pairs hsa-miR-191 and hsa-miR-93, hsamiR-25 and hsa-miR-191, hsa-let-7a and hsa-miR-103, and hsa-miR-17-5p and hsa-miR-24.

IV. Biological Samples

In the normalization methods provided herein, the amount of target miRNA in a biological sample is normalized to the amount of at least one reference oncomir in the biological sample.

A "biological sample" is any sample or specimen obtained from a human. For example, the biological sample may be a patient sample. A "patient sample" is any biological specimen from a patient. The term includes, but is not limited to, biological fluids such as blood, serum, plasma, urine, cerebrospinal fluid, tears, saliva, lymph, dialysis fluid, lavage fluid, semen, and other liquid samples, as well as cells and tissues of biological origin. The term also includes cells isolated from a human or cells derived therefrom, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. A biological sample may be obtained or derived from tissue types including but not limited to lung, liver, placenta, bladder, brain, heart, colon, thymus, ovary, adipose, stomach, prostate, uterus, skin, muscle, cartilage, breast, spleen, pancreas, kidney, eye, bone, intestine, esophagus, lymph nodes and glands. The term "biological sample" encompasses samples that have been manipulated in any way after their procurement, such as by treatment with preservatives, cellular disruption agents (e.g. lysing agents), solubilization, purification, or enrichment for certain components, such as polynucleotides, in certain aspects. Also, derivatives and fractions of patient samples are included. A sample may be obtained or derived from a patient having, suspected of having, or recovering from a disease or pathological condition. Diseases and pathological conditions include, but are not limited to, proliferative, inflammatory, immune, metabolic, infectious, and ischemic diseases. Diseases (e.g. cancers) also include neural, immune system, muscular, reproductive, gastrointestinal, pulmonary, cardiovascular, and renal diseases, disorders, and conditions.

V. Kits

The invention includes kits of reagents and macromolecules for carrying out the normalization assays provided herein. In one embodiment, the invention provides a kit for quantifying a target miRNA sequence and a reference oncomir sequence in a reaction volume. The kits include nucleic acid sequences that are identical or complementary to a portion of at least one target miRNA and at least one reference oncomir, for the detection of the target miRNA and the reference oncomir. In one aspect, the kits comprise at least one primer for the detection of a reference oncomir and a target miRNA. In another aspect, the kits comprise at least one probe specific to a reference oncomir and a target miRNA. The sequence-specific primers or probes are distinguishably labeled, allowing detection of at least one reference oncomir and at least one target miRNA in a single reaction volume.

The kits further optionally comprise an enzyme for carrying out the assays described herein, including but not limited to a polymerase such as a reverse transcriptase or a DNA polymerase, or a ligase. In certain aspects, the kits include nucleic acid molecules that are identical or complementary to a target miRNA and/or a reference oncomir. Such molecules may serve as absolute standards for creating standard curves to quantify the unknown levels of target in the sample of interest.

In various aspects, the kits may comprise multiple amplification primer sets, wherein at least one of the primers in each of the primer sets comprises a sequence that is complementary to a portion of at least two miRNAs, such as a target miRNA and a reference oncomir, or two reference oncomirs, for example. In other aspects, the kits further comprise at least two probes complementary to a portion of at least two miRNAs. The kit may also comprise reagents for reverse transcribing RNA to a DNA template and/or reagents, including primers, for amplification of the target DNA. Such a kit may include one or more buffers, such as a reaction, amplification, and/or a transcription buffer, compounds for preparing a RNA sample, for preparing a DNA sample, and components for isolating and/or detecting an amplification product, such as a probe or label, for example.

In some embodiments, kits of the invention include one or more of the following (consistent with methods, reagents, and compositions discussed above): components for sample purification, including a lysis buffer with a chaotropic agent; a glass-fiber filter or column; an elution buffer; a wash buffer; an alcohol solution; and a nuclease inhibitor. The components of the kits may be packaged either in aqueous media or in lyophilized form, for example, and will be provided in a suitable container. The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container. The kits of the present invention will also typically include a means for containing the RNA, and any other reagent containers in close confinement for commercial sale. Such containers may include injection or blow-molded plastic containers into which the desired vials are retained. When the components of the kit are provided in one and/or more liquid solutions, the liquid solution is an aqueous solution, with a sterile aqueous solution being particularly preferred.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

In a non-limiting example, reagents in a kit for reverse transcription and q-PCR of a target miRNA and a reference oncomir include reverse transcriptase, a reverse transcriptase primer, corresponding PCR primer sets, a thermostable DNA polymerase, and two distinguishable detection reagents which may include scorpion probes, probes for a fluorescent 5' nuclease assay, molecular beacon probes, single dye primers or fluorescent dyes specific to double-stranded DNA (e.g. ethidium bromide). The kit may also include multiple reverse transcriptase primers to one or more additional miRNAs, such as a target miRNA and/or a second reference oncomir. Additional materials may include a suitable reaction container, a barrier composition, reaction mixtures for reverse transcriptase and PCR stages (including buffers and reagents such as dNTPs), nuclease- or RNAse-free water, RNase inhibitor, and/or any additional buffers, compounds, co-factors, ionic constituents, proteins, enzymes, polymers, and the like that may be used in reverse transcriptase and/or PCR stages of the reactions.

VI. Diagnostic Methods

Methods to accurately determine an amount of a target miRNA sequence in a biological sample can be used in diagnostic applications.

In some embodiments, the methods described herein for determining the amount of a target miRNA sequence in a biological sample are used to diagnose and/or assess a disease, condition, or potential condition in a patient. In some embodiments, the amount of a target miRNA in the sample is indicative of the presence or absence of a disease, the disease progression, prognosis, or risk thereof.

In certain embodiments, the methods can be applied to quantify the relative expression (i.e. up-regulation or down-regulation) of certain target miRNA sequences in biological samples. Embodiments of the invention include methods for diagnosing and/or assessing a condition or potential condition in a patient comprising determining the amount of a target miRNA sequence and the amount of a reference oncomir in a sample from a patient, for example. The difference in the miRNA in the sample from a patient and the miRNA in a reference sample (e.g. a normal or non-pathologic sample), is indicative of a pathology, prognosis, disease, or cancerous condition, or risk thereof, for example. The invention may also be applied in methods to quantify miR-NAs that are indicative of infectious disease, such as a viral, fungal, or bacterial infection.

A "disease" is a pathological condition; for example, one that can be identified by symptoms or other identifying factors as diverging from a healthy or a normal state. The term "disease" includes disorders, syndromes, conditions, and injuries. Diseases include, but are not limited to, proliferative, inflammatory, immune, metabolic, infectious, and ischemic diseases. Diseases also include neural, immune system, muscular, reproductive, gastrointestinal, pulmonary, cardiovascular, renal, proliferative, and/or cancerous diseases.

It is specifically contemplated that the normalization methods described herein can be used in assays that evaluate differences between stages or progression of disease, such as between hyperplasia, neoplasia, pre-cancer, and cancer, or between a primary tumor and a metastasized tumor. Similarly, the normalization methods described herein are applicable to detect differential expression associated with various tissues, e.g. breast, blood, lymph, colon, liver, pancreatic, prostrate, and lung. Reference oncomir selection for a given diagnostic assay may be tailored to the tissue or disease based on expression information, and/or target miRNA of interest based on primer/probe design considerations.

As will be apparent to one of skill in the art, the normalization methods and kits described herein may be used to measure differential expression of miRNAs that are known to be associated with certain diseases. In the case of breast cancer, a target miRNA may be selected from human miR-NAs including but not limited to miR-10b, miR-21, miR-29b, miR-17-5p, miR-125b, miR-145, miR-146, and miR-155. For detection of malignant lymphoma, a target miRNA may be selected from human miRNAs including but not limited to miR-155, miR-17, miR-18a, miR-19a, miR-20a, miR-19b, and miR-92. In colorectal cancer, a target miRNA may be selected from human miRNAs including but not limited to the let-7 family, miR-10a, miR-20a, miR-24, miR-29b, miR-31, miR-96, miR-133b, miR-135b, miR-143, miR-145, miR-183, miR-17, miR-18a, miR-19a, miR-19b and miR-92. For hepatocellular carcinoma, the target miRNA may be selected from human miRNAs including but not limited to miR-18, miR-125a, miR-195, miR-199a, miR-200a, and miR-224. In cases of pancreatic cancer, the target miRNA may be selected from human miRNAs including but not limited to miR-21, miR-24, miR-100, miR-103, miR-107, miR-125b, and miR-155. For prostate cancer, the target miRNA may be selected from human miRNAs including but not limited to let-7d, miR-128a, miR-195, and miR-203. In cases of lung cancer, the target miRNA may be selected from human miRNAs including but not limited to the let-7 family, miR-17, miR-18a, miR-19a, miR-20a, miR-19b, miR-92, miR-21, miR-126*, miR-155, miR-200b, miR-205, and miR-210. See, e.g., Wiemer, *Eur. J Cancer* 43:1529-1544 (2007). These target and disease lists are solely exemplary, and not limiting on the claimed methods of normalization.

In a non-limiting example, a diagnostic assay for lung cancer may include measuring the amounts of target hsa-let-7a in FFPE lung tumor tissue and normal adjacent samples using reverse transcription and q-PCR, and normalizing the data using hsa-miR-17-5p and hsa-miR-24 as reference oncomirs. If the dd-$C_t$ values for the target miRNA exceeds a pre-determined cutoff value, the sample is determined to be positive.

EXAMPLES

The following examples illustrate various embodiments of the invention and are not intended to limit the scope of the invention.

The examples described herein include the use of q-PCR, which includes real-time monitoring of PCR products during the exponential phase instead of by an end-point measurement. The threshold cycle ($C_t$) measurements in the examples refer to the number of cycles it takes to reach a pre-defined point in the fluorescent signal.

Example 1

Identification of a Set of Reference Oncomirs Suitable for Normalization of miRNA Quantitative RT-PCR Results To identify appropriate reference oncomirs for the normalization of miRNA qRT-PCR results, FirstChoice® Total RNA samples were purchased (Ambion) which are certified to contain small RNAs (miRNA, siRNA, and snRNA) as well as large RNAs (rRNA, mRNA, and tRNA). These samples were used to generate both miRNA expression profiling and qRT-PCR data. RNA samples included 13 individual normal human tissue RNAs including placenta, bladder, brain, heart, lung, liver, colon, thymus, ovary, adipose, stomach, prostate, and uterus. A broad spectrum of solid tissues was included to test the hypothesis that an RNA or subset of RNA molecules might be stably expressed across different tissue types and thus would provide a superior reference set for normalization compared to the unvalidated reference RNAs that have been used as a default choice, such as ribosomal RNA and nuclear RNA. RNA concentrations were verified by measuring absorbance ($A_{260}$) on the NanoDrop Spectrophotometer ND-1000 (NanoDrop) and total RNA profiles were assessed on the Agilent 2100 bioanalyzer (Agilent Technologies) with equal mass loadings of 100 ng per sample onto the RNA 6000 Nano LabChip kit (Agilent Technologies). The 28S/18S ratio for all RNA samples was 1.1 to 1.8, as determined by the Eukaryote Total RNA Nano assay on the 2100 bioanalyzer expert software.

MicroRNA array expression profiling data for the 13 normal human tissues mentioned above were prepared and generated with the mitVana™ miRNA Bioarray V1 (Ambion) as described by Shingara et al., *RNA*, 11(9):1461-1470 (2005) with the raw signal data collected on the GenePix 4000B (Axon Instruments). Each array data set was normalized with the Global Normalized Signal approach, which is generated by computing the Variance Stabilization Normalization as described by Huber et al., *Bioinformatics*, 18 Suppl 1:S96-104 (2002). Using the normalized microarray data set, potential miRNA reference oncomirs were further standardized by a modified z-score ranking, indicating the number of standard deviations each miRNA is represented above or below the population mean ($\mu$). The modified z-score is described by the following equation, where $Z=(\chi-\mu)/\sigma$ and is determined by the population mean ($\mu$) subtracted from the mean array signal ($\chi$) across all tissue samples for a given miRNA then divided by the standard deviation ($\sigma$) of all tissue samples for a given miRNA. For the 13-sample array data set the mean array signals ($\chi$) for the top 40 targets resulting in modified z-score values >3.2, within an overall z-score range of 9.9 to –3.6, were chosen for geNorm (Vandesompele et. al.) and NormFinder (Andersen et. al.) analysis. To minimize the selection of false positives, miRNAs ranked by negative z-score values were excluded in this instance. Because miRNAs with low array expression results are unlikely to be detected by qRT-PCR within the desirable range of 15 to 35 amplification cycles, they are considered not to be stably expressed. Thus, two primary criteria were used for the selection of miRNA candidates for evaluation in qRT-PCR: 1) Stable expression across different samples (here, discrete solid tissues); and 2) Demonstrable, detectable levels of expression in the samples that would likely enable accurate RT-PCR quantification, e.g., high levels of expression.

Following modified z-score filtering, the mean array signal ($\chi$), represented on a sliding scale in the natural log space, for each normalization candidate was transformed to a quantity as outlined by the authors of geNorm and NormFinder. A list of potential reference oncomirs was ranked relative to a stability value (or modified z-score) as shown in Table 1. Although small nuclear U6 and ribosomal RNA 5S are not classified as miRNAs and there are no probes to detect these two small RNA species on the mirVana™ miRNA Bioarray, these sequences were included in this study due to their historical adoption as normalizers.

TABLE 1

Table of Array Stable miRNAs for the 13-Tissue Panel as Ranked by Modified Z-Score.

| | Potential Normalizer | Modified Z-score |
|---|---|---|
| | MicroRNA | |
| 1 | hsa-let-7a | 9.92 |
| 2 | hsa-miR-16 | 9.64 |
| 3 | hsa-miR-17-5p | 8.21 |
| 4 | hsa-miR-23a | 8.28 |
| 5 | hsa-miR-191 | 7.69 |
| 6 | hsa-miR-106a | 7.20 |
| 7 | hsa-miR-103 | 7.11 |
| 8 | hsa-miR-107 | 6.86 |
| 9 | hsa-miR-24 | 6.48 |
| 10 | hsa-miR-93 | 6.14 |
| 11 | hsa-miR-25 | 4.89 |
| 12 | hsa-miR-99a | 4.29 |

TABLE 1-continued

Table of Array Stable miRNAs for the 13-Tissue Panel as Ranked by Modified Z-Score.

| | Potential Normalizer | Modified Z-score |
|---|---|---|
| | Small Nuclear RNA | |
| 13 | U6 | |
| | Ribosomal RNA | |
| 14 | 5S | |

To assess the expression levels of the miRNAs listed in Table 1, qRT-PCR detection with TaqMan® MicroRNA Assays (Applied Biosystems) was used. The reverse transcription reaction components were prepared on ice prior to the addition of the RNA template as shown in Table 2. Following assembly of the reaction components on ice, 500 pg of the total RNA template prepared in nuclease-free water was added to each appropriate well and mixed with repeat pipetting. The reverse transcription reaction was incubated in a 384-well GeneAmp® PCR System 9700 (Applied Biosystems) at 16° C. for 30 minutes, 42° C. for 30 minutes, 85° C. for 5 minutes, and was placed on wet ice.

TABLE 2

Reverse Transcription Reaction Components.

| Component | µl per 10 µl rxn | Final Concentration |
|---|---|---|
| Nuclease-free water | 5.30 | |
| 10X Reverse Transcription Buffer (Ambion) | 1.00 | 1X |
| dNTP mix (2.5 mM each) (GE Healthcare) | 1.00 | 0.25 mM each |
| 5X RT Primer (Applied Biosystems) | 0.50 | 0.25X |
| RNase Inhibitor (40 U/µl) (Ambion) | 0.10 | 0.4 U/µl |
| Moloney Murine Leukemia Virus Reverse Transcriptase (MMLV-RT)(100 U/µl) (Ambion) | 0.10 | 1 U/µl |
| FirstChoice Total RNA (Ambion) | 2.00 | |

For PCR, the reaction components shown below in Table 3 were assembled on ice prior to the addition of the cDNA from the reverse transcription reaction as prepared in Table 2. Following assembly of the PCR reaction components on ice, 2 µl of the corresponding reverse transcription reaction was transferred to the PCR mix in the appropriate well. The PCR incubation occurred in an ABI PRISM™ 7900HT Fast Real-Time system (Applied Biosystems) at 95° C. for 1 minute, then for 40 cycles of 95° C. for 5 seconds and 60° C. for 30 seconds. The data were collected and results were analyzed with SDS V2.3 (Applied Biosystems).

TABLE 3

Real-Time PCR Components.

| Component | µl per 15 µl rxn | Final Concentration |
|---|---|---|
| Nuclease-free water | 7.80 | |
| MgCl$_2$ (50 mM) | 1.50 | 5 mM |
| 10X PCR Buffer, Minus Mg (Invitrogen) | 1.50 | 1X |
| dNTP Mix (2.5 mM each) (GE Healthcare) | 1.50 | 0.25 mM each |
| 20X TaqMan Assay (Applied Biosystems) | 0.30 | 0.4X |
| 50X ROX Internal Marker (Invitrogen) | 0.30 | 1X |
| Platinum ® Taq DNA Ploymerase (5 U/µl) (Invitrogen) | 0.10 | 0.033 U/µl |
| cDNA from RT reaction | 2.00 | |

Thresholds and baselines were manually determined with thresholds (the point above calculated background) set at 0.1 delta $R_n$ (a measure of the signal magnitude) paired with a baseline starting at 3 cycles and finishing at 17 cycles. The results were exported as tab-delimited text files and then imported into Microsoft Excel for further analysis. The average value of duplicate cycle threshold ($C_t$) values (a log value) was converted to linear quantities, as outlined by the authors of geNorm and NormFinder, for geNorm and NormFinder analysis. As shown in Table 4, hsa-miR-191 is the most stable reference oncomir and hsa-miR-93 is the second most stable reference oncomir as determined by geNorm and Norm-Finder algorithms. In contrast, 5S rRNA was found to be the most unstable and U6 snRNA the second most unstable potential normalizer in this study. The geNorm algorithm was unable to rank hsa-miR-107 due to the low detection range of the miRNA; upon conversion of the $C_t$ values to quantities, values of <0.0001 are considered insignificant and are excluded from analysis. As a consequence, this miRNA was also omitted from the NormFinder analyses.

TABLE 4

Ranking of Potential Normalizers Based on Stability Values as Determined by geNorm and NormFinder Algorithms for 13 Normal Human Tissue RNA Samples.

| geNorm | | | Pairwise: Avg | NormFinder | |
|---|---|---|---|---|---|
| Normalizer Name | M Value | Normalizer Name | Expression Stability | Normalizer Name | Stability Value |
| miR-191 | 0.826 | miR-17-5p | 0.348 | miR-191 | 0.192 |
| miR-93 | 0.881 | miR-106a | 0.348 | miR-93 | 0.296 |
| miR-106a | 0.908 | miR-93 | 0.518 | miR-106a | 0.337 |
| miR-25 | 0.910 | miR-25 | 0.569 | miR-17-5p | 0.353 |
| miR-17-5p | 0.917 | miR-191 | 0.614 | miR-25 | 0.360 |
| miR-16 | 0.956 | miR-16 | 0.653 | miR-16 | 0.394 |
| let-7a | 1.043 | let-7a | 0.709 | let-7a | 0.520 |
| miR-103 | 1.075 | miR-103 | 0.768 | miR-24 | 0.527 |
| miR-24 | 1.087 | miR-24 | 0.814 | miR-103 | 0.531 |
| miR-99a | 1.176 | miR-99a | 0.859 | miR-99a | 0.648 |
| U6 snRNA | 1.366 | U6 snRNA | 0.943 | U6 snRNA | 0.799 |
| 5S rRNA | 1.717 | 5S rRNA | 1.072 | 5S rRNA | 1.098 |

Normalization using the geometric mean of the most stable miRNA pair (hsa-miR-191 and hsa-miR-93) was compared to normalization using the most unstable RNA (5S rRNA). The standard deviation across all miRNAs shows a ~2-fold difference between these two potential normalizers (FIG. 2). This emphasizes that normalization to the appropriate sequencers) is necessary to observe small expression differences associated with biological changes.

Example 2

A Method to Identify a Set of Targets Suitable for Normalization of miRNA qRT-PCR for Matching Tumor and Normal Adjacent Tumor Tissue Samples In a study of five matching human tumor and normal adjacent tumor (NAT) tissue RNA samples, a similar process was employed to choose appropriate miRNA candidates for normalization as described in Example 1. High-signal producing miRNAs from miRNA Array Expression data were filtered by the modified z-score method. This method resulted in the list of miRNAs shown in Table 5 with the exclusion of 5S rRNA, U6 snRNA, and hsa-miR-107 for reasons described in Example 1. FirstChoice total RNA samples for the five tumor and normal adjacent tumor tissue RNA pairs were purchased from Ambion and include: lymphoma (diffuse large B-cell lymphoma), colon (adenocarcinoma, moderately differentiated, grade 2, Stage T4, N1, Mx), prostate (adenocarcinoma, Gleason score 4+3), lung (squamous cell carcinoma, T1 N0 M0), and esophagus (adenocarcinoma). To assess the expression levels of the miRNAs listed in Table 5, qRT-PCR was performed, the data was collected, and $C_t$ values were converted to quantities for geNorm and NormFinder analyses as described in Example 1.

TABLE 5

List of Array Stable miRNAs for the 5 Human Tumor and Normal Adjacent Tumor Tissue Study.
Potential Normalizers let-7a
miR-16
miR-17-5p
miR-23a
miR-24
miR-25
miR-30d
miR-93
miR-103
miR-106a
miR-191
miR-320

In this case, both geNorm and NormFinder showed hsa-let-7a and hsa-miR-191 to be the two most stable reference oncomirs for the NAT samples. In contrast, hsa-miR-103 and hsa-miR-25 were the most stable reference oncomirs for the tumor samples (Table 6).

TABLE 6

Ranking of miRNAs Based on Stability Values as Determined by geNorm and NormFinder Algorithms for Five Human Tumor and Normal Adjacent Tumor Tissue Samples.

| | geNorm | | | Pairwise: Avg | NormFinder | |
|---|---|---|---|---|---|---|
| | Normalizer Name | M Value | Normalizer Name | Expresssion Stability | Normalizer Name | Stability value |
| NAT | miR-191 | 0.594 | miR-191 | 0.187 | let-7a | 0.145 |
| | let-7a | 0.603 | miR-25 | 0.187 | miR-191 | 0.161 |
| | miR-17-5p | 0.606 | miR-17-5p | 0.302 | miR-17-5p | 0.180 |
| | miR-25 | 0.639 | let-7a | 0.342 | miR-25 | 0.247 |

TABLE 6-continued

Ranking of miRNAs Based on Stability Values as Determined by geNorm and NormFinder Algorithms for Five Human Tumor and Normal Adjacent Tumor Tissue Samples.

| | | geNorm | | | NormFinder | |
|---|---|---|---|---|---|---|
| | | | | Pairwise: Avg | | |
| | Normalizer Name | M Value | Normalizer Name | Expresssion Stability | Normalizer Name | Stability value |
| | miR-24 | 0.660 | miR-24 | 0.438 | miR-24 | 0.281 |
| | miR-320 | 0.741 | miR-106a | 0.492 | miR-320 | 0.382 |
| | miR-23a | 0.780 | miR-320 | 0.550 | miR-23a | 0.416 |
| | miR-106a | 0.792 | miR-23a | 0.577 | miR-106a | 0.430 |
| | miR-93 | 0.801 | miR-93 | 0.595 | miR-93 | 0.437 |
| | miR-103 | 0.804 | miR-103 | 0.638 | miR-103 | 0.444 |
| | miR-16 | 0.933 | miR-16 | 0.689 | miR-16 | 0.570 |
| | miR-30d | 1.066 | miR-30d | 0.752 | miR-30d | 0.650 |
| TUMOR | miR-103 | 0.575 | miR-191 | 0.113 | miR-103 | 0.108 |
| | miR-25 | 0.594 | miR-25 | 0.113 | miR-25 | 0.166 |
| | miR-191 | 0.607 | miR-103 | 0.226 | miR-191 | 0.190 |
| | miR-24 | 0.686 | miR-17-5p | 0.352 | miR-24 | 0.312 |
| | let-7a | 0.720 | miR-106a | 0.397 | let-7a | 0.328 |
| | miR-17-5p | 0.764 | miR-16 | 0.417 | miR-23a | 0.410 |
| | miR-23a | 0.764 | let-7a | 0.510 | miR-17-5p | 0.436 |
| | miR-106a | 0.807 | miR-24 | 0.587 | miR-106a | 0.477 |
| | miR-16 | 0.831 | miR-23a | 0.643 | miR-93 | 0.492 |
| | miR-320 | 0.856 | miR-320 | 0.690 | miR-30d | 0.496 |
| | miR-93 | 0.863 | miR-93 | 0.719 | miR-16 | 0.498 |
| | miR-30d | 0.874 | miR-30d | 0.745 | miR-320 | 0.500 |

However, it is not typical for paired tumor and NAT samples to be analyzed as discrete groups. Unlike geNorm, NormFinder has the additional feature to distinguish sample groups, i.e. tumor, normal etc. This extended output feature provides a measure of the intragroup and intergroup variation of each miRNA as shown in Table 7. With these analyses, hsa-miR-191 was the most stable miRNA overall with the least intragroup variation and low intergroup variation. As a combination, hsa-miR-25 and hsa-miR-191 were the most stable pair suitable for normalization of all samples.

TABLE 7

Intragroup and Intergroup Variation of the Five Human Tumor and Normal Adjacent Tumor Tissue Samples.

| Best Normalizer | miR-191 |
|---|---|
| Stability value | 0.078 |
| Best combination of two normalizers | miR-25 and miR-191 |
| Stability value for best combination of two normalizers | 0.061 |

| Intragroup Variation | | | Intergroup Variation | | |
|---|---|---|---|---|---|
| Normalizer Name | Tumor | NAT | Normalizer Name | Tumor | NAT |
| miR-103 | 0.012 | 0.197 | miR-30d | −0.128 | 0.128 |
| miR-25 | 0.027 | 0.061 | miR-23a | −0.115 | 0.115 |
| miR-191 | 0.036 | 0.026 | miR-320 | −0.111 | 0.111 |
| miR-24 | 0.097 | 0.079 | let-7a | −0.072 | 0.072 |
| let-7a | 0.108 | 0.021 | miR-16 | −0.072 | 0.072 |
| miR-23a | 0.168 | 0.173 | miR-24 | 0.011 | −0.011 |
| miR-17-5p | 0.190 | 0.032 | miR-191 | 0.045 | −0.045 |
| miR-106a | 0.227 | 0.185 | miR-103 | 0.047 | −0.047 |
| miR-93 | 0.242 | 0.191 | miR-106a | 0.081 | −0.081 |
| miR-30d | 0.246 | 0.423 | miR-25 | 0.101 | −0.101 |
| miR-16 | 0.248 | 0.325 | miR-17-5p | 0.103 | −0.103 |
| miR-320 | 0.250 | 0.146 | miR-93 | 0.109 | −0.109 |

Figure 3:
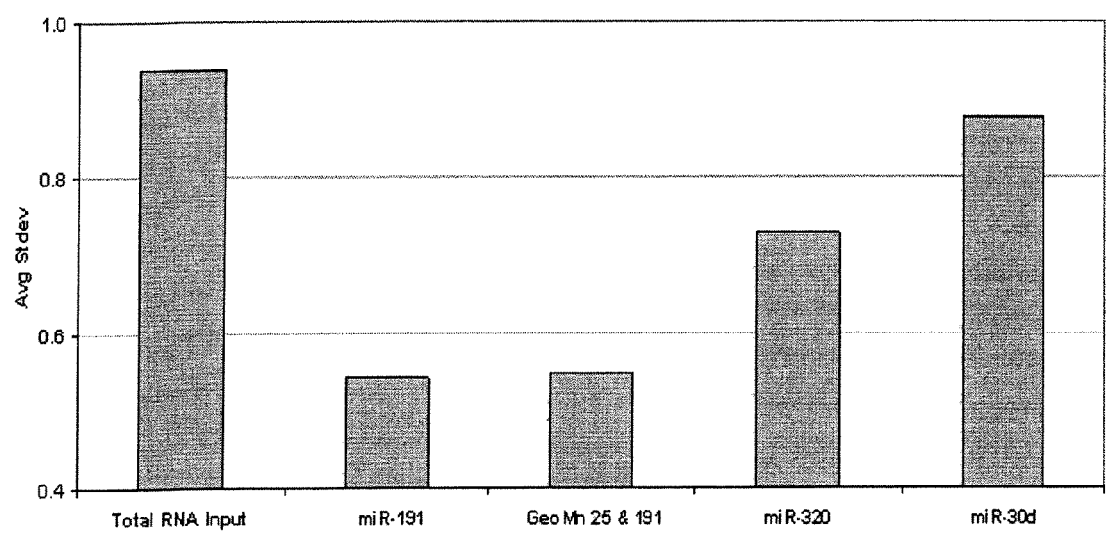
FIG. 3 is a graph representing the average standard deviation of normalized qRT-PCR results of miRNAs listed in Table 5. The x-axis indicates the normalizer(s) used, and the y-axis shows the resulting average standard deviation across the tumor (T) and normal adjacent tumor (NAT) tissue samples of Example 2. Where more than one miRNA normalizer is used, the data is normalized to the GeoMn of the miRNA normalizers.

A comparison of the most stable miRNA to the least stable miRNA is shown in FIG. 3. Normalization of the qRT-PCR experimental results to the most stable miRNA (hsa-miR191) produced the lowest standard deviation compared to the least stable miRNA (hsa-miR-30d) as shown in FIG. 3.

Example 3

A Method to Identify a Set of miRNAs Suitable for Normalization of miRNA qRT-PCR Data to Observe Small Expression Differences Associated with Biological Changes In another study of 12 human lung tumor and NAT tissue RNA pairs, suitable miRNAs for normalization were chosen as described in Example 1 and Example 2. FirstChoice total RNA samples were purchased from Ambion with tumor staging of T2 for 11 samples and T3 for one sample and a clinical diagnosis of squamous cell carcinoma procured from human male subjects between 47 and 69 years of age. For the panel of 12 human lung tumor/NAT pairs, 16 prospective normalization miRNAs were selected for qRT-PCR analysis (Table 8). To assess the expression levels of the miRNAs listed in Table 8, qRT-PCR was performed, the data collected, and $C_t$ values converted to quantities for NormFinder analyses as described in Example 1.

TABLE 8

List of Array Stable Targets for the 12 Frozen Human Lung Tumor and Normal Adjacent Tumor Tissue Study.
Potential
Normalizer let-7a
miR-16
miR-17-5p
miR-24
miR 27a
miR-30d
miR-93
miR-103
miR-106a TABLE 8-continued List of Array Stable Targets for the 12 Frozen Human Lung Tumor and Normal Adjacent Tumor Tissue Study.

Potential Normalizer miR-125a
miR-143
miR-146a
miR-191
miR-195
miR-221
5S rRNA

The NormFinder ranking of each miRNA found hsa-miR-191 to be the most stable single miRNA and hsa-let-7a and hsa-miR-103 as the most stable combination within this data set. Hsa-miR-30d, hsa-miR-221, and hsa-miR-143 were less stably expressed than 5S rRNA in these lung tumor and NAT samples (Table 9).

TABLE 9

NormFinder Ranking of miRNAs in Order of Stability for the 12 Frozen Human Lung Tumor and Normal Adjacent Tumor Tissue Study.

| Normalizer name | Stability value |
|---|---|
| miR-191 | 0.121 |
| miR-125a | 0.171 |
| miR-24 | 0.195 |
| miR-103 | 0.204 |
| miR-17-5p | 0.211 |
| let-7a | 0.232 |
| miR-27a | 0.257 |
| miR-106a | 0.293 |
| miR-146a | 0.324 |
| miR-16 | 0.351 |
| miR-195 | 0.356 |
| miR-93 | 0.365 |
| 5S rRNA | 0.379 |
| miR-143 | 0.434 |
| miR-221 | 0.491 |
| miR-30d | 0.591 |

Best Single Target: miR-191
Stability Value: 0.121
Best Combination: let-7a and miR-103
Stability Value: 0.073

Further analysis of the intragroup and intergroup variation showed that the combination of hsa-let-7a and hsa-miR-103 had the lowest variation (Table 10).

TABLE 10

Intragroup and Intergroup Variation of the 12 Frozen Human Lung Tumor and Normal Adjacent Tumor Tissue Samples.

| | Intragroup Variation | | Intergroup Variation | | |
|---|---|---|---|---|---|
| Normalizer name | Tumor | NAT | Normalizer name | Tumor | NAT |
| miR-103 | 0.032 | 0.031 | miR-30d | −0.481 | 0.481 |
| miR-24 | 0.046 | 0.091 | miR-195 | −0.288 | 0.288 |
| miR-191 | 0.061 | 0.059 | miR-143 | −0.287 | 0.287 |
| miR-16 | 0.066 | 0.206 | miR-16 | −0.234 | 0.234 |
| miR-195 | 0.084 | 0.011 | let-7a | −0.128 | 0.128 |
| miR-125a | 0.099 | 0.251 | miR-146a | −0.051 | 0.051 |
| let-7a | 0.102 | 0.056 | miR-191 | −0.024 | 0.024 |
| miR-17-5p | 0.111 | 0.062 | miR-125a | 0.012 | −0.012 |
| miR-93 | 0.131 | 0.107 | miR-27a | 0.088 | −0.088 |
| 5S rRNA | 0.183 | 0.093 | miR-24 | 0.097 | −0.097 |
| miR-30d | 0.188 | 0.391 | miR-17-5p | 0.101 | −0.101 |
| miR-106a | 0.208 | 0.097 | miR-103 | 0.136 | −0.136 |
| miR-27a | 0.213 | 0.222 | miR-106a | 0.159 | −0.159 |
| miR-221 | 0.327 | 0.050 | miR-93 | 0.251 | −0.251 |
| miR-143 | 0.347 | 0.204 | 5S rRNA | 0.261 | −0.261 |
| miR-146a | 0.418 | 0.852 | miR-221 | 0.387 | −0.387 |

Figure 4:
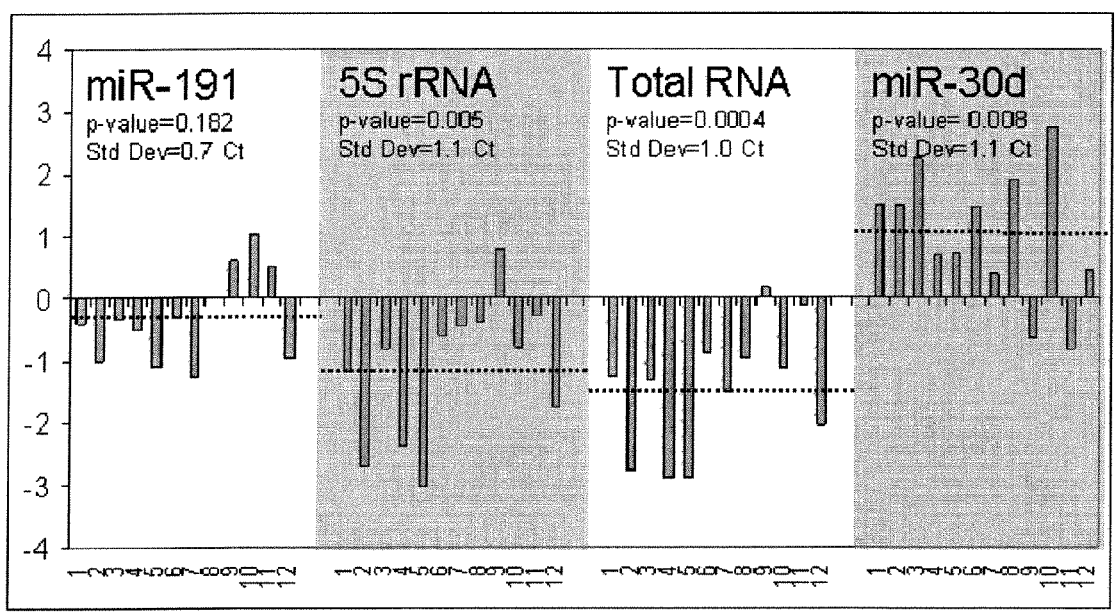
FIG. 4 is a graph of hsa-let-7a differential expression in Frozen LuCa as normalized to 1) Hsa-miR-191, 2) 5S rRNA, 3) Total RNA, and 4) Hsa-miR-30d. The y-axis represents the delta-delta comparative threshold ($ddC_t$) value of tumor tissue less NAT for hsa-let-7a expression normalized to hsa-miR-191, 5S rRNA, or hsa-miR-30d. In the case of normalization to total RNA, the same mass of RNA was added to each qRT-PCR well, enabling direct $C_t$-to-$C_t$ comparisons. The p-value was determined by a two-tailed paired Student's t-test from the $dC_t$ values of tumor and NAT (or $C_t$ values in the case of normalization to total RNA). The standard deviation was calculated from the $ddC_t$ values (or $dC_t$ values in the case of total RNA). The average differential expression (in $C_t$'s) across all samples is represented by the dotted line on each graph.

FIG. 4 shows hsa-let-7a differential expression in Frozen Lung Cancer as normalized to 1) Hsa-miR-191, 2) 5S rRNA, 3) Total RNA, and 4) Hsa-miR-30d. The y-axis represents the ddC$_t$ (tumor tissue less NAT) value for hsa-let-7a expression normalized to hsa-miR-191, 5S rRNA, or hsa-miR-30d. The ddC$_t$ was determined by first subtracting the C$_t$ value for hsa-let-7a for each sample from the corresponding C$_t$ value of the normalizer, creating the dC$_t$ value. Next, the dC$_t$ value for hsa-let-7a for the NAT was subtracted from the matching dC$_t$ value of the tumor tissue sample, creating the ddC$_t$ value. For example in the case of normalization to hsa-miR-191: dC$_t$(hsa-let-7a)=C$_t$(hsa-miR-191)−C$_t$(hsa-let-7a) and ddC$_t$(hsa-let-7a)=dC$_t$(hsa-let-7a, tumor)−dC$_t$(hsa-let-7a, NAT). Thus, a negative ddC$_t$ value indicates decreased expression of the target miRNA in the tumor, and a positive ddC$_t$ reflects increased expression of the target miRNA in the tumor.

In the case of normalization to total RNA, the same mass of RNA was added to each RT-PCR well. As such, a ddC$_t$ calculation is not necessary since the fixed input of total RNA enables direct C$_t$-to-C$_t$ comparisons. Following this calculation, the y-axis represents the dC$_t$ value for hsa-let-7a expression, which is determined by: dC$_t$(hsa-let-7a)=C$_t$(hsa-let-7a, tumor)−C$_t$(hsa-let-7a, NAT). The p-value was determined by a two-tailed paired Student's t-test from the dC$_t$ values of tumor and NAT (or C$_t$ values in the case of normalization to total RNA). The standard deviation was calculated from the ddC$_t$ values (or dC$_t$ values in the case of total RNA). The average differential expression (in C$_t$'s) across all samples is represented by the dotted line on each graph.

The expression of hsa-let-7a in flash-frozen lung tumor tissue compared to the matching flash-frozen lung NAT is down in 8/12 of the cancer pairs when normalized to the most stable target identified by the NormFinder algorithm, hsa-miR-191 in FIG. 4. In addition, the dotted line reflects the average apparent differential expression of let-7a across the 12 flash-frozen lung tumor and normal adjacent tissue pairs for each normalizer. One would expect a value close to zero for a target with no differential expression; however, let-7a has been reported to be slightly downregulated in Lung Cancer tumors. Consistent with this finding, FIG. 4 demonstrates that when normalized to hsa-miR-191, let-7a has an average ddCt value of −0.3 (down ~1.2-fold in cancer). We note that when normalized to 5S ribosomal RNA or total RNA input, the expression of hsa-let-7a is primarily down in 11/12 tumor and NAT pairs; however, the increased standard deviation compared to miR-191 reflects the variability and instability of each as unsuitable normalizers. Normalization to 5S rRNA levels indicates a down regulation of let-7a that is exaggerated (2.18 fold for 5S; 2.76 fold for total RNA, compared to ~1.2 fold, p-value 0.182 for normalization to miR-191). In a more extreme case, such as normalization to hsa-miR-30d, which is less stably expressed than 5S rRNA in these lung tumor and NAT samples, the expression of hsa-let-7a is shifted to appear higher in 10/12 of the cancer pairs, which is in the opposite direction of the other three normalizers. The p-value suggests confidence in this interpretation of let-7a up regulation in lung tumor, which is at odds with published data (Inamura et al., *Lung Cancer*, Aug. 27, 2007 [Epub ahead of print]). Thus, the choice of the correct normalizer such as described herein, allows the correct interpretation of miRNA expression data.

Table 11 compares the use of hsa-miR-191 and hsa-miR-30d to normalize the expression of hsa-let-7a. Use of hsa-miR-30d indicated a 2.02-fold increase in hsa-let-7a, which was a misleading result given that use of hsa-miR-191 showed a 1.23-fold decrease in let-7a levels. Normalization to another miRNA that is less stably expressed in these tissues than 5S rRNA, hsa-miR-221, indicates that the average change of hsa-let-7a expression is down by 2.81-fold as shown in Table 11. The overall difference between normalization to hsa-miR-30d (2.02-fold) and normalization to hsa-miR-221 (−2.81-fold) expands to a 5.68 fold change in linear space. This is a large difference that would mask the ability to distinguish smaller, but potentially biologically significant changes.

TABLE 11

Apparent hsa-let-7a Differential Expression in Frozen Lung Cancer When Normalized to Various Unstable RNA miRNAs Compared to the Result When Normalized to a Stable miRNA Such as hsa-miR-191.

| Potential Normalizers For Let-7a Expression | Average Fold Change |
|---|---|
| miR-30d | +2.02 |
| miR-191 | −1.23 |
| miR-103 | −1.70 |
| 5S rRNA | −2.18 |
| Total RNA | −2.76 |
| miR-221 | −2.81 |

Figure 5:
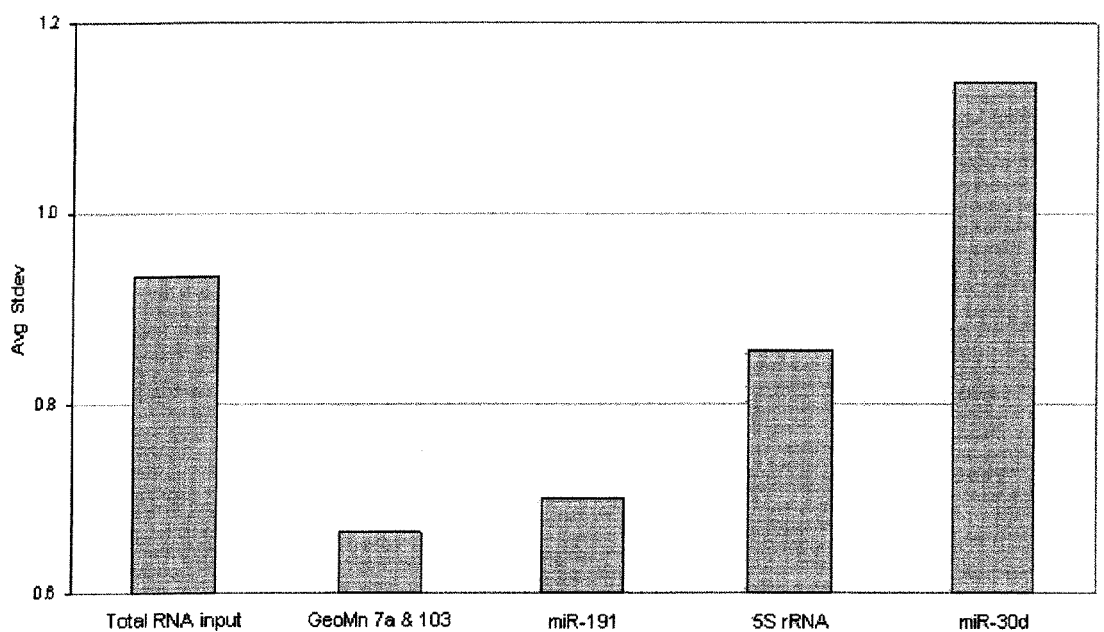
FIG. 5 is a graph representing the average standard deviation of normalized qRT-PCR results of miRNAs listed in Table 8. The x-axis indicates the normalizer(s) used, and the y-axis shows the resulting average standard deviation across the human lung tumor and NAT samples of Example 3. Where more than one miRNA normalizer is used, the data is normalized to the GeoMn of the miRNA normalizers.

Also, normalization to total RNA input into the qRT-PCR reaction also failed to be a stable measure of let-7a expression, as shown in FIG. 5, and by the much lower measured differential expression of let-7a in lung tumor samples. Indeed, normalization to total RNA suggested that let-7a was downregulated by 2.76-fold in lung tumors.

A further comparison of normalization with the most stable pair versus normalization with the least stable miRNA is shown in FIG. 5. Normalization of the qRT-PCR experimental results to the geometric mean of hsa-let-7a and hsa-miR-103 produced the lowest standard deviation as shown in FIG. 5.

Example 4

A Method to Identify a Set of miRNAs Suitable for Normalization of miRNA qRT-PCR Data to Observe Small Expression Differences Associated with Biological Changes in Formalin-Fixed Paraffin Embedded (FFPE) Tissue Samples In another example with Formalin-Fixed Paraffin Embedded (FFPE) human tissue samples comprising 16 lung tumor and NAT RNA pairs, prospective miRNAs for normalization were selected based upon high levels of expression on miRNA microarrays. The FFPE tissue samples were procured from Phylogeny, with clinical diagnosis of non-small cell squamous cell carcinoma staged T2, T3, and T4. The age of the FFPE samples ranged approximately from one to eleven years with five sample pairs at one year old, six sample pairs at four years old, and five sample pairs at eleven years of age. The RNA was isolated with RecoverAll™ Total Nucleic Acid Isolation Kit for FFPE (Ambion) according to the manufacturer's recommendations. To assess the expression levels of the targets listed in Table 12, qRT-PCR was performed, the data collected, and $C_t$ values converted to quantities. NormFinder analyses were performed as described in Example 1, except a total of 10 ng RNA was added to the reverse transcription reaction.

TABLE 12

Table of miRNAs for Normalization for 16 Human FFPE Lung Tumor and Normal Adjacent Tumor Tissue Study.

| Potential Normalizers |
|---|
| let-7a |
| miR-16 |
| miR-17-5p |
| miR-24 |
| miR-25 |
| miR-103 |
| miR-106a |
| miR-191 |

The NormFinder ranking of each potential normalizer found hsa-miR-103 to be the most stable single miRNA, and hsa-miR-17-5p and hsa-miR-24 to be the most stable combination within this data set. Hsa-miR-16 was the most unstable miRNA as shown in Table 13.

TABLE 13

NormFinder Ranking of miRNAs in Order of Stability for the 16 Human FFPE Lung Tumor and Normal Adjacent Tumor Tissue Study.

| Normalizer name | Stability value |
|---|---|
| miR-103 | 0.127 |
| miR-191 | 0.222 |
| miR-24 | 0.309 |
| miR-17-5p | 0.363 |
| let-7a | 0.368 |
| miR-106a | 0.395 |
| miR-25 | 0.407 |
| miR-16 | 0.418 |

Best Single Normalizer: miR-103
Stability Value: 0.127
Best Combination: miR-17-5p and miR-24
Stability Value: 0.110

Figure 6:
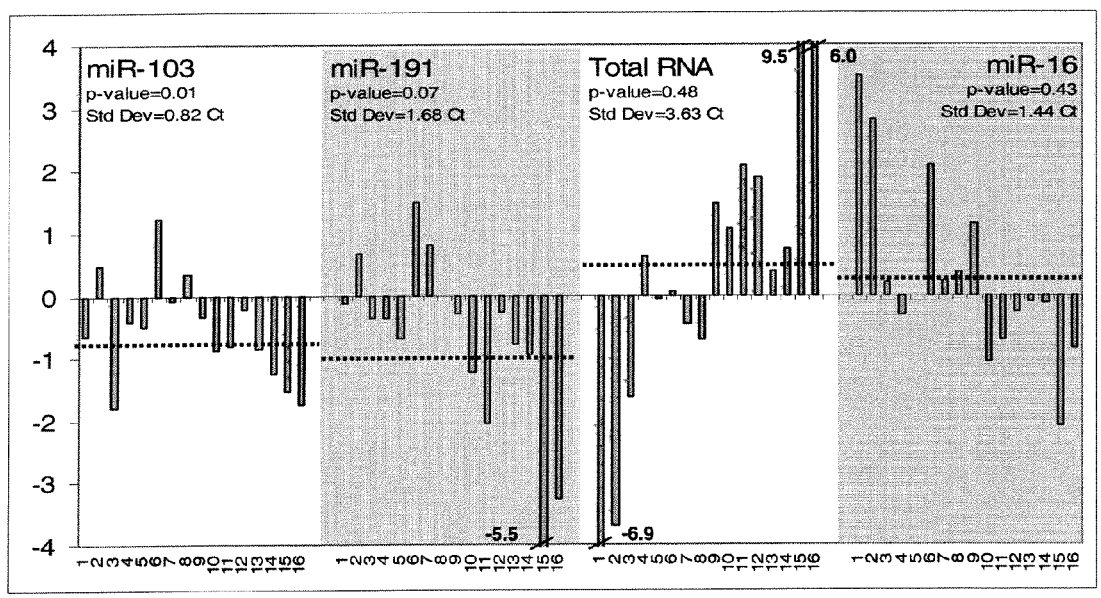
FIG. 6 is a graph of hsa-let-7a expression in FFPE LuCa represented as $ddC_t$ (T-NAT), normalized to 1) Hsa-miR-103, 2) Hsa-miR-191, 3) Total RNA, and 4) Hsa-miR-16. The y-axis represents the $ddC_t$ (tumor tissue less NAT) value for has-let-7a expression normalized to hsa-miR-103, hsa-miR-191, and hsa-miR-16. In the case of normalization to total RNA, the same mass of RNA was added to each qRT-PCR well, enabling direct $C_t$-to-$C_t$ comparisons. The p-value was determined by a two-tailed paired Student's t-test from the $dC_t$ values of tumor and NAT (or $C_t$ values in the case of normalization to total RNA). The standard deviation was calculated from the $ddC_t$ values (or $dC_t$ values in the case of total RNA). The average differential expression (in $C_t$'s) across all samples is represented by the dotted line on each graph.

FIG. 6 shows hsa-let-7a expression in FFPE LuCa represented as $ddC_t$ (T-NAT), normalized to 1) Hsa-miR-103, 2) Hsa-miR-191, 3) Total RNA, and 4) Hsa-miR-16. The y-axis represents the $ddC_t$ (tumor tissue less Normal adjacent tissue) value for hsa-let-7a expression normalized to hsa-miR-103, hsa-miR-191, and hsa-miR-16. The $ddC_t$ was determined as described in Example 3.

The p-value was determined by a two-tailed paired Student's t-test from the $dC_t$ values of tumor and NAT (or $C_t$ values in the case of normalization to total RNA). The standard deviation was calculated from the $ddC_t$ values (or $dC_t$ values in the case of total RNA). The average differential expression (in $C_t$'s) across all samples is represented by the dotted line on each graph.

The expression of hsa-let-7a in FFPE lung tumor tissue compared to the matching FFPE lung normal adjacent tissue (NAT) is down in 13/16 of the cancer pairs when normalized to the most stable target identified by the NormFinder algorithm, hsa-miR-103. Let-7a differential expression was associated with a p-value of 0.01, reflecting statistical confidence in the interpretation that let-7a is down regulated in Lung Cancer tumors. Consistent with this finding, Table 11 and Table 15 demonstrates that normalization to hsa-miR-191 results in an average ddC$_t$ value of −0.80 (down ~1.76-fold in cancer). Nominally, this value for reduced expression in let-7a is in good agreement with that determined for the independent frozen Lung Cancer sample set, where let-7a was determined to be down ~1.23 fold. In contrast, normalization to total RNA input reports that the expression of hsa-let-7a is shifted up in 10/16 of the cancer pairs, with a positive average differential expression of 0.65 C$_t$ (~1.6 fold) and two tumor-NAT pairs showing a ddC$_t$ value of 6.0 and 9.5 with one pair showing a ddC$_t$ value of −6.9. The standard deviation value of 3.63 (compared to 0.82 for hsa-miR-103) also reflects the variability and instability demonstrating classic features of an unsuitable normalizer. For the case of normalization to hsa-miR-16, the differential expression of hsa-let-7a is ambiguous with 7/16 of the sample pairs up and 9/16 of the sample pairs down.

Further analysis of the intragroup and intergroup variation showed that the combination of hsa-miR-17-5p and hsa-miR-24 had the lowest variation (Table 14).

TABLE 14

Intragroup and Intergroup Variation of the 16 Human FFPE Lung Tumor and Normal Adjacent Tumor Tissue Samples.

| Intragroup Variation | | | Intergroup Variation | | |
|---|---|---|---|---|---|
| Normalizer name | Tumor | NAT | Normalizer name | Tumor | NAT |
| hsa-miR-16 | 0.101 | 0.273 | hsa-miR-16 | −0.314 | 0.314 |
| hsa-miR-103 | 0.125 | 0.087 | hsa-let-7a | −0.212 | 0.212 |
| hsa-miR-24 | 0.180 | 0.076 | hsa-miR-24 | −0.207 | 0.207 |
| hsa-miR-17-5p | 0.372 | 0.082 | hsa-miR-103 | −0.016 | 0.016 |
| hsa-miR-191 | 0.440 | 0.094 | hsa-miR-191 | 0.070 | −0.070 |
| hsa-miR-106a | 0.481 | 0.109 | hsa-miR-25 | 0.159 | −0.159 |
| hsa-let-7a | 0.509 | 0.278 | hsa-miR-17-5p | 0.247 | −0.247 |
| hsa-miR-25 | 1.040 | 1.096 | hsa-miR-106a | 0.272 | −0.272 |

Hsa-let-7a expression normalization by miR-16 and miR-25 (the least stable miRNAs) showed that expression was up by 1.23-fold or down by 2.10-fold respectively. These were both misleading results when compared to normalization of the data to miR-103, which showed that expression of let-7a was down by 1.48-fold. It is worth noting that the independent selection of the most stable miRNA and its application to let-7a data normalization for frozen tumor versus NAT lung cancer tissue (Table 11) or, separately, for FFPE tumor versus NAT lung cancer tissue (Table 15) results in very similar levels of let-7a down regulation in lung cancer (−1.23-fold versus −1.48-fold), even though the sample sets that were interrogated were unique and non-overlapping (Table 15).

TABLE 15

Hsa-let-7a Differential Expression in FFPE Lung Cancer When Normalized to an Unstable miRNA Such as hsa-miR-16 and hsa-miR-25 Compared to the Result When Normalized to a More Stable miRNA Such as hsa-miR-103.

| Potential Normalizers For Let-7a Expression | Average Fold Change |
|---|---|
| Total RNA | +1.57 |
| miR-16 | +1.23 |
| miR-103 | −1.48 |
| miR-191 | 1.76 |
| miR-25 | −2.10 |

Inspection of FIGS. 4 and 6 revealed that the most invariant miRNA for the set of frozen LuCa and NAT samples, miR-191, was not the most invariant miRNA for the set of FFPE LuCa and NAT samples. Instead, miR-103 was the most stable target for the FFPE sample set. Although this result would appear to be an inconsistency across the two datasets, a deeper analysis of the data demonstrated that these two miRNA normalizers were actually very similar in stability, in spite of their differences in rank order. NormFinder reports the stability value as a measure of statistical variation that is relative to the dataset that is analyzed. These values are difficult to interpret directly by conventional measures of qRT-PCR experiments, such as dC$_t$ or fold change. An alternate way to express the effectiveness of a normalizer is to calculate the dC$_t$ value for each target across all samples, and then average this variation (that is, the standard deviation of the dC$_t$ value) across all targets and samples. When this calculation was performed with the frozen Lung Cancer sample set, the standard deviation of the dC$_t$ was almost exactly the same when the miRNA targets were normalized to miR-191 (SD=0.75 C$_t$) or, separately, miR-103 (SD=0.73 C$_t$). This result was in stark contrast to the standard deviation calculated using less stable targets, such as miR-30d (SD=1.21 C$_t$) or even 5S RNA (SD=0.91 C$_t$) or total RNA (SD=0.93 C$_t$). Thus, miR-191 and miR-103 are both good choices of normalizers and are more similar in performance than their rank order by NormFinder would suggest. It is surprising, and wholly unexpected, that common miRNA targets evaluated in the frozen and FFPE sample sets were ordered by stability in exactly the same way, save the inversion of miR-103 with miR-191 in the FFPE set (see Table 16 below). This is a particularly remarkable result given that the two tissue sources were procured independently of one another, and, further, that FFPE samples present significant sources of variation in RNA expression profiling compared to flash-frozen samples. For example, FFPE samples are subjected to harsh chemical fixation and high temperature embedded in paraffin-processing that both damages RNA species and adds variability to RNA representation following extraction and amplification. In spite of these differences, the observed conservation in miRNA stability across frozen and FFPE sample groups is a testament to their utility in normalizing qRT-PCR data for disparate tissue preparation methods.

TABLE 16

Rank Order Stability Comparisons of RNA Normalization Targets for Frozen and FFPE LuCa Sample Sets.
Stability order was determined using NormFinder and is presented from most stable (top) to least stable (bottom).
The miRNA targets in bold are those that ordered the same for both groups.

| Rank in Frozen LuCa Samples | Rank in FFPE LuCa Samples |
|---|---|
| miR-191 | miR-103 |
| miR-125a | Not tested |
| miR-24 | miR-24 |
| miR-103 | miR-191 |
| miR-17-5p | miR-17-5p |
| let-7a | let-7a |
| miR-27a | Not tested |
| miR-106a | miR-106a |
| miR-146a | Not tested |
| miR-16 | miR-16 |
| miR-195 | Not tested |
| miR-93 | Not tested |
| 5s | Not tested |
| miR-143 | Not tested |
| miR-221 | Not tested |
| miR-30d | Not tested |

Example 5

Multiplex Assay for Quantifying and Normalizing Target miRNAs

Techniques for multiplex PCR experiments are provided in Jansen et al., *Leukemia*. 19(11):2016-2018 (2005); Molenkamp et al., *J Virol Methods*. 141 (2):205-11 (2007); Bijwaard et al., *J Mol Diagn*. 4(1):59-64 (2002); Payungporn et al., *J Virol Methods*. 131(2):143-147 (2006); and Hindiyeh et al., *J Clin Microbiol*. 43(2):589-95.

To quantify and normalize a target miRNA to a reference oncomir in the same reaction volume, a reverse transcription reaction is first performed as described in Example 1 and Table 2, using reverse transcriptase primers that are complementary to target miRNA and reference oncomir sequences in lieu of the 5×RT primer. During the reverse transcription incubation a cDNA strand is created for each associated reverse transcriptase primer from a single RNA sample well. For multiplexed real-time PCR, the reaction components shown below in Table 17 are assembled on ice prior to the addition of the cDNA from the multiplexed reverse transcription reaction. Primers are selected to allow specific amplification of the sequences of interest. Following assembly of the PCR reaction components, 2 μl of the reverse transcription reaction is transferred to the PCR mix. The PCR incubation occurs in an ABI PRISM™ 7900HT Fast Real-Time system (Applied Biosystems) at 95° C. for 1 minute, then for 40 cycles of 95° C. for 5 seconds and 60° C. for 30 seconds. The data are collected and results analyzed with SDS V2.3 (Applied Biosystems).

TABLE 17

Multiplex real-time PCR components.

| Component | μl per 15 μl rxn |
|---|---|
| Nuclease-free water | 5.10 |
| MgCl$_2$ (50 mM) | 1.50 |
| 10X PCR Buffer, Minus Mg (Invitrogen) | 1.50 |
| dNTP Mix (2.5 mM each) (GE Healthcare) | 1.50 |
| Target miRNA forward primer | 0.50 |
| Target miRNA reverse primer | 0.50 |
| Target miRNA probe (label A) | 0.50 |
| Reference oncomir forward primer | 0.50 |
| Reference oncomir reverse primer | 0.50 |
| Reference oncomir probe (label B) | 0.50 |
| 50X ROX Internal Marker (Invitrogen) | 0.30 |
| Platinum ® Taq DNA Ploymerase (5 U/μl) (Invitrogen) | 0.10 |
| cDNA from RT reaction | 2.00 |

Data for both target miRNA and reference oncomirs are obtained from the same reaction volume using sequence-specific probes with distinguishable labels. Target miRNA quantification data are normalized base on measurements of reference oncomir amounts.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All references cited herein are incorporated herein by reference in their entirety. To the extent publications and patents or patent applications incorporated by reference contradict the invention contained in the specification, the specification will supersede any contradictory material.

What is claimed is:

1. A method of quantifying the amount of a target microRNA (miRNA) in a biological fluid or tissue sample, the method comprising:
   (a) measuring the amount of the target miRNA in the sample in a reaction volume;
   (b) measuring the amount of at least one endogenous reference oncomir in the reaction volume; and
   (c) normalizing the target miRNA measurement based on the amount of at least one endogenous reference oncomir.

2. The method of claim 1, comprising measuring the amount of a first and a second endogenous reference oncomir in the biological fluid or tissue sample and normalizing the target miRNA levels to the first and second endogenous reference oncomirs.

3. The method of claim 1, further comprising amplifying the target miRNA and the at least one endogenous reference oncomir in the reaction volume.

4. The method of claim 3, wherein the amplification includes real-time polymerase chain reaction amplification.

5. The method of claim 1, wherein the at least one endogenous reference oncomir is chosen from let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-17-3p, miR-17-5p, miR-181a, miR-181b, miR-181c, miR-183, miR-184, miR-186, miR-187, miR-189, miR-18a, miR-190, miR-191, miR-192, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a.

6. The method of claim 1, wherein the at least one endogenous reference oncomir is chosen from hsa-miR-191, hsa-miR-93, hsa-miR-106a, hsa-miR-25, hsa-miR-17-5p, hsa-miR-103, hsa-miR-24, hsa-miR-99a, hsa-miR-320, hsa-miR-23a, hsa-miR-125a, hsa-miR-27a, hsa-miR-146a, and hsa-miR-195.

7. The method of claim 1, wherein part (b) comprises measuring the amount of miR-191.

8. The method of claim 1, wherein part (b) comprises measuring the amount of miR-103.

9. The method of claim 1, wherein measuring the amount of at least one reference oncomir consists of measuring a first and a second endogenous reference oncomir.

10. The method of claim 9, wherein the first and second endogenous reference oncomir are each chosen from hsa-miR-191, hsa-miR-93, hsa-miR-106a, hsa-miR-25, hsa-miR-17-5p, hsa-miR-16, hsa-let-7a, hsa-miR-103, hsa-miR-24, hsa-miR-99a, hsa-miR-320, hsa-miR-23a, hsa-miR-30d, hsa-miR-125a, hsa-miR-27a, hsa-miR-146a, hsa-miR-195, hsa-miR-143, and hsa-miR-221.

11. The method of claim 9, wherein the first and second endogenous reference oncomirs are a pair chosen from hsa-miR-191 and hsa-miR-93, hsa-miR-25 and hsa-miR-191, hsa-let-7a and hsa-miR-103, and hsa-miR-17-5p and hsa-miR-24.

12. The method of claim 1, wherein measuring the amount of at least one endogenous reference oncomir consists of measuring a endogenous reference oncomir chosen from hsa-miR-191, hsa-miR-93, hsa-miR-106a, hsa-miR-25, hsa-miR-17-5p, hsa-miR-103, hsa-miR-24, hsa-miR-99a, hsa-miR-320, hsa-miR-23a, hsa-miR-125a, hsa-miR-27a, hsa-miR-146a, and hsa-miR-195.

13. A method of normalizing the amount of a target miRNA in a biological fluid or tissue sample, comprising measuring the amount of the target miRNA and the amount of a first endogenous reference oncomir in the sample in a single reaction volume and normalizing the target miRNA measurement based on the amount of the reference oncomir in the sample.

14. The method of claim 13, further comprising measuring the amount of a second endogenous reference oncomir in the biological fluid or tissue sample and normalizing the target miRNA level to the first and second reference oncomirs.

15. The method of claim 13, further comprising amplifying the target miRNA and the first endogenous reference oncomir in the reaction volume.

16. The method of claim 14, wherein the first and second endogenous reference oncomirs are chosen from hsa-miR-191, hsa-miR-93, hsa-miR-106a, hsa-miR-25, hsa-miR-17-5p, hsa-miR-16, hsa-let-7a, hsa-miR-103, hsa-miR-24, hsa-miR-99a, hsa-miR-320, hsa-miR-23a, hsa-miR-125a, hsa-miR-27a, hsa-miR-146a, and hsa-miR-195.

17. A method for quantifying the relative expression of a target miRNA in biological fluid or tissue samples, the method comprising:
   (a) measuring the amount of the target miRNA sequence and a first endogenous reference oncomir sequence in a first biological sample in a first reaction volume;
   (b) measuring the amount of the target miRNA sequence and the first reference oncomir endogenous sequence in a second biological sample in a second reaction volume; and
   (c) normalizing the target miRNA level to the endogenous reference oncomir level for the first and second samples, thereby quantifying the relative expression of the target miRNA.

18. The method of claim 17, further comprising amplifying the target miRNA and the first endogenous reference oncomir in the first reaction volume and amplifying the target miRNA and the first endogenous reference oncomir in the second reaction volume.

19. A method of quantifying the amount of a target microRNA (miRNA) in a biological fluid or tissue sample, the method comprising:
   (a) measuring the amount of the target miRNA in the sample;
   (b) measuring the amount of one to three endogenous reference oncomirs chosen from let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a in the sample; and
   (c) normalizing the target miRNA measurement based on the amount of at least one endogenous reference oncomir.

20. The method of claim 19, comprising measuring the amount of two or three endogenous reference oncomirs in the biological fluid or tissue sample and normalizing the target miRNA levels to the reference oncomirs.

21. The method of claim 19, wherein the endogenous reference oncomir is chosen from hsa-miR-191, hsa-miR-93, hsa-miR-106a, hsa-miR-25, hsa-miR-17-5p, hsa-miR-103, hsa-miR-24, hsa-miR-99a, hsa-miR-320, hsa-miR-23a, hsa-miR-125a, hsa-miR-27a, hsa-miR-146a, and hsa-miR-195.

22. The method of claim 19, wherein part (b) comprises measuring the amount of miR-191.

23. The method of claim 19 wherein part (b) comprises measuring the amount of miR-103.

24. A kit for quantifying the amount of a target miRNA in a biological fluid or tissue sample comprising:
   (a) a first amplification primer set, wherein at least one primer comprises a sequence that is complementary to a portion of a target miRNA;
   (b) a second amplification primer set, wherein at least one primer comprises a sequence that is complementary to a portion of an endogenous reference oncomir;
   (c) a first probe comprising a sequence that is complementary to a portion of the target miRNA; and
   (d) a second probe comprising a sequence that is complementary to a portion of the endogenous reference oncomir;
   wherein the first and second probes are distinguishably detectable.

* * * * *

UNITED STATES PATENT AND TRADEMARK OFFICE
CERTIFICATE OF CORRECTION

PATENT NO. : 7,993,831 B2  
APPLICATION NO. : 11/855792  
DATED : August 9, 2011  
INVENTOR(S) : Gary J. Latham et al.

Page 1 of 1

It is certified that error appears in the above-identified patent and that said Letters Patent is hereby corrected as shown below:

Claim 5, column 95, lines 46-47, change "miR-192, miR-197," to
-- miR-192, miR-195, miR-197, --.

Signed and Sealed this
Twenty-seventh Day of September, 2011

David J. Kappos
*Director of the United States Patent and Trademark Office*

SEQUENCE LISTING

```
<160> NUMBER OF SEQ ID NOS: 236

<210> SEQ ID NO 1
<211> LENGTH: 22
<212> TYPE: RNA
<213> ORGANISM: Homo sapiens

<400> SEQUENCE: 1
ugagguagua gguuguauag uu                                                 22

<210> SEQ ID NO 2
<211> LENGTH: 22
<212> TYPE: RNA
<213> ORGANISM: Homo sapiens

<400> SEQUENCE: 2
ugagguagua gguugugugg uu                                                 22

<210> SEQ ID NO 3
<211> LENGTH: 22
<212> TYPE: RNA
<213> ORGANISM: Homo sapiens

<400> SEQUENCE: 3
ugagguagua gguuguaugg uu                                                 22

<210> SEQ ID NO 4
<211> LENGTH: 22
```

```
<212> TYPE: RNA
<213> ORGANISM: Homo sapiens

<400> SEQUENCE: 4
agagguagua gguugcauag uu                                              22

<210> SEQ ID NO 5
<211> LENGTH: 22
<212> TYPE: RNA
<213> ORGANISM: Homo sapiens

<400> SEQUENCE: 5
ugagguagga gguuguauag uu                                              22

<210> SEQ ID NO 6
<211> LENGTH: 22
<212> TYPE: RNA
<213> ORGANISM: Homo sapiens

<400> SEQUENCE: 6
ugagguagua gauuguauag uu                                              22

<210> SEQ ID NO 7
<211> LENGTH: 22
<212> TYPE: RNA
<213> ORGANISM: Homo sapiens

<400> SEQUENCE: 7
ugagguagua guuguacag uu                                               22

<210> SEQ ID NO 8
<211> LENGTH: 22
<212> TYPE: RNA
<213> ORGANISM: Homo sapiens

<400> SEQUENCE: 8
ugagguagua guugugcug uu                                               22

<210> SEQ ID NO 9
<211> LENGTH: 22
<212> TYPE: RNA
<213> ORGANISM: Homo sapiens

<400> SEQUENCE: 9
aacccguaga uccgaacuug ug                                              22

<210> SEQ ID NO 10
<211> LENGTH: 23
<212> TYPE: RNA
<213> ORGANISM: Homo sapiens

<400> SEQUENCE: 10
agcagcauug uacagggcua uga                                             23

<210> SEQ ID NO 11
<211> LENGTH: 23
<212> TYPE: RNA
<213> ORGANISM: Homo sapiens

<400> SEQUENCE: 11
aaaagugcuu acagugcagg uag                                             23

<210> SEQ ID NO 12
<211> LENGTH: 23
```

```
<212> TYPE: RNA
<213> ORGANISM: Homo sapiens

<400> SEQUENCE: 12
agcagcauug uacagggcua uca                                    23

<210> SEQ ID NO 13
<211> LENGTH: 23
<212> TYPE: RNA
<213> ORGANISM: Homo sapiens

<400> SEQUENCE: 13
uacccuguag auccgaauuu gug                                    23

<210> SEQ ID NO 14
<211> LENGTH: 23
<212> TYPE: RNA
<213> ORGANISM: Homo sapiens

<400> SEQUENCE: 14
uacccuguag aaccgaauuu gug                                    23

<210> SEQ ID NO 15
<211> LENGTH: 22
<212> TYPE: RNA
<213> ORGANISM: Homo sapiens

<400> SEQUENCE: 15
uggaguguga caaugguguu ug                                     22

<210> SEQ ID NO 16
<211> LENGTH: 24
<212> TYPE: RNA
<213> ORGANISM: Homo sapiens

<400> SEQUENCE: 16
ucccugagac ccuuuaaccu guga                                   24

<210> SEQ ID NO 17
<211> LENGTH: 22
<212> TYPE: RNA
<213> ORGANISM: Homo sapiens

<400> SEQUENCE: 17
ucccugagac ccuaacuugu ga                                     22

<210> SEQ ID NO 18
<211> LENGTH: 22
<212> TYPE: RNA
<213> ORGANISM: Homo sapiens

<400> SEQUENCE: 18
ucguaccgug aguaauaaug cg                                     22

<210> SEQ ID NO 19
<211> LENGTH: 21
<212> TYPE: RNA
<213> ORGANISM: Homo sapiens

<400> SEQUENCE: 19
cauuauuacu uuugguacgc g                                      21

<210> SEQ ID NO 20
<211> LENGTH: 22
```

-continued

```
<212> TYPE: RNA
<213> ORGANISM: Homo sapiens

<400> SEQUENCE: 20
ucggauccgu cugagcuugg cu                                              22

<210> SEQ ID NO 21
<211> LENGTH: 21
<212> TYPE: RNA
<213> ORGANISM: Homo sapiens

<400> SEQUENCE: 21
ucacagugaa ccggucucuu u                                               21

<210> SEQ ID NO 22
<211> LENGTH: 21
<212> TYPE: RNA
<213> ORGANISM: Homo sapiens

<400> SEQUENCE: 22
cuuuuugcgg ucugggcuug c                                               21

<210> SEQ ID NO 23
<211> LENGTH: 22
<212> TYPE: RNA
<213> ORGANISM: Homo sapiens

<400> SEQUENCE: 23
uuuggucccc uucaaccagc ua                                              22

<210> SEQ ID NO 24
<211> LENGTH: 23
<212> TYPE: RNA
<213> ORGANISM: Homo sapiens

<400> SEQUENCE: 24
uauggcuuuu cauuccuaug uga                                             23

<210> SEQ ID NO 25
<211> LENGTH: 23
<212> TYPE: RNA
<213> ORGANISM: Homo sapiens

<400> SEQUENCE: 25
uuauugcuua agaauacgcg uag                                             23

<210> SEQ ID NO 26
<211> LENGTH: 22
<212> TYPE: RNA
<213> ORGANISM: Homo sapiens

<400> SEQUENCE: 26
uaacacuguc ugguaaagau gg                                              22

<210> SEQ ID NO 27
<211> LENGTH: 21
<212> TYPE: RNA
<213> ORGANISM: Homo sapiens

<400> SEQUENCE: 27
ugagaugaag cacguagcu c                                                21

<210> SEQ ID NO 28
<211> LENGTH: 23
```

```
<212> TYPE: RNA
<213> ORGANISM: Homo sapiens

<400> SEQUENCE: 28
guccaguuuu cccaggaauc ccu                                            23

<210> SEQ ID NO 29
<211> LENGTH: 22
<212> TYPE: RNA
<213> ORGANISM: Homo sapiens

<400> SEQUENCE: 29
ugagaacuga auuccauggg uu                                             22

<210> SEQ ID NO 30
<211> LENGTH: 22
<212> TYPE: RNA
<213> ORGANISM: Homo sapiens

<400> SEQUENCE: 30
ugagaacuga auuccauagg cu                                             22

<210> SEQ ID NO 31
<211> LENGTH: 22
<212> TYPE: RNA
<213> ORGANISM: Homo sapiens

<400> SEQUENCE: 31
ucagugcacu acagaacuuu gu                                             22

<210> SEQ ID NO 32
<211> LENGTH: 23
<212> TYPE: RNA
<213> ORGANISM: Homo sapiens

<400> SEQUENCE: 32
ucuggcuccg ugucuucacu ccc                                            23

<210> SEQ ID NO 33
<211> LENGTH: 22
<212> TYPE: RNA
<213> ORGANISM: Homo sapiens

<400> SEQUENCE: 33
ucucccaacc cuuguaccag ug                                             22

<210> SEQ ID NO 34
<211> LENGTH: 23
<212> TYPE: RNA
<213> ORGANISM: Homo sapiens

<400> SEQUENCE: 34
uuaaugcuaa ucgugauagg ggu                                            23

<210> SEQ ID NO 35
<211> LENGTH: 22
<212> TYPE: RNA
<213> ORGANISM: Homo sapiens

<400> SEQUENCE: 35
uagcagcaca uaaugguuug ug                                             22

<210> SEQ ID NO 36
<211> LENGTH: 22
```

```
<212> TYPE: RNA
<213> ORGANISM: Homo sapiens

<400> SEQUENCE: 36
uagcagcacg uaaauauugg cg                                          22

<210> SEQ ID NO 37
<211> LENGTH: 22
<212> TYPE: RNA
<213> ORGANISM: Homo sapiens

<400> SEQUENCE: 37
acugcaguga aggcacuugu ag                                          22

<210> SEQ ID NO 38
<211> LENGTH: 23
<212> TYPE: RNA
<213> ORGANISM: Homo sapiens

<400> SEQUENCE: 38
caaagugcuu acagugcagg uag                                         23

<210> SEQ ID NO 39
<211> LENGTH: 23
<212> TYPE: RNA
<213> ORGANISM: Homo sapiens

<400> SEQUENCE: 39
aacauucaac gcugucggug agu                                         23

<210> SEQ ID NO 40
<211> LENGTH: 23
<212> TYPE: RNA
<213> ORGANISM: Homo sapiens

<400> SEQUENCE: 40
aacauucauu gcugucggug ggu                                         23

<210> SEQ ID NO 41
<211> LENGTH: 22
<212> TYPE: RNA
<213> ORGANISM: Homo sapiens

<400> SEQUENCE: 41
aacauucaac cugucgguga gu                                          22

<210> SEQ ID NO 42
<211> LENGTH: 22
<212> TYPE: RNA
<213> ORGANISM: Homo sapiens

<400> SEQUENCE: 42
uauggcacug guagaauuca cu                                          22

<210> SEQ ID NO 43
<211> LENGTH: 22
<212> TYPE: RNA
<213> ORGANISM: Homo sapiens

<400> SEQUENCE: 43
uggacggaga acugauaagg gu                                          22

<210> SEQ ID NO 44
<211> LENGTH: 22
```

```
<212> TYPE: RNA
<213> ORGANISM: Homo sapiens

<400> SEQUENCE: 44
caaagaauuc uccuuuggg cu                                            22

<210> SEQ ID NO 45
<211> LENGTH: 22
<212> TYPE: RNA
<213> ORGANISM: Homo sapiens

<400> SEQUENCE: 45
ucgugucuug uguugcagcc gg                                           22

<210> SEQ ID NO 46
<211> LENGTH: 22
<212> TYPE: RNA
<213> ORGANISM: Homo sapiens

<400> SEQUENCE: 46
ugccuacuga gcugauauca gu                                           22

<210> SEQ ID NO 47
<211> LENGTH: 23
<212> TYPE: RNA
<213> ORGANISM: Homo sapiens

<400> SEQUENCE: 47
uaaggugcau cuagugcaga uag                                          23

<210> SEQ ID NO 48
<211> LENGTH: 22
<212> TYPE: RNA
<213> ORGANISM: Homo sapiens

<400> SEQUENCE: 48
ugauauguuu gauauauuag gu                                           22

<210> SEQ ID NO 49
<211> LENGTH: 23
<212> TYPE: RNA
<213> ORGANISM: Homo sapiens

<400> SEQUENCE: 49
caacggaauc ccaaaagcag cug                                          23

<210> SEQ ID NO 50
<211> LENGTH: 21
<212> TYPE: RNA
<213> ORGANISM: Homo sapiens

<400> SEQUENCE: 50
cugaccuaug aauugacagc c                                            21

<210> SEQ ID NO 51
<211> LENGTH: 21
<212> TYPE: RNA
<213> ORGANISM: Homo sapiens

<400> SEQUENCE: 51
uagcagcaca gaaauauugg c                                            21

<210> SEQ ID NO 52
<211> LENGTH: 22
```

```
<212> TYPE: RNA
<213> ORGANISM: Homo sapiens

<400> SEQUENCE: 52
uucaccaccu ucuccaccca gc                                              22

<210> SEQ ID NO 53
<211> LENGTH: 23
<212> TYPE: RNA
<213> ORGANISM: Homo sapiens

<400> SEQUENCE: 53
cccaguguuc agacuaccug uuc                                             23

<210> SEQ ID NO 54
<211> LENGTH: 22
<212> TYPE: RNA
<213> ORGANISM: Homo sapiens

<400> SEQUENCE: 54
acaguagucu gcacauuggu ua                                              22

<210> SEQ ID NO 55
<211> LENGTH: 23
<212> TYPE: RNA
<213> ORGANISM: Homo sapiens

<400> SEQUENCE: 55
ugugcaaauc uaugcaaaac uga                                             23

<210> SEQ ID NO 56
<211> LENGTH: 23
<212> TYPE: RNA
<213> ORGANISM: Homo sapiens

<400> SEQUENCE: 56
ugugcaaauc caugcaaaac uga                                             23

<210> SEQ ID NO 57
<211> LENGTH: 22
<212> TYPE: RNA
<213> ORGANISM: Homo sapiens

<400> SEQUENCE: 57
uaacacuguc ugguaacgau gu                                              22

<210> SEQ ID NO 58
<211> LENGTH: 22
<212> TYPE: RNA
<213> ORGANISM: Homo sapiens

<400> SEQUENCE: 58
caucuuaccg gacagugcug ga                                              22

<210> SEQ ID NO 59
<211> LENGTH: 22
<212> TYPE: RNA
<213> ORGANISM: Homo sapiens

<400> SEQUENCE: 59
uaauacugcc ugguaaugau ga                                              22

<210> SEQ ID NO 60
<211> LENGTH: 23
```

<212> TYPE: RNA
<213> ORGANISM: Homo sapiens

<400> SEQUENCE: 60
uaauacugcc ggguaaugau gga                                    23

<210> SEQ ID NO 61
<211> LENGTH: 20
<212> TYPE: RNA
<213> ORGANISM: Homo sapiens

<400> SEQUENCE: 61
agagguauag ggcaugggaa                                        20

<210> SEQ ID NO 62
<211> LENGTH: 22
<212> TYPE: RNA
<213> ORGANISM: Homo sapiens

<400> SEQUENCE: 62
gugaaauguu uaggaccacu ag                                     22

<210> SEQ ID NO 63
<211> LENGTH: 22
<212> TYPE: RNA
<213> ORGANISM: Homo sapiens

<400> SEQUENCE: 63
uccuucauuc caccggaguc ug                                     22

<210> SEQ ID NO 64
<211> LENGTH: 23
<212> TYPE: RNA
<213> ORGANISM: Homo sapiens

<400> SEQUENCE: 64
uaaagugcuu auagugcagg uag                                    23

<210> SEQ ID NO 65
<211> LENGTH: 22
<212> TYPE: RNA
<213> ORGANISM: Homo sapiens

<400> SEQUENCE: 65
uagcuuauca gacugauguu ga                                     22

<210> SEQ ID NO 66
<211> LENGTH: 22
<212> TYPE: RNA
<213> ORGANISM: Homo sapiens

<400> SEQUENCE: 66
cugugcgugu gacagcggcu ga                                     22

<210> SEQ ID NO 67
<211> LENGTH: 22
<212> TYPE: RNA
<213> ORGANISM: Homo sapiens

<400> SEQUENCE: 67
uaaucucagc uggcaacugu ga                                     22

<210> SEQ ID NO 68
<211> LENGTH: 21

```
<212> TYPE: RNA
<213> ORGANISM: Homo sapiens

<400> SEQUENCE: 68
uugugcuuga ucuaaccaug u                                          21

<210> SEQ ID NO 69
<211> LENGTH: 22
<212> TYPE: RNA
<213> ORGANISM: Homo sapiens

<400> SEQUENCE: 69
aagcugccag uugaagaacu gu                                         22

<210> SEQ ID NO 70
<211> LENGTH: 23
<212> TYPE: RNA
<213> ORGANISM: Homo sapiens

<400> SEQUENCE: 70
agcuacauug ucugcugggu uuc                                        23

<210> SEQ ID NO 71
<211> LENGTH: 21
<212> TYPE: RNA
<213> ORGANISM: Homo sapiens

<400> SEQUENCE: 71
agcuacaucu ggcuacuggg u                                          21

<210> SEQ ID NO 72
<211> LENGTH: 22
<212> TYPE: RNA
<213> ORGANISM: Homo sapiens

<400> SEQUENCE: 72
ugucaguuug ucaaauaccc ca                                         22

<210> SEQ ID NO 73
<211> LENGTH: 21
<212> TYPE: RNA
<213> ORGANISM: Homo sapiens

<400> SEQUENCE: 73
caagucacua gugguuccgu u                                          21

<210> SEQ ID NO 74
<211> LENGTH: 21
<212> TYPE: RNA
<213> ORGANISM: Homo sapiens

<400> SEQUENCE: 74
aucacauugc cagggauuuc c                                          21

<210> SEQ ID NO 75
<211> LENGTH: 21
<212> TYPE: RNA
<213> ORGANISM: Homo sapiens

<400> SEQUENCE: 75
aucacauugc cagggauuac c                                          21

<210> SEQ ID NO 76
<211> LENGTH: 22
```

```
<212> TYPE: RNA
<213> ORGANISM: Homo sapiens

<400> SEQUENCE: 76
uggcucaguu cagcaggaac ag                                              22

<210> SEQ ID NO 77
<211> LENGTH: 22
<212> TYPE: RNA
<213> ORGANISM: Homo sapiens

<400> SEQUENCE: 77
cauugcacuu gucucggucu ga                                              22

<210> SEQ ID NO 78
<211> LENGTH: 22
<212> TYPE: RNA
<213> ORGANISM: Homo sapiens

<400> SEQUENCE: 78
uucaaguaau ccaggauagg cu                                              22

<210> SEQ ID NO 79
<211> LENGTH: 21
<212> TYPE: RNA
<213> ORGANISM: Homo sapiens

<400> SEQUENCE: 79
uucaaguaau ucaggauagg u                                               21

<210> SEQ ID NO 80
<211> LENGTH: 21
<212> TYPE: RNA
<213> ORGANISM: Homo sapiens

<400> SEQUENCE: 80
uucacagugg cuaaguuccg c                                               21

<210> SEQ ID NO 81
<211> LENGTH: 21
<212> TYPE: RNA
<213> ORGANISM: Homo sapiens

<400> SEQUENCE: 81
uucacagugg cuaaguucug c                                               21

<210> SEQ ID NO 82
<211> LENGTH: 22
<212> TYPE: RNA
<213> ORGANISM: Homo sapiens

<400> SEQUENCE: 82
uagcaccauc ugaaaucggu ua                                              22

<210> SEQ ID NO 83
<211> LENGTH: 23
<212> TYPE: RNA
<213> ORGANISM: Homo sapiens

<400> SEQUENCE: 83
uagcaccauu ugaaaucagu guu                                             23

<210> SEQ ID NO 84
<211> LENGTH: 21
```

```
<212> TYPE: RNA
<213> ORGANISM: Homo sapiens

<400> SEQUENCE: 84
agggcccccc cucaauccug u                                              21

<210> SEQ ID NO 85
<211> LENGTH: 23
<212> TYPE: RNA
<213> ORGANISM: Homo sapiens

<400> SEQUENCE: 85
cagugcaaua guauugucaa agc                                            23

<210> SEQ ID NO 86
<211> LENGTH: 23
<212> TYPE: RNA
<213> ORGANISM: Homo sapiens

<400> SEQUENCE: 86
uaagugcuuc cauguuuugg uga                                            23

<210> SEQ ID NO 87
<211> LENGTH: 23
<212> TYPE: RNA
<213> ORGANISM: Homo sapiens

<400> SEQUENCE: 87
acuuaaacgu ggauguacuu gcu                                            23

<210> SEQ ID NO 88
<211> LENGTH: 22
<212> TYPE: RNA
<213> ORGANISM: Homo sapiens

<400> SEQUENCE: 88
uguaaacauc cucgacugga ag                                             22

<210> SEQ ID NO 89
<211> LENGTH: 22
<212> TYPE: RNA
<213> ORGANISM: Homo sapiens

<400> SEQUENCE: 89
uguaaacauc cuacacucag cu                                             22

<210> SEQ ID NO 90
<211> LENGTH: 23
<212> TYPE: RNA
<213> ORGANISM: Homo sapiens

<400> SEQUENCE: 90
uguaaacauc cuacacucuc agc                                            23

<210> SEQ ID NO 91
<211> LENGTH: 22
<212> TYPE: RNA
<213> ORGANISM: Homo sapiens

<400> SEQUENCE: 91
uguaaacauc cccgacugga ag                                             22

<210> SEQ ID NO 92
<211> LENGTH: 22
```

```
<212> TYPE: RNA
<213> ORGANISM: Homo sapiens

<400> SEQUENCE: 92
cuuucagucg gauguuuaca gc                                        22

<210> SEQ ID NO 93
<211> LENGTH: 22
<212> TYPE: RNA
<213> ORGANISM: Homo sapiens

<400> SEQUENCE: 93
uguaaacauc cuugacugga ag                                        22

<210> SEQ ID NO 94
<211> LENGTH: 21
<212> TYPE: RNA
<213> ORGANISM: Homo sapiens

<400> SEQUENCE: 94
aggcaagaug cuggcauagc u                                         21

<210> SEQ ID NO 95
<211> LENGTH: 22
<212> TYPE: RNA
<213> ORGANISM: Homo sapiens

<400> SEQUENCE: 95
aaaagcuggg uugagagggc ga                                        22

<210> SEQ ID NO 96
<211> LENGTH: 21
<212> TYPE: RNA
<213> ORGANISM: Homo sapiens

<400> SEQUENCE: 96
cacauuacac ggucgaccuc u                                         21

<210> SEQ ID NO 97
<211> LENGTH: 23
<212> TYPE: RNA
<213> ORGANISM: Homo sapiens

<400> SEQUENCE: 97
cgcaucsccu agggcauugg ugu                                       23

<210> SEQ ID NO 98
<211> LENGTH: 20
<212> TYPE: RNA
<213> ORGANISM: Homo sapiens

<400> SEQUENCE: 98
ccucugggcc cuuccuccag                                           20

<210> SEQ ID NO 99
<211> LENGTH: 23
<212> TYPE: RNA
<213> ORGANISM: Homo sapiens

<400> SEQUENCE: 99
gcaaagcaca cggccugcag aga                                       23

<210> SEQ ID NO 100
<211> LENGTH: 21
```

```
<212> TYPE: RNA
<213> ORGANISM: Homo sapiens

<400> SEQUENCE: 100
gccccugggc cuauccuaga a                                           21

<210> SEQ ID NO 101
<211> LENGTH: 23
<212> TYPE: RNA
<213> ORGANISM: Homo sapiens

<400> SEQUENCE: 101
ucaagagcaa uaacgaaaaa ugu                                         23

<210> SEQ ID NO 102
<211> LENGTH: 23
<212> TYPE: RNA
<213> ORGANISM: Homo sapiens

<400> SEQUENCE: 102
ugucugcccg caugccugcc ucu                                         23

<210> SEQ ID NO 103
<211> LENGTH: 22
<212> TYPE: RNA
<213> ORGANISM: Homo sapiens

<400> SEQUENCE: 103
uggcaguguc uuagcugguu gu                                          22

<210> SEQ ID NO 104
<211> LENGTH: 22
<212> TYPE: RNA
<213> ORGANISM: Homo sapiens

<400> SEQUENCE: 104
gccugcuggg guggaaccug gu                                          22

<210> SEQ ID NO 105
<211> LENGTH: 23
<212> TYPE: RNA
<213> ORGANISM: Homo sapiens

<400> SEQUENCE: 105
aaagugcugc gacauuugag cgu                                         23

<210> SEQ ID NO 106
<211> LENGTH: 23
<212> TYPE: RNA
<213> ORGANISM: Homo sapiens

<400> SEQUENCE: 106
gaagugcuuc gauuuugggg ugu                                         23

<210> SEQ ID NO 107
<211> LENGTH: 22
<212> TYPE: RNA
<213> ORGANISM: Homo sapiens

<400> SEQUENCE: 107
acucaaaaug ggggcgcuuu cc                                          22

<210> SEQ ID NO 108
<211> LENGTH: 21
```

```
<212> TYPE: RNA
<213> ORGANISM: Homo sapiens

<400> SEQUENCE: 108
cagcagcaca cugugguuug u                                              21

<210> SEQ ID NO 109
<211> LENGTH: 23
<212> TYPE: RNA
<213> ORGANISM: Homo sapiens

<400> SEQUENCE: 109
uuucaagcca gggggcguuu uuc                                            23

<210> SEQ ID NO 110
<211> LENGTH: 23
<212> TYPE: RNA
<213> ORGANISM: Homo sapiens

<400> SEQUENCE: 110
uagcagcggg aacaguucug cag                                            23

<210> SEQ ID NO 111
<211> LENGTH: 22
<212> TYPE: RNA
<213> ORGANISM: Homo sapiens

<400> SEQUENCE: 111
uauugcacuu gucccggccu gu                                             22

<210> SEQ ID NO 112
<211> LENGTH: 23
<212> TYPE: RNA
<213> ORGANISM: Homo sapiens

<400> SEQUENCE: 112
caaagugcug uucgugcagg uag                                            23

<210> SEQ ID NO 113
<211> LENGTH: 23
<212> TYPE: RNA
<213> ORGANISM: Homo sapiens

<400> SEQUENCE: 113
uuuggcacua gcacauuuuu gcu                                            23

<210> SEQ ID NO 114
<211> LENGTH: 22
<212> TYPE: RNA
<213> ORGANISM: Homo sapiens

<400> SEQUENCE: 114
aacccguaga uccgaucuug ug                                             22

<210> SEQ ID NO 115
<211> LENGTH: 80
<212> TYPE: RNA
<213> ORGANISM: Homo sapiens

<400> SEQUENCE: 115
ugggaugagg uaguagguug uauaguuuua gggucacacc caccacuggg agauaacuau    60
acaaucuacu gucuuuccua                                                80
```

```
<210> SEQ ID NO 116
<211> LENGTH: 72
<212> TYPE: RNA
<213> ORGANISM: Homo sapiens

<400> SEQUENCE: 116
agguugaggu aguagguugu auaguuuaga auuacaucaa gggagauaac uguacagccu    60
ccuagcuuuc cu                                                        72

<210> SEQ ID NO 117
<211> LENGTH: 74
<212> TYPE: RNA
<213> ORGANISM: Homo sapiens

<400> SEQUENCE: 117
gggugaggua guagguugua aguuugggg cucugcccug cuaugggaua acuauacaau     60
cuacugucuu uccu                                                      74

<210> SEQ ID NO 118
<211> LENGTH: 83
<212> TYPE: RNA
<213> ORGANISM: Homo sapiens

<400> SEQUENCE: 118
cggggugagg uaguagguug ugugguuuca gggcagugau uugcccuc ggaagauaac      60 uauacaaccu acugccuucc cug                                            83

<210> SEQ ID NO 119
<211> LENGTH: 84
<212> TYPE: RNA
<213> ORGANISM: Homo sapiens

<400> SEQUENCE: 119
gcauccgggu ugagguagua ggungugaugg uuuagaguua cacccuggga guuaacugua   60
caaccuucua gcuuuccuug gagc                                           84

<210> SEQ ID NO 120
<211> LENGTH: 87
<212> TYPE: RNA
<213> ORGANISM: Homo sapiens

<400> SEQUENCE: 120
ccuaggaaga gguaguaggu ugcauaguuu uagggcaggg auuuugccca caaggaggua    60
acuauacgac cugcugccuu ucuuagg                                        87

<210> SEQ ID NO 121
<211> LENGTH: 79
<212> TYPE: RNA
<213> ORGANISM: Homo sapiens

<400> SEQUENCE: 121
cccgggcuga gguaggaggu uguauaguug aggaggacac ccaaggagau cacuauacgg    60
ccuccuagcu uucccagg                                                  79

<210> SEQ ID NO 122
<211> LENGTH: 87
<212> TYPE: RNA
<213> ORGANISM: Homo sapiens

<400> SEQUENCE: 122
ucagagugag guaguagauu guauaguugu gggguaguga uuuuacccug uucaggagau    60
```

-continued

```
aacuauacaa ucuauugccu ucccuga                                                87

<210> SEQ ID NO 123
<211> LENGTH: 83
<212> TYPE: RNA
<213> ORGANISM: Homo sapiens

<400> SEQUENCE: 123
ugugggauga gguaguagau uguauaguuu uagggucaua ccccaucuug gagauaacua            60
uacagucuac ugucuuuccc acg                                                   83

<210> SEQ ID NO 124
<211> LENGTH: 84
<212> TYPE: RNA
<213> ORGANISM: Homo sapiens

<400> SEQUENCE: 124
aggcugaggu aguaguuugu acaguuugag ggucuaugau accacccggu acaggagaua           60
acuguacagg ccacugccuu gcca                                                  84

<210> SEQ ID NO 125
<211> LENGTH: 84
<212> TYPE: RNA
<213> ORGANISM: Homo sapiens

<400> SEQUENCE: 125
cuggcugagg uaguaguuug ugcuguuggu cggguuguga cauugcccgc uguggagaua           60
acugcgcaag cuacugccuu gcua                                                  84

<210> SEQ ID NO 126
<211> LENGTH: 80
<212> TYPE: RNA
<213> ORGANISM: Homo sapiens

<400> SEQUENCE: 126
ccuguugcca caaacccgua gauccgaacu ugugguauua guccgcacaa gcuuguaucu           60
auagguaugu gucuguuagg                                                       80

<210> SEQ ID NO 127
<211> LENGTH: 78
<212> TYPE: RNA
<213> ORGANISM: Homo sapiens

<400> SEQUENCE: 127
uacugcccuc ggcuucuuua cagugcugcc uuguugcaua uggaucaagc agcauuguac           60
agggcuauga aggcauug                                                         78

<210> SEQ ID NO 128
<211> LENGTH: 78
<212> TYPE: RNA
<213> ORGANISM: Homo sapiens

<400> SEQUENCE: 128
uugugcuuuc agcuucuuua cagugcugcc uuguagcauu caggucaagc agcauuguac           60
agggcuauga aagaacca                                                         78

<210> SEQ ID NO 129
<211> LENGTH: 81
<212> TYPE: RNA
<213> ORGANISM: Homo sapiens
```

<400> SEQUENCE: 129
ccuuggccau guaaaagugc uuacagugca gguagcuuuu ugagaucuac ugcaauguaa    60
gcacuucuua cauuaccaug g                                             81

<210> SEQ ID NO 130
<211> LENGTH: 81
<212> TYPE: RNA
<213> ORGANISM: Homo sapiens

<400> SEQUENCE: 130
cucucugcuu ucagcuucuu uacaguguug ccuguggca uggaguucaa gcagcauugu    60
acagggcuau caaagcacag a                                             81

<210> SEQ ID NO 131
<211> LENGTH: 110
<212> TYPE: RNA
<213> ORGANISM: Homo sapiens

<400> SEQUENCE: 131
gaucugucug ucuucuguau auaccccugua gauccgaauu uguguaagga auuuuguggu    60
cacaaauucg uaucuagggg aauauguagu ugacauaaac acuccgcucu              110

<210> SEQ ID NO 132
<211> LENGTH: 110
<212> TYPE: RNA
<213> ORGANISM: Homo sapiens

<400> SEQUENCE: 132
ccagagguug uaacguuguc uauauauacc cuguagaacc gaauuugugu ggguauccgua   60 uagucacaga uucgauucua ggggaauaua uggucgaugc aaaaacuuca              110

<210> SEQ ID NO 133
<211> LENGTH: 85
<212> TYPE: RNA
<213> ORGANISM: Homo sapiens

<400> SEQUENCE: 133
ccuuagcaga gcuguggagu ugacaaugg uguuugguc uaaacuauca aacgccauua      60
ucacacuaaa uagcuacugc uaggc                                         85

<210> SEQ ID NO 134
<211> LENGTH: 86
<212> TYPE: RNA
<213> ORGANISM: Homo sapiens

<400> SEQUENCE: 134
ugccagucuc uagguccccug agacccuuua accgugagg acauccaggg ucacagguga    60
gguucuuggg agccuggcgu cuggcc                                        86

<210> SEQ ID NO 135
<211> LENGTH: 88
<212> TYPE: RNA
<213> ORGANISM: Homo sapiens

<400> SEQUENCE: 135
ugcgcuccuc ucagucccug agacccuaac uugugauguu uaccguuuaa auccacgggu    60
uaggcucuug ggagcugcga gucgugcu                                      88

```
<210> SEQ ID NO 136
<211> LENGTH: 89
<212> TYPE: RNA
<213> ORGANISM: Homo sapiens

<400> SEQUENCE: 136
accagacuuu ccuaguccc ugagacccua acuugugagg uauuuuagua acaucacaag      60
ucaggcucuu gggaccuagg cggagggga                                      89

<210> SEQ ID NO 137
<211> LENGTH: 85
<212> TYPE: RNA
<213> ORGANISM: Homo sapiens

<400> SEQUENCE: 137
cgcuggcgac gggacauuau uacuuuuggu acgcgcugug acacuucaaa cucguaccgu     60
gaguaauaau gcgccgucca cggca                                          85

<210> SEQ ID NO 138
<211> LENGTH: 97
<212> TYPE: RNA
<213> ORGANISM: Homo sapiens

<400> SEQUENCE: 138
ugugaucacu gucuccagcc ugcugaagcu cagagggcuc ugauucagaa agaucaucgg     60
auccgucuga gcuuggcugg ucggaagucu caucauc                             97

<210> SEQ ID NO 139
<211> LENGTH: 82
<212> TYPE: RNA
<213> ORGANISM: Homo sapiens

<400> SEQUENCE: 139
ugagcuguug gauucggggc cguagcacug ucugagaggu uuacauuucu cacagugaac     60
cggucucuuu uucagcugcu uc                                             82

<210> SEQ ID NO 140
<211> LENGTH: 72
<212> TYPE: RNA
<213> ORGANISM: Homo sapiens

<400> SEQUENCE: 140
ggaucuuuuu gcggucuggg cuugcuguuc cucucaacag uagucaggaa gcccuuaccc     60
caaaaaguau cu                                                        72

<210> SEQ ID NO 141
<211> LENGTH: 90
<212> TYPE: RNA
<213> ORGANISM: Homo sapiens

<400> SEQUENCE: 141
ugcccuucgc gaaucuuuuu gcggucuggg cuugcuguac auaacucaau agccggaagc     60 ccuuaccca aaaagcauuu gcggagggcg                                      90

<210> SEQ ID NO 142
<211> LENGTH: 119
<212> TYPE: RNA
<213> ORGANISM: Homo sapiens

<400> SEQUENCE: 142
ccucagaaga aagaugcccc cugcucuggc uggucaaacg gaaccaaguc cgucuuccug     60
```
agagguuugg uccccuucaa ccagcuacag cagggcuggc aaugcccagu ccuuggaga        119

<210> SEQ ID NO 143
<211> LENGTH: 97
<212> TYPE: RNA
<213> ORGANISM: Homo sapiens

<400> SEQUENCE: 143
cacucugcug uggccuaugg cuuuucauuc cuaugugauu gcugucccaa acucauguag        60
ggcuaaaagc caugggcuac agugaggggc gagcucc                                97

<210> SEQ ID NO 144
<211> LENGTH: 102
<212> TYPE: RNA
<213> ORGANISM: Homo sapiens

<400> SEQUENCE: 144
gguccucuga cucucuucgg ugacgggaua ucuuggugg auaauacgga uuacguuguu        60
auugcuuaag aauacgcgua gucgaggaga guaccagcgg ca                         102

<210> SEQ ID NO 145
<211> LENGTH: 95
<212> TYPE: RNA
<213> ORGANISM: Homo sapiens

<400> SEQUENCE: 145
cggccggccc ugguccauc uuccaguaca guguuggaug gucuaauugu gaagcuccua        60
acacugucug guaaagaugg cucccgggug gguuc                                 95

<210> SEQ ID NO 146
<211> LENGTH: 106
<212> TYPE: RNA
<213> ORGANISM: Homo sapiens

<400> SEQUENCE: 146
gcgcagcgcc cugucuccca gccugaggug cagugcugca ucucugguca guugggaguc        60
ugagaugaag cacuguagcu caggaagaga gaaguuguuc ugcagc                     106

<210> SEQ ID NO 147
<211> LENGTH: 88
<212> TYPE: RNA
<213> ORGANISM: Homo sapiens

<400> SEQUENCE: 147
caccuugucc ucacggucca guuucccag gaaucccuua gaugcuaaga uggggauucc         60
uggaaauacu guucuugagg ucaugguu                                          88

<210> SEQ ID NO 148
<211> LENGTH: 99
<212> TYPE: RNA
<213> ORGANISM: Homo sapiens

<400> SEQUENCE: 148
ccgaugugua uccucagcuu ugagaacuga auuccauggg uugugucagu gucagaccuc        60
ugaaauucag uucuucagcu gggauaucuc ugcaucgu                              99

<210> SEQ ID NO 149
<211> LENGTH: 73
<212> TYPE: RNA
<213> ORGANISM: Homo sapiens

<400> SEQUENCE: 149
ccuggcacug agaacugaau uccauaggcu gugagcucua gcaaugcccu guggacucag    60
uucuggugcc cgg    73

<210> SEQ ID NO 150
<211> LENGTH: 68
<212> TYPE: RNA
<213> ORGANISM: Homo sapiens

<400> SEQUENCE: 150
gaggcaaagu ucugagacac uccgacucug aguaugauag aagucagugc acuacagaac    60
uuugucuc    68

<210> SEQ ID NO 151
<211> LENGTH: 89
<212> TYPE: RNA
<213> ORGANISM: Homo sapiens

<400> SEQUENCE: 151
gccggcgccc gagcucuggc uccgugucuu cacucccgug cuuguccgag gagggaggga    60
gggacggggg cugugcuggg gcagcugga    89

<210> SEQ ID NO 152
<211> LENGTH: 84
<212> TYPE: RNA
<213> ORGANISM: Homo sapiens

<400> SEQUENCE: 152
cuccccaugg cccugucucc caacccuugu accagugcug ggcucagacc cugguacagg    60 ccuggggac agggaccugg ggac    84

<210> SEQ ID NO 153
<211> LENGTH: 65
<212> TYPE: RNA
<213> ORGANISM: Homo sapiens

<400> SEQUENCE: 153
cuguuaaugc uaaucgugau agggguuuuu gccuccaacu gacuccuaca uauuagcauu    60
aacag    65

<210> SEQ ID NO 154
<211> LENGTH: 83
<212> TYPE: RNA
<213> ORGANISM: Homo sapiens

<400> SEQUENCE: 154 ccuggagua aaguagcagc acauaauggu uugguggauuu ugaaaaggug caggccauau    60
ugugcugccu caaaaauaca agg    83

<210> SEQ ID NO 155
<211> LENGTH: 89
<212> TYPE: RNA
<213> ORGANISM: Homo sapiens

<400> SEQUENCE: 155
gucagcagug ccuuagcagc acguaaauau uggcguuaag auucuaaaau uaucccagu    60 auuaacugug cugcugaagu aagguugac    89

```
<210> SEQ ID NO 156
<211> LENGTH: 81
<212> TYPE: RNA
<213> ORGANISM: Homo sapiens

<400> SEQUENCE: 156
guuccacucu agcagcacgu aaauauuggc guagugaaau auauauuaaa caccaauauu     60
acugugcugc uuuaguguga c                                              81

<210> SEQ ID NO 157
<211> LENGTH: 84
<212> TYPE: RNA
<213> ORGANISM: Homo sapiens

<400> SEQUENCE: 157
gucagaauaa ugucaaagug cuuacagugc agguagugau augugcaucu acugcaguga    60
aggcacuugu agcauuaugg ugac                                           84

<210> SEQ ID NO 158
<211> LENGTH: 110
<212> TYPE: RNA
<213> ORGANISM: Homo sapiens

<400> SEQUENCE: 158
ugaguuuuga gguugcuuca gugaacauuc aacgcugucg gugaguuugg aauuaaaauc    60
aaaaccaucg accguugauu guaccccuaug gcuaaccauc aucacucca               110

<210> SEQ ID NO 159
<211> LENGTH: 110
<212> TYPE: RNA
<213> ORGANISM: Homo sapiens

<400> SEQUENCE: 159
agaagggcua ucaggccagc cuucagagga cuccaaggaa cauucaacgc ugucggugag    60
uuugggauuu gaaaaaacca cugaccguug acuguaccuu gggguccuua               110

<210> SEQ ID NO 160
<211> LENGTH: 110
<212> TYPE: RNA
<213> ORGANISM: Homo sapiens

<400> SEQUENCE: 160
ccugugcaga gauuauuuuu uaaaagguca caaucaacau ucauugcugu cgguggguug    60
aacugugugg acaagcucac ugaacaauga augcaacugu ggccccgcuu               110

<210> SEQ ID NO 161
<211> LENGTH: 89
<212> TYPE: RNA
<213> ORGANISM: Homo sapiens

<400> SEQUENCE: 161
cugauggcug cacucaacau ucauugcugu cggugguuu gagucugaau caacucacug     60
aucaaugaau gcaaacugcg gaccaaaca                                      89

<210> SEQ ID NO 162
<211> LENGTH: 110
<212> TYPE: RNA
<213> ORGANISM: Homo sapiens

<400> SEQUENCE: 162
cggaaaauuu gccaagggu uggggaaca uucaaccugu cggugaguuu gggcagcuca      60
```

```
ggcaaaccau cgaccguuga guggacccug aggccuggaa uugccauccu         110

<210> SEQ ID NO 163
<211> LENGTH: 110
<212> TYPE: RNA
<213> ORGANISM: Homo sapiens

<400> SEQUENCE: 163
ccgcagagug ugacuccugu ucuguguaug gcacugguag aauucacugu gaacagucuc  60
agucagugaa uuaccgaagg gccauaaaca gagcagagac agauccacga             110

<210> SEQ ID NO 164
<211> LENGTH: 84
<212> TYPE: RNA
<213> ORGANISM: Homo sapiens

<400> SEQUENCE: 164
ccagucacgu ccccuuauca cuuuuccagc ccagcuuugu gacuguaagu guuggacgga  60
gaacugauaa ggguagguga uuga                                         84

<210> SEQ ID NO 165
<211> LENGTH: 86
<212> TYPE: RNA
<213> ORGANISM: Homo sapiens

<400> SEQUENCE: 165
ugcuuguaac uuuccaaaga auucuccuuu ugggcuuucu gguuuauuuu uaagcccaaa  60
ggugaauuuu uugggaaguu ugagcu                                       86

<210> SEQ ID NO 166
<211> LENGTH: 109
<212> TYPE: RNA
<213> ORGANISM: Homo sapiens

<400> SEQUENCE: 166
ggucgggcuc accaugacac agugugagac cucgggcuac aacacaggac ccgggcgcug  60 cucugaccccc ucgugucuug uguugcagcc ggagggacgc agguccgca            109

<210> SEQ ID NO 167
<211> LENGTH: 71
<212> TYPE: RNA
<213> ORGANISM: Homo sapiens

<400> SEQUENCE: 167
uguucuaagg ugcaucuagu gcagauagug aaguagauua gcaucuacug cccuaagugc  60
uccuucuggc a                                                       71

<210> SEQ ID NO 168
<211> LENGTH: 85
<212> TYPE: RNA
<213> ORGANISM: Homo sapiens

<400> SEQUENCE: 168
ugcaggccuc ugugugauau guuugauaua uuagguuguu auuuaauccu acuauauauc  60
aaacauauuc cuacaguguc uugcc                                        85

<210> SEQ ID NO 169
<211> LENGTH: 92
<212> TYPE: RNA
<213> ORGANISM: Homo sapiens
```

```
<400> SEQUENCE: 169
cggcuggaca gcgggcaacg gaaucccaaa agcagcuguu gucuccagag cauuccagcu    60
gcgcuuggau uucguccccu gcucuccugc cu                                  92

<210> SEQ ID NO 170
<211> LENGTH: 110
<212> TYPE: RNA
<213> ORGANISM: Homo sapiens

<400> SEQUENCE: 170
gccgagaccg agugcacagg gcucugaccu augaauugac agccagugcu cucgucucc    60 cucuggcugc caauuccaua ggucacaggu auguucgccu caaugccagc              110

<210> SEQ ID NO 171
<211> LENGTH: 87
<212> TYPE: RNA
<213> ORGANISM: Homo sapiens

<400> SEQUENCE: 171
agcuucccug gcucuagcag cacagaaaua uuggcacagg gaagcgaguc ugccaauauu    60
ggcugugcug cuccaggcag gguggug                                        87

<210> SEQ ID NO 172
<211> LENGTH: 75
<212> TYPE: RNA
<213> ORGANISM: Homo sapiens

<400> SEQUENCE: 172
ggcugugccg gguagagagg gcagugggag guaagagcuc uucacccuuc accaccuucu    60
ccacccagca uggcc                                                     75

<210> SEQ ID NO 173
<211> LENGTH: 71
<212> TYPE: RNA
<213> ORGANISM: Homo sapiens

<400> SEQUENCE: 173
gccaacccag uguucagacu accuguucag gaggcucuca auguguacag uagucugcac    60
auugguuagg c                                                         71

<210> SEQ ID NO 174
<211> LENGTH: 110
<212> TYPE: RNA
<213> ORGANISM: Homo sapiens

<400> SEQUENCE: 174
aggaagcuuc uggagauccu gcuccgucgc cccagugeuc agacuaccug uucaggacaa    60
ugccguugua caguagucug cacauugguu agacugggca agggagagca              110

<210> SEQ ID NO 175
<211> LENGTH: 82
<212> TYPE: RNA
<213> ORGANISM: Homo sapiens

<400> SEQUENCE: 175
gcagcccucu guuaguuuug cauaguugca cuacaagaag aauguaguug ugcaaaucua    60
ugcaaaacug augguggccu gc                                             82
```

```
<210> SEQ ID NO 176
<211> LENGTH: 87
<212> TYPE: RNA
<213> ORGANISM: Homo sapiens

<400> SEQUENCE: 176
cacuguucua gguuaguuu ugcagguuug cauccagcug ugugauauuc ugcugugcaa    60
auccaugcaa aacgacugu gguagug                                       87

<210> SEQ ID NO 177
<211> LENGTH: 96
<212> TYPE: RNA
<213> ORGANISM: Homo sapiens

<400> SEQUENCE: 177
acauugcuac uuacaauuag uuuugcaggu uugcauuuca gcguauauau guauaugugg    60
cugugcaaau ccaugcaaaa cugauuguga uaaugu                             96

<210> SEQ ID NO 178
<211> LENGTH: 90
<212> TYPE: RNA
<213> ORGANISM: Homo sapiens

<400> SEQUENCE: 178 ccgggcccu gugagcaucu uaccggacag ugcuggauuu cccagcuuga cucuaacacu    60
gucugguaac gauguucaaa ggugacccgc                                    90

<210> SEQ ID NO 179
<211> LENGTH: 95
<212> TYPE: RNA
<213> ORGANISM: Homo sapiens

<400> SEQUENCE: 179
ccagcucggg cagccguggc caucuuacug ggcagcauug gauggaguca ggucucuaau    60
acugccuggu aaugaugacg gcggagcccu gcacg                              95

<210> SEQ ID NO 180
<211> LENGTH: 68
<212> TYPE: RNA
<213> ORGANISM: Homo sapiens

<400> SEQUENCE: 180
cccucgucuu acccagcagu guuggguugc gguuggagu cucuaauacu gccggguaau     60
gauggagg                                                            68

<210> SEQ ID NO 181
<211> LENGTH: 110
<212> TYPE: RNA
<213> ORGANISM: Homo sapiens

<400> SEQUENCE: 181
cgccucagag ccgcccgccg uuccuuuuuc cuaugcauau acuucuuuga ggaucuggcc    60
uaaagaggua uagggcaugg gaaacggggg cggucgdgguc cuccccagcg              110

<210> SEQ ID NO 182
<211> LENGTH: 110
<212> TYPE: RNA
<213> ORGANISM: Homo sapiens

<400> SEQUENCE: 182
guguugggga cucgcgcgcu gggucccagug guucuuaaca guucaacagu ucuguagcgc    60
```

```
aauugugaaa uguuuaggac cacuagaccc ggcgggcgcg gcgacagcga                    110
```

<210> SEQ ID NO 183
<211> LENGTH: 110
<212> TYPE: RNA
<213> ORGANISM: Homo sapiens

<400> SEQUENCE: 183

```
aaagauccuc agacaaucca ugugcuucuc uuguccuuca uuccaccgga gucugucuca         60
uacccaacca gauucagug gagugaaguu caggaggcau ggagcugaca                    110
```

<210> SEQ ID NO 184
<211> LENGTH: 71
<212> TYPE: RNA
<213> ORGANISM: Homo sapiens

<400> SEQUENCE: 184

```
guagcacuaa agucuuaua gugcagguag uguuuaguua ucuacugcau uaugagcacu          60
uaaaguacug c                                                              71
```

<210> SEQ ID NO 185
<211> LENGTH: 72
<212> TYPE: RNA
<213> ORGANISM: Homo sapiens

<400> SEQUENCE: 185

```
ugucggguag cuuaucagac ugauguugac uguugaaucu cauggcaaca ccagucgaug         60
ggcugucuga ca                                                             72
```

<210> SEQ ID NO 186
<211> LENGTH: 110
<212> TYPE: RNA
<213> ORGANISM: Homo sapiens

<400> SEQUENCE: 186

```
acccggcagu gccuccaggc gcagggcagc cccugcccac cgcacacugc gcugcccccag        60 acccacugug cgugugacag cggcugaucu ugccuggcc agcgcgaccc                    110
```

<210> SEQ ID NO 187
<211> LENGTH: 110
<212> TYPE: RNA
<213> ORGANISM: Homo sapiens

<400> SEQUENCE: 187

```
gauggcugug aguuggcuua aucucagcug gcaacuguga gauguucaua caaucccuca         60
caguggucuc ugggauuaug cuaaacagag caauuuccua gcccucacga                   110
```

<210> SEQ ID NO 188
<211> LENGTH: 110
<212> TYPE: RNA
<213> ORGANISM: Homo sapiens

<400> SEQUENCE: 188

```
gugauaaugu agcgagauuu ucuguugugc uugaucuaac caugugguug cgagguauga         60
guaaaacaug guuccgucaa gcaccaugga acgucacgca gcuuucuaca                   110
```

<210> SEQ ID NO 189
<211> LENGTH: 110
<212> TYPE: RNA
<213> ORGANISM: Homo sapiens

<400> SEQUENCE: 189
gaccagucgc ugcggggcuu uccuugugc uugaucuaac caugggugg aacgauggaa    60 acggaacaug guucugucaa gcaccgcgga aagcaccgug cucuccugca    110

<210> SEQ ID NO 190
<211> LENGTH: 85
<212> TYPE: RNA
<213> ORGANISM: Homo sapiens

<400> SEQUENCE: 190
ggcugagccg caguaguucu ucaguggcaa gcuuuauguc cugacccagc uaaagcugcc    60
aguugaagaa cuguugcccu cugcc    85

<210> SEQ ID NO 191
<211> LENGTH: 110
<212> TYPE: RNA
<213> ORGANISM: Homo sapiens

<400> SEQUENCE: 191
ugaacaucca ggucuggggc augaaccugg cauacaaugu agauuucugu guucguuagg    60
caacagcuac auugucugcu ggguuucagg cuaccuggaa acauguucuc    110

<210> SEQ ID NO 192
<211> LENGTH: 110
<212> TYPE: RNA
<213> ORGANISM: Homo sapiens

<400> SEQUENCE: 192
gcugcuggaa gguguaggua cccucaaugg cucaguagcc aguguagauc cugucuuucg    60
uaaucagcag cuacaucugg cuacgggguc ucgauggca ucuucagcu    110

<210> SEQ ID NO 193
<211> LENGTH: 110
<212> TYPE: RNA
<213> ORGANISM: Homo sapiens

<400> SEQUENCE: 193
ccuggccucc ugcagugcca cgcuccgugu auuugacaag cugaguugga cacuccaugu    60
gguagagugu caguuuguca aauaccccaa gugcggcaca ugcuuaccag    110

<210> SEQ ID NO 194
<211> LENGTH: 81
<212> TYPE: RNA
<213> ORGANISM: Homo sapiens

<400> SEQUENCE: 194
gggcuuucaa gucacuagug guccguuua guagaugauu ugcauuguu ucaaaauggu    60 gcccuaguga cuacaaagcc c    81

<210> SEQ ID NO 195
<211> LENGTH: 73
<212> TYPE: RNA
<213> ORGANISM: Homo sapiens

<400> SEQUENCE: 195
ggccggcugg gguuccuggg gauggauuu gcuuccuguc acaaaucaca uugccaggga    60
uuuccaaccg acc    73

-continued

<210> SEQ ID NO 196
<211> LENGTH: 97
<212> TYPE: RNA
<213> ORGANISM: Homo sapiens

<400> SEQUENCE: 196
cucaggugcu cuggcugcuu ggguuccugg caugcugauu ugugacuuaa gauuaaaauc    60
acauugccag ggauuaccac gcaaccacga ccuuggc                             97

<210> SEQ ID NO 197
<211> LENGTH: 68
<212> TYPE: RNA
<213> ORGANISM: Homo sapiens

<400> SEQUENCE: 197
cuccggugcc uacugagcug auaucaguuc ucauuuuaca cacuggcuca guucagcagg    60
aacaggag                                                             68

<210> SEQ ID NO 198
<211> LENGTH: 73
<212> TYPE: RNA
<213> ORGANISM: Homo sapiens

<400> SEQUENCE: 198
cucugccucc cgugccuacu gagcugaaac acaguugguu uguguacacu ggcucaguuc    60
agcaggaaca ggg                                                       73

<210> SEQ ID NO 199
<211> LENGTH: 84
<212> TYPE: RNA
<213> ORGANISM: Homo sapiens

<400> SEQUENCE: 199
ggccaguguu gagaggcgga gacuugggca auugcuggac gcugcccugg cauugcacu     60 ugucucgguc ugacagugcc ggcc                                           84

<210> SEQ ID NO 200
<211> LENGTH: 77
<212> TYPE: RNA
<213> ORGANISM: Homo sapiens

<400> SEQUENCE: 200
guggccucgu ucaaguaauc caggauaggc ugugcagguc ccaaugggcc uauucuuggu    60
uacuugcacg gggacgc                                                   77

<210> SEQ ID NO 201
<211> LENGTH: 84
<212> TYPE: RNA
<213> ORGANISM: Homo sapiens

<400> SEQUENCE: 201
ggcuguggcu ggauucaagu aauccaggau aggcuguuuc caucugugag gccuauucuu    60
gauuacuugu uucggaggc agcu                                            84

<210> SEQ ID NO 202
<211> LENGTH: 77
<212> TYPE: RNA
<213> ORGANISM: Homo sapiens

<400> SEQUENCE: 202
ccgggaccca guucaaguaa uucaggauag guugugugcu guccagccug uucuccauua    60

```
cuuggcucgg ggaccgg                                                      77

<210> SEQ ID NO 203
<211> LENGTH: 78
<212> TYPE: RNA
<213> ORGANISM: Homo sapiens

<400> SEQUENCE: 203
cugaggagca gggcuuagcu gcuugugagc aggguccaca ccaagucgug uucacagugg       60
cuaaguuccg cccccccag                                                    78

<210> SEQ ID NO 204
<211> LENGTH: 97
<212> TYPE: RNA
<213> ORGANISM: Homo sapiens

<400> SEQUENCE: 204
accucucuaa caaggugcag agcuuagcug auuggugaac agugauuggu uccgcuuug        60 uucacagugg cuaaguucug caccugaaga gaaggug                                97

<210> SEQ ID NO 205
<211> LENGTH: 64
<212> TYPE: RNA
<213> ORGANISM: Homo sapiens

<400> SEQUENCE: 205
augacugauu ucuuuuggug uucagaguca auauaauuuu cuagcaccau cugaaaucgg       60
uuau                                                                    64

<210> SEQ ID NO 206
<211> LENGTH: 81
<212> TYPE: RNA
<213> ORGANISM: Homo sapiens

<400> SEQUENCE: 206
cuucuggaag cugguuucac augguggcuu agauuuuucc aucuuuguau cuagcaccau       60
uugaaaucag uguuuuagga g                                                 81

<210> SEQ ID NO 207
<211> LENGTH: 80
<212> TYPE: RNA
<213> ORGANISM: Homo sapiens

<400> SEQUENCE: 207
aggacccuuc cagagggccc ccccucaauc cuguugugcc uaauucagag gguugggugg       60
aggcucuccu gaagggcucu                                                   80

<210> SEQ ID NO 208
<211> LENGTH: 86
<212> TYPE: RNA
<213> ORGANISM: Homo sapiens

<400> SEQUENCE: 208
acugcuaacg aaugcucuga cuuuauugca cuacuguacu uuacagcuag cagugcaaua       60
guauugucaa agcaucugaa agcagg                                            86

<210> SEQ ID NO 209
<211> LENGTH: 69
<212> TYPE: RNA
<213> ORGANISM: Homo sapiens
```

```
<400> SEQUENCE: 209
ccaccacuua aacguggaug uacuugcuuu gaaacuaaag aaguaagugc uuccauguuu    60
uggugaugg                                                           69

<210> SEQ ID NO 210
<211> LENGTH: 71
<212> TYPE: RNA
<213> ORGANISM: Homo sapiens

<400> SEQUENCE: 210
gcgacuguaa acauccucga cuggaagcug ugaagccaca gaugggcuuu cagucggaug    60
uuugcagcug c                                                        71

<210> SEQ ID NO 211
<211> LENGTH: 88
<212> TYPE: RNA
<213> ORGANISM: Homo sapiens

<400> SEQUENCE: 211
accaaguuuc aguucaugua aacauccuac acucagcugu aauacaugga uuggcuggga    60
gguggauguu uacuucagcu gacuugga                                      88

<210> SEQ ID NO 212
<211> LENGTH: 89
<212> TYPE: RNA
<213> ORGANISM: Homo sapiens

<400> SEQUENCE: 212
accaugcugu agugugugua aacauccuac acucucagcu gugagcucaa gguggcuggg    60
agaggguugu uuacuccuuc ugccaugga                                     89

<210> SEQ ID NO 213
<211> LENGTH: 72
<212> TYPE: RNA
<213> ORGANISM: Homo sapiens

<400> SEQUENCE: 213
agauacugua aacauccuac acucucagcu guggaaagua agaaagcugg gagaaggcug    60
uuuacucuuu cu                                                       72

<210> SEQ ID NO 214
<211> LENGTH: 70
<212> TYPE: RNA
<213> ORGANISM: Homo sapiens

<400> SEQUENCE: 214
guuguuguaa acaucccga cuggaagcug uaagacacag cuaagcuuuc agucagaugu    60
uugcugcuac                                                          70

<210> SEQ ID NO 215
<211> LENGTH: 92
<212> TYPE: RNA
<213> ORGANISM: Homo sapiens

<400> SEQUENCE: 215
gggcagucuu ugcuacugua aacauccuug acuggaagcu guaagguguu cagaggagcu    60
uucagucgga uguuuacagc ggcaggcugc ca                                 92
```

```
<210> SEQ ID NO 216
<211> LENGTH: 71
<212> TYPE: RNA
<213> ORGANISM: Homo sapiens

<400> SEQUENCE: 216
ggagaggagg caagaugcug gcauagcugu ugaacuggga accugcuaug ccaacauauu    60
gccaucuuuc c                                                         71

<210> SEQ ID NO 217
<211> LENGTH: 82
<212> TYPE: RNA
<213> ORGANISM: Homo sapiens

<400> SEQUENCE: 217
gcuucgcucc ccuccgccuu ucuucccgg uucuucccgg agucgggaaa agcuggguug     60
agagggcgaa aaaggaugag gu                                             82

<210> SEQ ID NO 218
<211> LENGTH: 86
<212> TYPE: RNA
<213> ORGANISM: Homo sapiens

<400> SEQUENCE: 218
uugguacuug gagagaggug guccguggcg cguucgcuuu auuuauggcg cacauuacac    60
ggucgaccuc uuugcaguau cuaauc                                         86

<210> SEQ ID NO 219
<211> LENGTH: 83
<212> TYPE: RNA
<213> ORGANISM: Homo sapiens

<400> SEQUENCE: 219
cugacuaugc cuccccgcau ccccuagggc auugguguaa agcuggagac ccacugcccc    60
aggugcugcu gggggguugua guc                                           83

<210> SEQ ID NO 220
<211> LENGTH: 95
<212> TYPE: RNA
<213> ORGANISM: Homo sapiens

<400> SEQUENCE: 220
cucaucuguc uguuggguug gaggcagggc cuuugugaag gcggguggug cucagaucgc    60
cucugggccc uuccuccagc cccgaggcgg auuca                               95

<210> SEQ ID NO 221
<211> LENGTH: 94
<212> TYPE: RNA
<213> ORGANISM: Homo sapiens

<400> SEQUENCE: 221
cuuuggcgau cacugccucu cugggccugu gucuuaggcu cugcaagauc aaccgagcaa    60
agcacacggc cugcagagag gcagcgcucu gccc                                94

<210> SEQ ID NO 222
<211> LENGTH: 94
<212> TYPE: RNA
<213> ORGANISM: Homo sapiens

<400> SEQUENCE: 222
gaguuugguu uuguuugggu uuguucuagg uaugguccca gggaucccag aucaaaccag    60
```

```
gccccugggc cuauccuaga accaaccuaa gcuc                           94

<210> SEQ ID NO 223
<211> LENGTH: 94
<212> TYPE: RNA
<213> ORGANISM: Homo sapiens

<400> SEQUENCE: 223
uguuuugagc gggggucaag agcaauaacg aaaaauguuu gcauaaacc guuuucauu   60 auugcuccug accuccucuc auuugcuaua uuca                            94

<210> SEQ ID NO 224
<211> LENGTH: 95
<212> TYPE: RNA
<213> ORGANISM: Homo sapiens

<400> SEQUENCE: 224
ggucucugug uugggcgucu gucugcccgc augccugccu cucguugcu cugaaggagg   60 caggggcugg ccugcagcu gccugggcag agcgg                             95

<210> SEQ ID NO 225
<211> LENGTH: 110
<212> TYPE: RNA
<213> ORGANISM: Homo sapiens

<400> SEQUENCE: 225
ggccagcugu gaguguuucu uuggcagugu cuuagcuggu uguugugagc aauaguaagg   60
aagcaaucag caaguauacu gcccuagaag ugcugcacgu uggggccc              110

<210> SEQ ID NO 226
<211> LENGTH: 75
<212> TYPE: RNA
<213> ORGANISM: Homo sapiens

<400> SEQUENCE: 226
agacagagaa gccaggucac gucucugcag uuacacagcu cacgagugcc ugcuggggug   60
gaaccugguc ugucu                                                   75

<210> SEQ ID NO 227
<211> LENGTH: 67
<212> TYPE: RNA
<213> ORGANISM: Homo sapiens

<400> SEQUENCE: 227
gugggccuca aauguggagc acuauucuga uguccaagug gaaagugcug cgacauuuga   60
gcgucac                                                            67

<210> SEQ ID NO 228
<211> LENGTH: 69
<212> TYPE: RNA
<213> ORGANISM: Homo sapiens

<400> SEQUENCE: 228
gggauacuca aaaugggggc gcuuuccuuu uugcuguac ugggaagugc uucgauuug   60 ggugucccc                                                         69

<210> SEQ ID NO 229
<211> LENGTH: 112
<212> TYPE: RNA
<213> ORGANISM: Homo sapiens
```

```
<400> SEQUENCE: 229
ccaccccggu ccugcucccg ccccagcagc acacuguggu uuguacggca cuguggccac    60
guccaaacca cacuguggug uuagagcgag gguggggag gcaccgccga gg             112

<210> SEQ ID NO 230
<211> LENGTH: 124
<212> TYPE: RNA
<213> ORGANISM: Homo sapiens

<400> SEQUENCE: 230
aacccuccuu gggaagugaa gcucaggcug ugauuucaag ccaggggcg uuuucuaua      60 acuggaugaa aagcaccucc agagcuugaa gcucacaguu ugagagcaau cgucaagga    120 aguu                                                                124

<210> SEQ ID NO 231
<211> LENGTH: 71
<212> TYPE: RNA
<213> ORGANISM: Homo sapiens

<400> SEQUENCE: 231
ugcccuagca gcgggaacag uucugcagug agcgaucggu gcucggggu auuguuccg      60 cugccagggu a                                                        71

<210> SEQ ID NO 232
<211> LENGTH: 78
<212> TYPE: RNA
<213> ORGANISM: Homo sapiens

<400> SEQUENCE: 232
cuuucuacac agguugggau cgguugcaau gcuguguuuc uguauggau ugcacuuguc    60 ccggccuguu gaguuugg                                                 78

<210> SEQ ID NO 233
<211> LENGTH: 75
<212> TYPE: RNA
<213> ORGANISM: Homo sapiens

<400> SEQUENCE: 233
ucaucccugg gugggauuu guugcauuac uuguguucua uauaaaguau ugcacuuguc    60
ccggccugug gaaga                                                    75

<210> SEQ ID NO 234
<211> LENGTH: 80
<212> TYPE: RNA
<213> ORGANISM: Homo sapiens

<400> SEQUENCE: 234
cugggggcuc caaagugcug uucgugcagg uagugugauu acccaaccua cugcugagcu    60
agcacuuccc gagccccccgg                                               80

<210> SEQ ID NO 235
<211> LENGTH: 78
<212> TYPE: RNA
<213> ORGANISM: Homo sapiens

<400> SEQUENCE: 235
uggccgauuu uggcacuagc acauuuuugc uugugucucu ccgcucugag caaucaugug    60
cagugccaau augggaaa                                                 78
```

```
<210> SEQ ID NO 236
<211> LENGTH: 81
<212> TYPE: RNA
<213> ORGANISM: Homo sapiens

<400> SEQUENCE: 236
cccauuggca uaaacccgua gauccgaucu uguggugaag uggaccgcac aagcucgcuu      60
cuaugggucu gugucagugu g                                              81
```